US012398133B2

(12) United States Patent
Chaves et al.

(10) Patent No.: US 12,398,133 B2
(45) Date of Patent: *Aug. 26, 2025

(54) SOLID STATE FORMS

(71) Applicant: AMGEN INC., Thousand Oaks, CA (US)

(72) Inventors: Mary Chaves, Arlington, MA (US); Patricia Lopez, Woodland Hills, CA (US); Prashant Agarwal, Chelsea, MA (US); Albert Amegadzie, Westlake Village, CA (US); Stephanie Azali, Woodland Hills, CA (US); Roman Shimanovich, Brighton, MA (US); Ron C. Kelly, Westlake Village, CA (US); Darren Leonard Reid, Belmont, MA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/382,927

(22) Filed: Oct. 23, 2023

(65) Prior Publication Data

US 2024/0067647 A1 Feb. 29, 2024

Related U.S. Application Data

(63) Continuation of application No. 17/553,598, filed on Dec. 16, 2021, now Pat. No. 11,827,635, which is a continuation of application No. 16/878,824, filed on May 20, 2020, now Pat. No. 11,236,091.

(60) Provisional application No. 62/851,044, filed on May 21, 2019.

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .................................................... C07D 471/04
USPC .................................................... 514/264.11
See application file for complete search history.

(56) References Cited

U.S. PATENT DOCUMENTS

| | | |
|---|---|---|
| 4,232,027 A | 11/1980 | Turk et al. |
| 5,100,883 A | 3/1992 | Schiehser |
| 5,118,677 A | 6/1992 | Caufield |
| 5,118,678 A | 6/1992 | Kao et al. |
| 5,120,842 A | 6/1992 | Failli et al. |
| 5,151,413 A | 9/1992 | Caufield et al. |
| 5,256,790 A | 10/1993 | Nelson |
| 5,258,389 A | 11/1993 | Goulet et al. |
| 5,521,184 A | 5/1996 | Zimmerman |
| 5,650,415 A | 7/1997 | Tang et al. |
| 5,656,643 A | 8/1997 | Spada et al. |
| 5,712,291 A | 1/1998 | D'Amato |
| 5,728,813 A | 3/1998 | Lyman et al. |
| 5,747,498 A | 5/1998 | Schnur et al. |
| 5,770,599 A | 6/1998 | Gibson |
| 5,789,427 A | 8/1998 | Chen et al. |
| 5,792,783 A | 8/1998 | Tang et al. |
| 5,861,510 A | 1/1999 | Piscopio et al. |
| 5,863,949 A | 1/1999 | Robinson et al. |
| 5,892,112 A | 4/1999 | Levy et al. |
| 5,969,110 A | 10/1999 | Beckmann et al. |
| 5,981,245 A | 11/1999 | Fox et al. |
| 5,990,141 A | 11/1999 | Hirth et al. |
| 6,057,124 A | 5/2000 | Bartley et al. |
| 6,111,090 A | 8/2000 | Gorman et al. |
| 6,232,447 B1 | 5/2001 | Cerretti |
| 6,235,764 B1 | 5/2001 | Larson et al. |
| 6,258,812 B1 | 7/2001 | Bold et al. |
| 6,413,932 B1 | 7/2002 | Cerretti et al. |
| 6,515,004 B1 | 2/2003 | Misra et al. |
| 6,596,852 B2 | 7/2003 | Cerretti et al. |
| 6,630,500 B2 | 10/2003 | Gingrich et al. |
| 6,656,963 B2 | 12/2003 | Firestone et al. |
| 6,713,485 B2 | 3/2004 | Carter et al. |
| 6,727,225 B2 | 4/2004 | Wiley |
| 7,025,962 B1 | 4/2006 | Gorman et al. |
| 7,354,944 B2 | 4/2008 | Zeng et al. |
| 7,361,760 B2 | 4/2008 | Sircar et al. |
| 7,514,566 B2 | 4/2009 | Zeng et al. |
| 7,618,632 B2 | 11/2009 | Collins et al. |
| 7,700,636 B2 | 4/2010 | Monenschein et al. |
| 7,812,135 B2 | 10/2010 | Smith et al. |
| 7,897,619 B2 | 3/2011 | Zeng et al. |
| 7,919,504 B2 | 4/2011 | Zeng et al. |

(Continued)

FOREIGN PATENT DOCUMENTS

| | | |
|---|---|---|
| DE | 19629652 A1 | 1/1998 |
| EP | 0090505 A2 | 10/1983 |

(Continued)

OTHER PUBLICATIONS

Caira, "Crystalline Polymorphism of Organic Compounds," in Design of Organic Solids, Topics in Current Chemistry 198, Weber (Ed.) Springer, Berlin Heidelberg, 163-208 (1998).

Brittain et al., "Polymorphism in Pharmaceutical Solids," Chapters 1 and 5, Marcel Dekker, 1999.

Byrn et al., "Pharmaceutical solids: a strategic approach to regulatory considerations," Pharm. Res. 12(7):945-954 (1995).

Darvin et al., "Immune checkpoint inhibitors: recent progress and potential biomarkers," Experimental & Molecular Medicine 50:165 (pp. 1-11) (2018).

(Continued)

*Primary Examiner* — Niloofar Rahmani
(74) *Attorney, Agent, or Firm* — Markus Bergauer

(57) ABSTRACT

The present disclosure provides crystalline and amorphous forms of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, including several anhydrous, hydrate and solvate forms, and solid state forms thereof, pharmaceutical compositions, and methods of treating a disease mediated by KRAS G12C inhibition.

42 Claims, 33 Drawing Sheets

(56) References Cited

U.S. PATENT DOCUMENTS

| | | |
|---|---|---|
| 7,919,514 B2 | 4/2011 | Monenschein et al. |
| 8,388,967 B2 | 3/2013 | Smith et al. |
| 8,586,023 B2 | 11/2013 | Shiku et al. |
| 8,591,886 B2 | 11/2013 | Ponath et al. |
| 10,519,146 B2 | 12/2019 | Lanman et al. |
| 10,532,042 B2 | 1/2020 | Lanman et al. |
| 10,640,504 B2 | 5/2020 | Lanman et al. |
| 10,988,485 B2 | 4/2021 | Minatti et al. |
| 11,045,484 B2 | 6/2021 | Wurz et al. |
| 11,053,226 B2 | 7/2021 | Shin et al. |
| 11,090,304 B2 | 8/2021 | Allen et al. |
| 11,096,939 B2 | 8/2021 | Booker et al. |
| 11,236,091 B2 * | 2/2022 | Chaves ............. C07D 471/04 |
| 11,285,135 B2 | 3/2022 | Lanman et al. |
| 11,285,156 B2 | 3/2022 | Allen et al. |
| 11,299,491 B2 | 4/2022 | Parsons et al. |
| 11,306,087 B2 | 4/2022 | Lanman et al. |
| 11,426,404 B2 | 8/2022 | Henary et al. |
| 11,439,645 B2 | 9/2022 | Lipford et al. |
| 11,766,436 B2 | 9/2023 | Allen et al. |
| 11,827,635 B2 * | 11/2023 | Chaves .................. A61P 35/00 |
| 11,905,281 B2 | 2/2024 | Lanman et al. |
| 11,918,584 B2 | 3/2024 | Lipford et al. |
| 11,993,597 B2 | 5/2024 | Lanman et al. |
| 12,083,121 B2 | 9/2024 | Allen et al. |
| 12,280,056 B2 | 4/2025 | Lipford et al. |
| 2002/0042368 A1 | 4/2002 | Fanslow, III et al. |
| 2003/0105091 A1 | 6/2003 | Riedl et al. |
| 2003/0162712 A1 | 8/2003 | Cerretti et al. |
| 2009/0012085 A1 | 1/2009 | Baum et al. |
| 2009/0023761 A1 | 1/2009 | Chen et al. |
| 2009/0030002 A1 | 1/2009 | Chen et al. |
| 2009/0054405 A1 | 2/2009 | Booker et al. |
| 2009/0137581 A1 | 5/2009 | Chen et al. |
| 2009/0163489 A1 | 6/2009 | Booker et al. |
| 2009/0270445 A1 | 10/2009 | Zeng et al. |
| 2010/0273764 A1 | 10/2010 | Andrews et al. |
| 2010/0331293 A1 | 12/2010 | Chushing et al. |
| 2010/0331306 A1 | 12/2010 | Bui et al. |
| 2011/0092504 A1 | 4/2011 | Bo et al. |
| 2011/0097305 A1 | 4/2011 | Connors et al. |
| 2014/0288045 A1 | 9/2014 | Ren et al. |
| 2015/0239900 A1 | 8/2015 | Li et al. |
| 2016/0159738 A1 | 6/2016 | Ren et al. |
| 2016/0166571 A1 | 6/2016 | Janes et al. |
| 2016/0297774 A1 | 10/2016 | Li et al. |
| 2018/0015087 A1 | 1/2018 | Liu et al. |
| 2018/0072723 A1 | 3/2018 | Blake et al. |
| 2018/0334454 A1 * | 11/2018 | Lanman ............... A61K 31/416 |
| 2018/0362529 A1 | 12/2018 | Chen et al. |
| 2019/0374542 A1 | 12/2019 | Allen et al. |
| 2019/0375749 A1 | 12/2019 | Chen et al. |
| 2020/0055845 A1 | 2/2020 | Lanman et al. |
| 2020/0069657 A1 | 3/2020 | Lanman et al. |
| 2020/0207766 A1 | 7/2020 | Lanman et al. |
| 2020/0216446 A1 | 7/2020 | Parsons et al. |
| 2020/0222407 A1 | 7/2020 | Lipford et al. |
| 2020/0360374 A1 | 11/2020 | Henary et al. |
| 2021/0009577 A1 | 1/2021 | Lanman et al. |
| 2022/0002298 A1 | 1/2022 | Chen et al. |
| 2022/0106313 A1 | 4/2022 | Chaves et al. |
| 2022/0168280 A1 | 6/2022 | Lanman et al. |
| 2022/0175782 A1 | 6/2022 | Allen et al. |
| 2022/0213101 A1 | 7/2022 | Lanman et al. |
| 2022/0220112 A1 | 7/2022 | Parsons et al. |
| 2022/0235045 A1 | 7/2022 | Chaves et al. |
| 2022/0378787 A1 | 12/2022 | Henary et al. |
| 2022/0395504 A1 | 12/2022 | Allen et al. |
| 2023/0028414 A1 | 1/2023 | Henary et al. |
| 2023/0121955 A1 | 4/2023 | Lipford et al. |
| 2023/0248729 A1 | 8/2023 | Henary et al. |
| 2024/0050430 A1 | 2/2024 | Allen et al. |
| 2024/0082251 A1 | 3/2024 | Henary et al. |
| 2024/0173328 A1 | 5/2024 | Lipford et al. |
| 2024/0174660 A1 | 5/2024 | Lanman et al. |
| 2024/0190862 A1 | 6/2024 | Wang et al. |
| 2024/0245686 A1 | 7/2024 | Lipford et al. |
| 2024/0287068 A1 | 8/2024 | Lanman et al. |
| 2024/0408089 A1 | 12/2024 | Henary et al. |
| 2025/0057817 A1 | 2/2025 | Lanman et al. |

FOREIGN PATENT DOCUMENTS

| | | |
|---|---|---|
| EP | 404355 A1 | 12/1990 |
| EP | 511792 A2 | 11/1992 |
| EP | 0520722 A1 | 12/1992 |
| EP | 0566226 A1 | 10/1993 |
| EP | 0606046 A1 | 7/1994 |
| EP | 0682027 A1 | 11/1995 |
| EP | 0407122 A1 | 10/1996 |
| EP | 0770622 A2 | 5/1997 |
| EP | 0780386 A1 | 6/1997 |
| EP | 0787772 A2 | 8/1997 |
| EP | 0818442 A2 | 1/1998 |
| EP | 0837063 A1 | 4/1998 |
| EP | 0931788 A2 | 7/1999 |
| EP | 0970070 B1 | 1/2000 |
| EP | 1004578 A2 | 5/2000 |
| EP | 1181017 B1 | 2/2002 |
| EP | 1786785 B9 | 5/2007 |
| EP | 1866339 B1 | 12/2007 |
| EP | 1947183 A1 | 7/2008 |
| EP | 3401314 A1 | 11/2019 |
| EP | 3055290 B1 | 12/2019 |
| JP | 02233610 A | 9/1990 |
| JP | 2019031476 A | 2/2019 |
| WO | 1990005719 A1 | 5/1990 |
| WO | 1992005179 A1 | 4/1992 |
| WO | 1992020642 A1 | 11/1992 |
| WO | 1993011130 A1 | 6/1993 |
| WO | 1994002136 A1 | 2/1994 |
| WO | 1994002485 A1 | 2/1994 |
| WO | 1994009010 A1 | 4/1994 |
| WO | 1995009847 A1 | 4/1995 |
| WO | 1995014023 A1 | 5/1995 |
| WO | 1995016691 A1 | 6/1995 |
| WO | 1995019774 A1 | 7/1995 |
| WO | 1995019970 A1 | 7/1995 |
| WO | 1996027583 A1 | 9/1996 |
| WO | 1996030347 A1 | 10/1996 |
| WO | 1996031510 A1 | 10/1996 |
| WO | 1996033172 A1 | 10/1996 |
| WO | 1996033980 A1 | 10/1996 |
| WO | 1996041807 A1 | 12/1996 |
| WO | 1997002266 A1 | 1/1997 |
| WO | 1997013771 A1 | 4/1997 |
| WO | 1997019065 A1 | 5/1997 |
| WO | 1997027199 A1 | 7/1997 |
| WO | 1997030034 A1 | 8/1997 |
| WO | 1997030044 A1 | 8/1997 |
| WO | 1997032880 A1 | 9/1997 |
| WO | 1997032881 A1 | 9/1997 |
| WO | 1997034895 A1 | 9/1997 |
| WO | 1997038983 A1 | 10/1997 |
| WO | 1997038994 A1 | 10/1997 |
| WO | 1997049688 A1 | 12/1997 |
| WO | 1998002434 A1 | 1/1998 |
| WO | 1998002437 A1 | 1/1998 |
| WO | 1998002438 A1 | 1/1998 |
| WO | 1998002441 A2 | 1/1998 |
| WO | 1998003516 A1 | 1/1998 |
| WO | 1998007697 A1 | 2/1998 |
| WO | 1998007726 A1 | 2/1998 |
| WO | 1998014449 A1 | 4/1998 |
| WO | 1998014450 A1 | 4/1998 |
| WO | 1998014451 A1 | 4/1998 |
| WO | 1998017662 A1 | 4/1998 |
| WO | 1998030566 A1 | 7/1998 |
| WO | 1998033768 A1 | 8/1998 |
| WO | 1998033798 A2 | 8/1998 |
| WO | 1998034915 A1 | 8/1998 |
| WO | 1998034918 A1 | 8/1998 |
| WO | 1999007675 A1 | 2/1999 |
| WO | 1999007701 A1 | 2/1999 |

(56) References Cited

FOREIGN PATENT DOCUMENTS

| | | |
|---|---|---|
| WO | 1999020758 A1 | 4/1999 |
| WO | 1999029667 A1 | 6/1999 |
| WO | 1999035132 A1 | 7/1999 |
| WO | 1999035146 A1 | 7/1999 |
| WO | 1999040196 A1 | 8/1999 |
| WO | 1999045009 A1 | 9/1999 |
| WO | 1999052889 A1 | 10/1999 |
| WO | 1999052910 A1 | 10/1999 |
| WO | 1999061422 A1 | 12/1999 |
| WO | 2000002871 A1 | 1/2000 |
| WO | 2000012089 A1 | 3/2000 |
| WO | 2000059509 A1 | 10/2000 |
| WO | 2001003720 A2 | 1/2001 |
| WO | 2001014387 A1 | 3/2001 |
| WO | 2001032651 A1 | 5/2001 |
| WO | 2001037820 A2 | 5/2001 |
| WO | 2002055501 A2 | 7/2002 |
| WO | 2002059110 A1 | 8/2002 |
| WO | 2002066470 A1 | 8/2002 |
| WO | 2002068406 A2 | 9/2002 |
| WO | 2004005279 A2 | 1/2004 |
| WO | 2004007458 A1 | 1/2004 |
| WO | 2004007481 A2 | 1/2004 |
| WO | 2004009784 A2 | 1/2004 |
| WO | 2004063195 A1 | 7/2004 |
| WO | 2005005434 A1 | 1/2005 |
| WO | 2005007190 A1 | 1/2005 |
| WO | 2005011700 A1 | 2/2005 |
| WO | 2005016252 A2 | 2/2005 |
| WO | 2005021546 A1 | 3/2005 |
| WO | 2005055808 A2 | 6/2005 |
| WO | 2005115451 A2 | 12/2005 |
| WO | 2006044453 A1 | 4/2006 |
| WO | 2006083289 A2 | 8/2006 |
| WO | 2006121168 A1 | 11/2006 |
| WO | 2006122806 A2 | 11/2006 |
| WO | 2007133822 A1 | 11/2007 |
| WO | 2008070740 A1 | 6/2008 |
| WO | 2008118454 A2 | 10/2008 |
| WO | 2008118455 A1 | 10/2008 |
| WO | 2008118468 A1 | 10/2008 |
| WO | 2008153947 A2 | 12/2008 |
| WO | 2009036082 A2 | 3/2009 |
| WO | 2009055730 A1 | 4/2009 |
| WO | 2009085185 A1 | 7/2009 |
| WO | 2010003118 A1 | 1/2010 |
| WO | 2010083246 A1 | 7/2010 |
| WO | 2010096314 A1 | 8/2010 |
| WO | 2010108074 A2 | 9/2010 |
| WO | 2010126895 A1 | 11/2010 |
| WO | 2010132598 A1 | 11/2010 |
| WO | 2010149786 A1 | 12/2010 |
| WO | 2010151735 A2 | 12/2010 |
| WO | 2010151737 A2 | 12/2010 |
| WO | 2010151740 A2 | 12/2010 |
| WO | 2010151791 A1 | 12/2010 |
| WO | 2011028683 A1 | 3/2011 |
| WO | 2011031842 A1 | 3/2011 |
| WO | 2011051726 A1 | 5/2011 |
| WO | 2011090754 A1 | 7/2011 |
| WO | 2012142498 A2 | 10/2012 |
| WO | 2013039954 A1 | 3/2013 |
| WO | 2013155223 A1 | 10/2013 |
| WO | 2014023385 A1 | 2/2014 |
| WO | 2014143659 A1 | 9/2014 |
| WO | 2014152588 A1 | 9/2014 |
| WO | 2015001076 A1 | 1/2015 |
| WO | 2015054572 A1 | 4/2015 |
| WO | 2015075483 A1 | 5/2015 |
| WO | 2015109285 A1 | 7/2015 |
| WO | 2016035008 A1 | 3/2016 |
| WO | 2016044772 A1 | 3/2016 |
| WO | 2016049524 A1 | 3/2016 |
| WO | 2016049565 A1 | 3/2016 |
| WO | 2016049568 A1 | 3/2016 |
| WO | 2016164675 A1 | 10/2016 |
| WO | 2016168540 A1 | 10/2016 |
| WO | 2017015562 A1 | 1/2017 |
| WO | 2017058728 A1 | 4/2017 |
| WO | 2017058768 A1 | 4/2017 |
| WO | 2017058792 A1 | 4/2017 |
| WO | 2017058805 A1 | 4/2017 |
| WO | 2017058807 A1 | 4/2017 |
| WO | 2017058902 A1 | 4/2017 |
| WO | 2017058915 A1 | 4/2017 |
| WO | 2017087528 A1 | 5/2017 |
| WO | 2017100546 A1 | 6/2017 |
| WO | 2017172979 A1 | 10/2017 |
| WO | 2017201161 A1 | 11/2017 |
| WO | 2018064510 A1 | 4/2018 |
| WO | 2018068017 A1 | 4/2018 |
| WO | 2018119183 A2 | 6/2018 |
| WO | 2018119183 A3 | 6/2018 |
| WO | 2018140598 A1 | 8/2018 |
| WO | 2018217651 A1 | 11/2018 |
| WO | 2018218069 A1 | 11/2018 |
| WO | 2019051291 A1 | 3/2019 |
| WO | 2019213516 A1 | 11/2019 |
| WO | 2019213526 A1 | 11/2019 |
| WO | 2019217691 A1 | 11/2019 |
| WO | 2019232419 A1 | 12/2019 |
| WO | 2019241157 A1 | 12/2019 |
| WO | 2019243533 A1 | 12/2019 |
| WO | 2019243535 A1 | 12/2019 |
| WO | 2020050890 A2 | 3/2020 |
| WO | 2020102730 A1 | 5/2020 |
| WO | 2020106640 A1 | 5/2020 |
| WO | 2020232130 A1 | 11/2020 |
| WO | 2020236947 A1 | 11/2020 |
| WO | 2020236948 A1 | 11/2020 |
| WO | 2021081212 A1 | 4/2021 |
| WO | 2021097207 A1 | 5/2021 |
| WO | 2021097212 A1 | 5/2021 |
| WO | 2021126816 A1 | 6/2021 |
| WO | 2021236920 A1 | 11/2021 |
| WO | 2002006213 A2 | 1/2022 |

OTHER PUBLICATIONS

Kojima et al., "Optimization of development format in drug development", Pharmacia, 387-391 (2016) (including English abstract).
Non-Final Office Action for U.S. Appl. No. 18/213,464, mailed Jul. 25, 2024, 18 pages.
Ono, "Present state analysis of salt selection", Journal of Pharmaceutical Science and Technology, 176-182 (2013) (including English abstract).
PubChem, http://www.ncbi.nlm.nih.gov/#query=sotorasib, National Library of Medicine, Sotorasib; pp. 1-3 (Jan. 26, 2019).
Shah et al., "Approaches for Improving Bioavailability of Poorly Soluble Drugs," in Augsburger and Hoag, "Pharmaceutical Dosage Forms—Tablets: Rational Design and Formulation", CRC Press, vol. 2, Chapter 2, pp. 51-104 (2008).
"A Phase 1, Study Evaluating the Safety, Tolerability, PK, and Efficacy of AMG 510 in Subjects With Solid Tumors With a S Mutation." NCT03600883, comparison of version submitted Apr. 3, 2019 and May 6, 2020 (update posted May 7, 2020), for full history of changes see https://clinicaltrials.gov/ct2/history/NCT03600883 (last accessed Nov. 11, 2020), pp. 1-21.
"A Phase 1b Protocol AMG 510 Activity in Subjects With Advanced Solid Tumors With KRAS p.G12C Mutation (CodeBreak 101)." NCT04185883, comparison of version submitted Dec. 3, 2019 and Apr. 3, 2020 (update posted Apr. 7, 2020), for full history of changes see https://clinicaltrials.gov/ct2/history/NCT04185883 (last accessed Nov. 11, 2020), pp. 1-11.
"Study to Compare AMG 510 "Proposed INN Sotorasib" With Docetaxel in Non Small Cell Lung Cancer (NSCLC) (CodeBreak 200)" NCT04303780, comparison of version submitted Mar. 9, 2020 and Apr. 22, 2020 (update posted Apr. 24, 2020), for full history of changes see https://clinicaltrials.gov/ct2/history/NCT04303780 (last accessed Nov. 11, 2020), pp. 1-9.
"Acute Leukemia," *The Merck Manual* (Online Edition), pp. 1-6 (2013).

(56) References Cited

OTHER PUBLICATIONS

"KRASG12C Inhibitor," Mirati Therapeutics, retrieved on Nov. 27, 2018, from https://www.mirati.com/mrtx849/, 5 pages.
4-methyl-2-(1-methylethyl)-3-Pyridinamine, STN Registry, CAS RN 1698293-93-4, STN entry date May 5, 2015 (May 5, 2015).
Aggarwal, et al., "Clinicopathological characteristics and treatment patterns observed in real-world care in patients with advanced non-small cell lung cancer(NSCLC) and KRAS G12C mutationsin the Flatiron Health (FH)-Foundation Medicine (FMI) Clinico-Genomic Database (CGDB)," Abstract and Presentation, ESMO Virtual Congress, Sep. 19-21, 2020.
Ahmadian, et al., "Guanosine triphosphatase stimulation of oncogenic Ras mutants," *PNAS*, 96: 7065-7070, 1999.
Airoldi, et al., "Glucose-Derived Ras Pathway Inhibitors: Evidence of Ras—Ligand Binding and Ras—GEF (Cdc25) Interaction Inhibition," *ChemBioChem*, 8: 1376-1379 (2007).
AMG-510; CS-0081316; Source: AbaChemScene (CS-0081316); Deposit Date: May 13, 2019 Available Date: May 13, 2019; SID: 384060804[CID: 137278711] (available at https://pubchem.ncbi.nlm.nih.gov/substance/384060804/).
AMG-510; HY-114277; Source: MedChemexpress MCE (HY-114277); Deposit Date: May 13, 2019 Available Date: May 13, 2019; SID: 384060569[CID: 137278711] (available at https://pubchem.ncbi.nlm.nih.gov/substance/384060569).
Amgen Press Release, "Amgen Announces New Clinical Data Evaluating Novel Investigational KRAS(G12C) Inhibitor in Larger Patient Group At WCLC 2019," dated Sep. 8, 2019 (last accessed Apr. 13, 2021).
ATTC "Organism: *Mus musculus* (B cell); *Mus musculus* (myeloma), mouse (B cell); mouse (myeloma)," Accession No. HB-8508, retrieved from https://www.atcc.org/~/media/0DF7351153724BD6A3E7D78D5BA2F933.ashx, on Nov. 29, 2018.
Barnett, et al., "Identification and characterization of pleckstrin-holomogy-domain-dependent and isoenzyme specific Akt inhibitors," *Biochem. J.*, 385 (2): 399-408 (2005).
Bhatia, et al., "A Review on Bioisosterism: A Rational Approach for Drug Design and Molecular Modification," *Pharmacologyonline*, 1:272-299 (2011).
Bull, et al., "Isoquino[2,1-c][1,3,2] Benzodiazaphosphorine Derivatives: New Potential Agents for Cancer Chemotherapy," *Phosphorus, Sulfur, and Silicon*, 162:231-243 (2000).
Campillo, et al., "Novel Bronchodilators: Synthesis, Transamination Reactions, and Pharmacology of a Series of Pyrazino[2,3-c][1,2,6]thiadiazine 2,2-Dioxides," *J. Med. Chem.*, 43: 4219-4227 (2000).
Canon, et al., "The clinical KRAS(G12C) inhibitor AMG 510 drives anti-tumour immunity," *Nature*, 575(7781): 217-223 (2019).
Canon, et al., "The clinical KRAS(G12C) inhibitor AMG 510 drives anti-tumour immunity," *Nature*, 575(7781): 217-223 (2019) (Supplementary Material, pp. 1-55).
Cee, et al., "Discovery of AMG 510, a first-in-humancovalent inhibitor of KRAS$^{G12C}$ for the treatment of solid tumors," Abstract and Presentation, ACS Spring Meeting, Orlando, FL, USA, Mar. 31-Apr. 4, 2019.
Cohen, "The development and therapeutic potential of protein kinase inhibitors," *Current Opinion in Chemical Biology*, 3:459-465 (1999).
Cowen Slide deck—Warp Drive Bio, slides 1-32, "Corporate Overview Exploiting the Molecules and Mechanisms of Nature to Create Transformative Medicines" http://www.warpdrivebio.com/news/cowen%202016.pdf (last visited Apr. 2016).
Dasmahapatra, et al., "In vitro Combination Treatment with Perifosine and UCN-01 Demonstrates Synergism Against Prostate (PC-3) and Lung (A549) Epithelial Adenocarcinoma Cell Lines," *Clin. Cancer Res.* 10(15): 5242-5252 (2004).
Database Registry [Online], Chemical Abstracts Service, Columbus, Ohio, US; Jul. 31, 2017 (Jul. 31, 2017), XP002801805, retrieved from STN Database accession No. 2105944-09-8.
Dermer, et al., "Another Anniversary for the War on Cancer," *Bio/Technology*, 12: 320 (1994).
Douelle, et al., "Highly Diastereoselective Synthesis of vicinal Quaternary and Tertiary Stereocenters Using the Iodo-aldol Cyclization," *Org. Lett.*, 9 (10): 1931-1934 (2007).
Durm, et al., "Durability of clinical benefit and biomarkers in patients with advanced non-small cell lung cancer (NSCLC) treated with AMG 510 (sotorasib): CodeBreak 100," Presentation, North America Conference on Lung Cancer (NACLC), Virtual Worldwide Event, Oct. 16-17, 2020.
Erkkilä, et al., "Mild Organocatalytic α-Methylenation of Aldehydes," *J. Org. Chem.*, 71 (6), 2538-2541 (2006).
Extended European Search Report for European Patent Application No. 19208193.2, dated Jun. 3, 2020, pp. 1-8.
Fakih, et al., "Phase 1 study evaluating the safety, tolerability, pharmacokinetics (PK), and efficacy of AMG 510, a novel small molecule KRASG12C inhibitor, in advanced solid tumors," *Journal of Clinical Oncology*, 37(15 suppl) (May 20, 2019) 3003, published online May 26, 2019.
Fakih, et al., "Phase 1 study evaluating the safety, tolerability, pharmacokinetics (PK), and efficacy of AMG 510, a novel small molecule KRASG12C inhibitor, in advanced solid tumors," Presentation, ASCO, Chicago, IL, USA, May 31-Jun. 4, 2019.
Fakih, et al., "CodeBreak 100: Activity of AMG 510, a novel small molecule inhibitor of KRAS$^{G12C}$, in patients with advanced colorectal cancer," Abstract and Poster, ASCO Virtual Meeting, May 29-31, 2020.
Fakih, et al., "Trial in progress: A phase 1b study of AMG510, a specific and irreversible KRAS$^{G12C}$ inhibitor, in combination with other anticancer therapies in patients with advanced solid tumors harboring KRASp.G12C mutation (CodeBreak*TM* 101Trial)," Abstract and Poster, ASCO Virtual Meeting, May 29-31, 2020.
Falchook, et al., "Trial in Progress: A Phase 1b Study of Sotorasib (AMG510), a Specific and Irreversible KRAS$^{G12C}$ Inhibitor, In Combination With OtherAnticancer Therapies in Patients With Advanced Solid Tumors Harboring KRAS p.G12C Mutation (CodeBreak101)," Presentation, North America Conference on Lung Cancer (NACLC), Virtual Worldwide Event, Oct. 16-17, 2020.
Final Office Action for U.S. Appl. No. 15/984,855, mailed Mar. 28, 2019, 7 pages.
Final Office Action for U.S. Appl. No. 16/436,647, mailed Mar. 24, 2021, 7 pages.
Final Office Action for U.S. Appl. No. 16/661,907, mailed Mar. 27, 2020, 29 pages.
Freshney, et al., Culture of Animal Cells, *A Manual of Basic Technique*, Alan R. Liss, Inc, New York, p. 4 (1983).
Gentile, et al., "Discovery and Structural Investigation of Novel Binders to the Ras Switch II Pocket," NCI Initiative Symposium Poster (2015).
Gills and Dennis, "The development of phosphatidylinositol ether lipid analogues as inhibitors of the serine/threonine kinase, Akt," *Expert. Opin. Investig. Drugs*, 13: 787-797 (2004).
Goldberg, et al., "Role of PD-1 and its ligand, B7-H1, in early fate decisions of CD8 T cells," *Blood*, 110(1): 186-192 (2007).
Goldstein, et al., "Biological efficacy of a chimeric antibody to the epidermal growth factor receptor in a human tumor xenograft model," *Clin. Cancer Res.*, 1: 1311-1318 (1995).
Golub, et al., "Molecular Classification of Cancer: Class Discovery and Class Prediction by Gene Expression Monitoring," *Science*, 286: 531-537(1999).
Govindan et al., "OA01.06 Safety, Efficacy, and Pharmacokinetics of AMG 510, a Novel KRAS$^{G12C}$ Inhibitor, in Patients with Non-Small Cell Lung Cancer," *J. Thorac. Oncol.*, 14(11, Supplement 1):S1125-1126 (Nov. 2019).
Govindan, et al., "Safety, Efficacy, and Pharmacokinetics of AMG 510, a Novel KRASG12C Inhibitor, in Patients with Non-Small Cell Lung Cancer," Abstract and Presentation, North American Conference on Lung Cancer (NACLC), Chicago, IL, USA, Oct. 10-12, 2019.
Govindan, et al., "Phase 1 Study of AMG 510, a Novel KRAS G12C Inhibitor, in Advanced Solid Tumors with KRAS p.G12C Mutation," Abstract, ESMO Congress, Barcelona, Spain, Sep. 27-Oct. 1, 2019.

(56) References Cited

OTHER PUBLICATIONS

Govindan, et al., "Phase 1 Study of AMG 510, a Novel KRAS G12C Inhibitor, in Advanced Solid Tumors with KRAS p.G12C Mutation," Poster, ESMO Congress, Barcelona, Spain, Sep. 27, 2019-Oct. 1, 2019.

Govindan, et al., "Phase 1 Study of Safety, Tolerability, Pharmacokinetics, and Efficacy of AMG 510, a Novel KRAS$^{G12C}$ Inhibitor, in Non-Small Cell Lung Cancer," Abstract and Presentation, World Conference on Lung Cancer (WCLC), Barcelona, Spain, Sep. 7-10, 2019.

Gura, "Cancer Models: Systems for Identifying New Drugs Are Often Faulty," *Science*, 278(5340):1041-1042 (1997).

Halford, "Amgen unveils its Kras covalent inhibitor AMG 510," *Chemical & Engineering News* 97(14):4 (2019).

Hallin, et al., "The KRAS$^{G12C}$ Inhibitor MRTX849 Provides Insight toward Therapeutic Susceptibility of KRAS-Mutant Cancers in Mouse Models and Patients," *Cancer Discov.*, 10: 54-71 (2020).

Hansen, et al., "Abstract 686: Drugging an undruggable pocket: the biochemical mechanism of covalent KRAS$^{G12C}$ inhibitors," Proceedings of the American Association for Cancer Research Annual Meeting 2018; Apr. 14-18, 2018; Chicago, IL; AACR; *Cancer Res.*, 78(13 Suppl): Abstract 686 (2018).

Hichri, et al., "A Convenient Synthesis of 1,3,2-Benzodiazaphophorine-2-Oxide," *Phosphorus, Sulfur, and Silicon*, 190: 29-35 (2015).

Hichri, et al., Caplus Abstract, 162:245378 (2015).

Hirayama, "Handbook for Making Crystal of Organic Compound,—Principles and Know-how—", Maruzen Co., Ltd., Jul. 25, 2008, pp. 57-84 (incl. English translation).

Hocker, et al., "Andrographolide derivatives inhibit guanine nucleotide exchange and abrogate oncogenic Ras function," *PNAS*, 110(25): 10201-10206 (2013).

Hong, et al., "Durability of clinical benefit and biomarkers in patients with advanced non-small cell lung cancer (NSCLC) treated with AMG 510 (sotorasib): CodeBreak 100," Abstract and Presentation, ESMO Virtual Congress, Sep. 19-21, 2020.

Hong, et al., "CodeBreak 100: Phase 1 study of AMG 510, a novel KRAS$^{G12C}$ inhibitor, in patients (pts) with advanced solid tumors other than non-small-cell lung cancer (NSCLC) and colorectal cancer (CRC)," Abstract and Poster, ASCO Virtual Meeting, May 29-31, 2020.

Hong, et al., "KRAS$^{G12C}$ Inhibition with Sotorasib in Advanced Solid Tumors," *N. Engl. Med.*, 383:1207-1217 (2020).

Huang, et al., "Epidermal Growth Factor Receptor Blockade with C225 Modulates Proliferation, Apoptosis, and Radiosensitivity in Squamous Cell Carcinomas of the Head and Neck," *Cancer Res.*, 59(8): 1935-1940 (1999).

International Search Report for PCT/US2017/067801, mailed Jul. 25, 2018, 6 pages.

International Search Report for PCT/US2018/033714, mailed Jul. 17, 2018, 3 pages.

International Search Report for PCT/US2018/050044, mailed Oct. 30, 2018, 7 pages.

International Search Report for PCT/US2019/030593, mailed Aug. 6, 2019, 4 pages.

International Search Report for PCT/US2019/030606, mailed Jul. 23, 2019, 5 pages.

International Search Report for PCT/US2019/031535, mailed Jul. 25, 2019, 7 pages.

International Search Report for PCT/US2019/034974, mailed Aug. 9, 2019, 5 pages.

International Search Report for PCT/US2019/036397, mailed Aug. 26, 2019, 5 pages.

International Search Report for PCT/US2019/036626, mailed Jun. 2, 2020, 5 pages.

International Search Report for PCT/US2019/061815, mailed Mar. 5, 2020, 6 pages.

International Search Report for PCT/US2019/062051, mailed Mar. 2, 2020, 3 pages.

International Search Report for PCT/US2019/62064, mailed Oct. 29, 2020, 9 pages.

International Search Report for PCT/US2020/032686, mailed Aug. 14, 2020, 4 pages.

International Search Report for PCT/US2020/033831, mailed Jul. 9, 2020, 6 pages.

International Search Report for PCT/US2020/033832, mailed Jul. 8, 2020, 4 pages.

International Search Report for PCT/US2020/056874, mailed Feb. 12, 2021, 7 pages.

International Search Report for PCT/US2020/060415, mailed Feb. 3, 2021, 7 pages.

International Search Report for PCT/US2020/065050, mailed Mar. 29, 2021, 7 pages.

Janes, et al., "Targeting KRAS Mutant Cancers with a Covalent G12C-Specific Inhibitor," *Cell*, 172: 578-589 (2018).

Jarvis, "Notorious KRAS: Taking down cancer researchers' biggest foe," *Chemical & Engineering News*, 97(37), 9 pages (2019).

Jin, et al., "Inhibition of AKT survival pathway by a small molecule inhibitor in human endometrial cancer cells," *Br. J. Cancer*, 91: 1808-1812 (2004).

Johnson et al., "Relationships between drug activity in NCI preclinical in vitro and in vivo models and early clinical trials," *British Journal of Cancer*, 84(10): 1424-1431 (2001).

Kojima, "Aiming to Improve the Efficiency of Crystallization Selection in Drug Development", Pharmaceutics, Sep. 1, 2008, vol. 68, No. 5, pp. 344-349 (incl. English translation).

Lanman, et al., "Abstract 4455: Discovery of AMG 510, a first-in-human covalent inhibitor of KRAS$^{G12C}$ for the treatment of solid tumors," Presentation, American Association for Cancer Research (AACR) Annual Meeting, Atlanta, GA, USA, Mar. 29-Apr. 3, 2019.

Lanman, et al., "Abstract 4455: Discovery of AMG 510, a first-in-human covalent inhibitor of KRAS$^{G12C}$ for the treatment of solid tumors," Proceedings of the American Association for Cancer Research Annual Meeting 2019; Mar. 29-Apr. 3, 2019; Atlanta, GA, USA, AACR, *Cancer Res.* 79(13 Suppl): Abstract nr 4455 (2019).

Lanman, et al., "Discovery of a Covalent Inhibitor of KRAS$^{G12C}$ (AMG 510) for the Treatment of Solid Tumors," *J. Med. Chem.*, 63: 52-65 (2020).

Li, et al., "Targeting Protein-Protein Interaction with Covalent Small-Molecule Inhibitors," *Current Topics in Medicinal Chemistry*, 19(21): 1872-1876 (2019).

Lim, et al., "Therapeutic Targeting of Oncogenic K-Ras by a Covalent Catalytic Site Inhibitor," *Angew. Chem. Int. Ed*, 53: 199-204 (2014).

Lipford, et al., "Pre-Clinical Development of AMG 510: The First Inhibitor of KRAS$^{G12C}$ in Clinical Testing," Presentation, American Association for Cancer Research (AACR) Annual Meeting, Atlanta, GA, USA, Mar. 29-Apr. 3, 2019.

Liu, Y., "Session SY28—Transformative Small Molecule Therapies—Targeting KRAS mutant cancers with a covalent G12C—specific inhibitor," Presentation on Apr. 4, 2017, AACR Annual Meeting Presentation, Apr. 1-5, 2017, Washington, D.C. (2017).

Lopez, et al.,"Optimization of quinazolinone-based covalent inhibitors of KRAS$^{G12C}$ in the discovery of AMG 510," Abstract and Poster, ACS Fall Meeting, San Diego, CA, USA, Aug. 25-29, 2019.

Lu, et al., "KRAS G12C Drug Development: Discrimination between Switch II Pocket Configurations Using Hydrogen/Deuterium-Exchange Mass Spectrometry," *Structure*, 25: 1-7 (2017).

Maurer, et al., "Small-molecule ligands bind to a distinct pocket in Rad and inhibit SOS-mediated nucleotide exchange activity," *PNAS*, 109(14): 5299-5304 (2012).

McGregor, et al., "Expanding the Scope of Electrophiles Capable of Targeting K-Ras Oncogenes," *ACS Bio. Chem.*, 56: 3179-3183 (2017).

Meanwell, "Synopsis of Some Recent Tactical Application of Bioisosteres in Drug Design," *J. Med. Chem.* 54:2529-2591 (2011).

Mirati Therapeutics, "Corporate Presentation Nov. 2017," Slides 1-41 (2017).

Modjtahedi, et al., "The human EGF receptor as a target for cancer therapy: six new rat mAbs AGainst the receptor on the breast carcinoma MDA-MB 468," *Br. J. Cancer*, 67(2): 247-253 (1993).

Morrissey et al., "Immunotherapy and Novel Combinations in Oncology: Current Landscape, Challenges, and Opportunities," *Clin. Transl. Sci.*, 9(2):89-104 (2016).

(56) References Cited

OTHER PUBLICATIONS

National Cancer Institute identifier: NSC 154020, retrieved on Nov. 29, 2018, from https://cactus.nci.nih.gov/ncidb2.2/.
NCBI Reference Sequence, "GTPase KRas isoform a [*Homo sapiens*]," GenBank Accession No. NM_203524.1, Retrieved on Nov. 29, 2018 from https://www.ncbi.nlm.nih.gov/protein/15718763?sat=4&satkey=234448549, 4 pages.
Non-Final Office Action (Corrected) for U.S. Appl. No. 16/125,359, mailed Apr. 8, 2019, 13 pages.
Non-Final Office Action for U.S. Appl. No. 15/849,905, mailed Mar. 20, 2019, 18 pages.
Non-Final Office Action for U.S. Appl. No. 15/984,855, mailed Sep. 27, 2018, 25 pages.
Non-Final Office Action for U.S. Appl. No. 16/125,359, mailed Apr. 5, 2019, 13 pages.
Non-Final Office Action for U.S. Appl. No. 16/402,538, mailed Oct. 30, 2019, 12 pages.
Non-Final Office Action for U.S. Appl. No. 16/402,589, mailed Mar. 6, 2020, 17 pages.
Non-Final Office Action for U.S. Appl. No. 16/407,889, mailed Jul. 1, 2020, 6 pages.
Non-Final Office Action for U.S. Appl. No. 16/428,163, mailed Sep. 15, 2020, 6 pages.
Non-Final Office Action for U.S. Appl. No. 16/436,647, mailed Aug. 7, 2020, 19 pages.
Non-Final Office Action for U.S. Appl. No. 16/438,349, mailed Dec. 13, 2019, 15 pages.
Non-Final Office Action for U.S. Appl. No. 16/661,907, mailed Nov. 18, 2019, 20 pages.
Non-Final Office Action for U.S. Appl. No. 16/675,121, mailed Feb. 2, 2021, 10 pages.
Non-Final Office Action for U.S. Appl. No. 16/817,109, mailed Mar. 3, 2021, 12 pages.
Noriyuki, "API Form Screening and Selection at the Drug Discovery Stage", PHARM STAGE, vol. 6, No. 10, Jan. 15, 2007, pp. 20-25 (incl. English translation).
Notice of Allowance, mailed Oct. 20, 2021, for U.S. Appl. No. 16/438,349, 9 pages.
Ostrem, et al., "Development of mutant-specific small molecule inhibitors of K-Ras," Poster, AACR 104th Annual Meeting 2013; Apr. 6-10, 2013; Washington, D.C. (2013).
Ostrem, et al., "K-Ras(G12C) inhibitors allosterically control GTP affinity and effector interactions," *Nature*, 503: 548-551 (2013).
Paez, et al., "*EGFR* Mutations in Lung Cancer Correlation with Clinical Response to Gefitinib Therapy," *Science*, 304(5676): 1497-500 (2004).
Palmioli, et al., "First experimental identification of Ras-inhibitor binding interface using a water-soluble Ras ligand," *Bioorg. Med. Chem. Lett.*, 19: 4217-4222 (2009).
Patricelli, et al., "Selective Inhibition of Oncogenic KRAS Output with Small Molecules Targeting the Inactive State," *Cancer Discov*, 6 (3): 316-329 (2016).
Pearce, et al., "Failure modes in anticancer drug discovery and development," *Cancer Drug Design and Discovery*, Edited by Stephen Neidle, Chapter 18, pp. 424-435 (2008).
Peri, et al., "Design, Synthesis and Biological Evaluation of Sugar-Derived Ras Inhibitors," *ChemBioChem*, 6: 1839-1848 (2005).
Peri, et al., "Sugar-Derived Ras Inhibitors: Group Epitope Mapping by NMR Spectroscopy and Biological Evaluation," *Eur. J. Org. Chem.*, 16: 3707-3720 (2006).
Peters, et al., "Selective inhibition of K-Ras G12C through allosteric control of GTP affinity and effector interactions," EORTC Poster (2013).
PubChem CID 108190520, 2-isopropyl-4-methylpyridin-3-amine, available at https://pubchem.ncbi.nlm.nih.gov/compound/108190520 (last accessed Aug. 30, 2021).
Reck, et al., "CodeBreak 200: A phase 3 multicenter study of sotorasib (AMG 510), a KRAS(G12C) inhibitor, versus docetaxel in patients with previously treated advanced non-small cell lung cancer (NSCLC) harboring KRAS p.G12C mutation," Abstract and Presentation, ESMO Virtual Congress, Sep. 19-21, 2020.
Remington's Pharmaceutical Sciences, 1435-1712 (18th ed., Mack Publishing Co, Easton, Pennsylvania, 1990 (Table of Contents Only).
Rex et al., "KRAS—AACR 2018," Amgen Collection of Information published at Proceedings of the American Association for Cancer Research Annual Meeting 2018; Apr. 14-18, 2018; Chicago, IL; AACR; slides 1-24 (2018).
Rex, et al., "Abstract 3090: In vivo characterization of AMG 510—a potent and selective KRAS$^{G12C}$ covalent small molecule inhibitor in preclinical KRAS$^{G12C}$ cancer models," Poster, American Association for Cancer Research (AACR) Annual Meeting, Atlanta, GA, USA, Mar. 29-Apr. 3, 2019.
Rex, et al., "Abstract 3090: In vivo characterization of AMG 510—a potent and selective KRAS$^{G12C}$ covalent small molecule inhibitor in preclinical KRAS$^{G12C}$ cancer models," Proceedings of the American Association for Cancer Research Annual Meeting 2019; Mar. 29, 2019-Apr 3; Atlanta, GA, USA, AACR, *Cancer Res*. 79(13 Suppl): Abstract nr 3090 (2019).
Saiki, et al., "Abstract 4484: Discovery and in vitro characterization of AMG 510—a potent and selective covalent small-molecule inhibitor of KRAS$^{G12C}$," Presentation, American Association for Cancer Research (AACR) Annual Meeting, Atlanta, GA, USA, Mar. 29-Apr. 3, 2019.
Saiki, et al., "Abstract 4484: Discovery and in vitro characterization of AMG 510—a potent and selective covalent small-molecule inhibitor of KRAS$^{G12C}$," Proceedings of the American Association for Cancer Research Annual Meeting 2019; Mar. 29, 2019-Apr. 3; Atlanta, GA, USA, AACR, *Cancer Res*. 79(13 Suppl): Abstract nr 4484 (2019).
Sarkar, et al., "Indole-3-Carbinol and Prostate Cancer[1,2]," *J. Nutr.*, 134(12 Suppl): 3493S-3498S (2004).
Scharpf, et al., "Comprehensive Pan-Cancer Analyses of RAS Genomic Diversity," Abstract and Presentation, American Association for Cancer Research (AACR) Annual Meeting, Apr. 24-29, 2020.
Shibata et al., "A Convenient Synthesis of 3-Cyano-2-methylpyridines under Ultrasonic Irradiation," *Bull. Chem. Soc. Jpn.*, 61:2199-2200 (1988).
Shima, et al., "In silico discovery of small-molecule Ras inhibitors that display antitumor activity by blocking the Ras—effector interaction," *PNAS*, 110(20): 8182-8187 (2013).
Simone, "Part XIV Oncology: Introduction," *Cecil Textbook of Medicine*, 20$^{th}$ Edition, 1:1004-1010 (1996).
Singh, et al., "Improving Prospects for Targeting RAS," *J. Clinc. Oncl*, 33(31): 3650-3660 (2015).
Spira, et al., "CodeBreak 200: A phase 3 multicenter study of sotorasib (AMG 510), a KRAS(G12C) inhibitor, versus docetaxel in patients with previously treated advanced non-small cell lung cancer (NSCLC) harboring KRAS p.G12C mutation," Presentation, North America Conference on Lung Cancer (NACLC), Virtual Worldwide Event, Oct. 16-17, 2020.
Stanetty et al., "Synthesis of Aza Analogs of the Herbicide Sindone B," *Monatshefte Fuer Chemie*, 130:441-450 (1999).
Statsyuk, "Let K-Ras activate its own inhibitor," *Nature Structural & Molecular Biology*, 25:435-439 (2018).
Strickler, et al., "AMG 510, a novel small molecule inhibitor of KRAS G12C, for patients with advanced gastrointestinal cancers: Results from the CodeBreak 100 phase 1 trial," Abstract and Presentation, World Congress on Gastrointestinal Cancer, Virtual Meeting, Jul. 1-4, 2020 (abstract available as of Jul. 1, 2020).
Sun, et al., "Discovery of Small Molecules that Bind to K-Ras and Inhibit Sos-Mediated Activation," *Angew. Chem. Int. Ed.*, 51: 6140-6143 (2012).
Taveras, et al., "Ras Oncoprotein Inhibitors: The Discovery of Potent, Ras Nucleotide Exchange Inhibitors and the Structural Determination of a Drug-Protein Complex," *Biorg. Med. Chem. Lett.*,, 5(1): 125-133 (1997).
Teramoto, et al., 1996, Cancer 77 (4):639-645.
The ASCO Post Staff, "AACR-NCI-EORTC: Investigational KRAS G12C Inhibitor for KRAS-Mutant Solid Tumors," The ASCO Post (2019).

(56) References Cited

OTHER PUBLICATIONS

Third Party Observation filed for PCT/US2020/033831, submitted Jan. 15, 2021, 2 pages.
Thompson, et al., "PD-1 Is Expressed by Tumor-Infiltrating Immune Cells and Is Associated with Poor Outcome for Patients with Renal Cell Carcinoma," *Clin. Cancer Res.*, 13(6): 1757-1761 (2007).
Traxler, "Tyrosine kinase inhibitors in cancer treatment (Part II)," *Exp. Opin. Ther. Patents*, 8(12): 1599-1625 (1998).
U.S. Appl. No. 60/528,340, filed Dec. 9, 2003.
Wang, et al., "Ras inhibition via direct Ras binding—is there a path forward?," *Bioorg. Med. Chem. Lett.*, 22: 5766-5776 (2012).
Written Opinion for PCT/US2017/067801, mailed Jul. 25, 2018, 10 pages.
Written Opinion for PCT/US2018/033714, mailed Jul. 17, 2018, 5 pages.
Written Opinion for PCT/US2018/050044, mailed Oct. 30, 2018, 7 pages.
Written Opinion for PCT/US2019/030593, mailed Aug. 6, 2019, 5 pages.
Written Opinion for PCT/US2019/030606, mailed Jul. 23, 2019, 6 pages.
Written Opinion for PCT/US2019/031535, mailed Jul. 25, 2019, 7 pages.
Written Opinion for PCT/US2019/034974, mailed Aug. 9, 2019, 5 pages.
Written Opinion for PCT/US2019/036397, mailed Aug. 26, 2019, 5 pages.
Written Opinion for PCT/US2019/036626, mailed Jun. 2, 2020, 12 pages.
Written Opinion for PCT/US2019/061815, mailed Mar. 5, 2020, 4 pages.
Written Opinion for PCT/US2019/062051, mailed Mar. 2, 2020, 5 pages.
Written Opinion for PCT/US2019/62064, mailed Oct. 29, 2020, 14 pages.
Written Opinion for PCT/US2020/032686, mailed Aug. 14, 2020, 6 pages.
Written Opinion for PCT/US2020/033831, mailed Jul. 9, 2020, 7 pages.
Written Opinion for PCT/US2020/033832, mailed Jul. 8, 2020, 6 pages.
Written Opinion for PCT/US2020/056874, mailed Feb. 12, 2021, 10 pages.
Written Opinion for PCT/US2020/060415, mailed Feb. 3, 2021, 9 pages.
Written Opinion for PCT/US2020/065050, mailed Mar. 29, 2021, 8 pages.
Xiong, et al., "Covalent Guanosine Mimetic Inhibitors of G12C KRAS," *ACS Med. Chem. Lett.*, 8: 61-66 (2017).
Yan, et al., "Pharmacogenetics and pharmacogenomics in oncology therapeutic antibody development," *BioTechniques*, 29(4): 565-568 (2005).
Yang, et al., "Akt/Protein Kinase B Signaling Inhibitor-2, a Selective Small Molecule Inhibitor of Akt Signaling with Antitumor Activity in Cancer Cells Overexpressing Akt," *Cancer Res.*, 64, 4394-4399 (2004).
Yang, et al., "Eradication of Established Tumors by a Fully Human Monoclonal Antibody to the Epidermal Growth Factor Receptor without Concomitant Chemotherapy," *Cancer Res.*, 59: 1236-1243 (1999).
Zeng, et al., "Potent and Selective Covalent Quinazoline Inhibitors of KRAS G12C," *Cell Chemical Biology*, 24: 1-12 (2017).
Zimmerman, et al., "Small molecule inhibition of the KRAS-PDEδ interaction impairs oncogenic KRAS signaling," *Nature*, 1-5 (2017).
Examiner-Initiated Interview Summary, mailed Dec. 9, 2021, for U.S. Appl. No. 16/817,109, 1 page.
International Search Report for PCT/US2020/060421, mailed Feb. 18, 2021, 4 pages.
Non-Final Office Action for U.S. Appl. No. 15/930,606, mailed Jan. 13, 2022, 4 pages.
Notice of Allowance, mailed Dec. 9, 2021, for U.S. Appl. No. 16/685,841, 8 pages.
Notice of Allowance, mailed Dec. 9, 2021, for U.S. Appl. No. 16/817,109, 9 pages.
Notice of Allowance, mailed Nov. 1, 2021, for U.S. Appl. No. 16/675,121, 7 pages.
Office Communication (Ex Parte Quayle) for U.S. Appl. No. 16/687,563, mailed Jan. 14, 2022, 5 pages.
Written Opinion for PCT/US2020/060421, mailed Feb. 18, 2021, 5 pages.
Brauswetter et al., "Molecular subtype specific efficacy of MEK inhibitors in pancreatic cancers," PLOS ONE, 12(9): e0185687 (pp. 1-13) (2017).
Dimartino et al., "Preparation and Physical Characterization of Forms II and III of Paracetamol," *Journal of Thermal Analysis*, 48:447-458 (1997).
Knapman, "Polymorphic Predictions: Understanding the nature of crystalline compounds can be critical in drug development and manufacture", *Modern Drug Discovery*, 53-57 (2000).
Communication Pursuant to Rule 114(2) EPC, Third Party Observation, European Patent Application No. 21183032.8, Apr. 3, 202, 6 pages.
Non-Final Office Action for U.S. Appl. No. 17/031,607, mailed Mar. 31, 2023, 7 pages.
Non-Final Office Action for U.S. Appl. No. 17/692,026, mailed May 11, 2023, 17 pages.
Notice of Allowance, mailed Mar. 29, 2023, for U.S. Appl. No. 17/363,878, 8 pages.
Yang et al., "Docetaxel and Cisplatin regimen for non-small-cell lung cancer," Hosp. Pharm. 48(7):550-557 (2013).
Yang et al., "Effect of dose adjustment on the safety and efficacy of afatinib for EGFR mutation-positive lung adenocarcinoma: post hoc analyses of the randomized LUX-Lung 3 and 6 trials," Ann. Oncol. 27(11):2103-2110 (2016).
"A Phase 1, Study Evaluating the Safety, Tolerability, PK, and Efficacy of AMG 510 in Subjects With Solid Tumors With a S Mutation." NCT03600883, Version 4, submitted Oct. 29, 2018, posted Oct. 31, 2018, 16 pages.
Communication Pursuant to Rule 114(2) EPC, Third Party Observation, European Patent Application No. 21183032.8, Dec. 19, 2023, 11 pages.
Lee, "A practical guide to pharmaceutical polymorph screening & selection." *Asian Journal of Pharmaceutical Sciences* 9(4):163-175 (2014).
Non-Final Office Action for U.S. Appl. No. 17/579,359, mailed Dec. 14, 2023, 13 pages.
Notice of Allowance for U.S. Appl. No. 17/553,598, mailed Aug. 9, 2023, 5 pages.
Notice of Allowance, mailed Jan. 22, 2024, for U.S. Appl. No. 17/692,026, 9 pages.
Notice of Allowance, mailed Oct. 20, 2023, for U.S. Appl. No. 17/870,573, 7 pages.
Notice of Allowance, mailed Oct. 3, 2023, for U.S. Appl. No. 17/031,607, 7 pages.
Brittain et al. (Editor), "Polymorphism in Pharmaceutical Solids," 2nd Edition, DOI https://doi.org/10.3109/9781420073225, ebook ISBN 9780429147661, CRC Press, Boca Raton, Nov. 11, 2018.
Censi and DiMartino. "Polymorph Impact on the Bioavailability and Stability of Poorly Soluble Drugs," Molecules 20(10):18759-18776 (2015).
Non-Final Office Action for U.S. Appl. No. 18/213,464, mailed Nov. 13, 2024, 13 pages.
Non-Final Office Action for U.S. Appl. No. 18/422,704, mailed Oct. 10, 2024, 8 pages.
Yu, "Amorphous pharmaceutical solids: preparation, characterization and stabilization," Advanced Drug Delivery Reviews, 48:27-42 (2001).

* cited by examiner

SOLID STATE FORMS

CROSS REFERENCES TO RELATED APPLICATIONS

This application is a continuation of U.S. patent application Ser. No. 17/553,598, filed Dec. 16, 2021, which is a continuation of U.S. patent application Ser. No. 16/878,824, filed May 20, 2020, now U.S. Pat. No. 11,236,091, which claims the benefit of U.S. Provisional Application No. 62/851,044, filed on May 21, 2019, all of which are incorporated herein by reference in their entireties for all purposes.

FIELD

The present disclosure provides a crystalline form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, (hereinafter "Compound 1"), including several crystalline forms of an anhydrous form, a hydrate form, several solvate forms, and physical forms thereof, pharmaceutical compositions, and a method of treating a disease mediated by KRAS G12C inhibition.

BACKGROUND

Compound 1 is a selective inhibitor of KRAS G12C useful for the treatment of cancers, including treatment of lung cancer, such as non-small cell lung cancer (NSCLC), pancreatic cancer, and colorectal cancer. U.S. Patent Application Publication Number 2018/0334454A1, published on Nov. 22, 2018, discloses Compound 1.

Many compounds can exist in different crystal forms, or polymorphs, which exhibit different physical, chemical, and spectroscopic properties. For example, certain polymorphs of a compound may be more readily soluble in particular solvents, may flow more readily, or may compress more easily than others. See, e.g., P. DiMartino, et al., *J. Thermal. Anal.*, 48:447-458 (1997). In the case of drugs, certain solid forms may be more bioavailable than others, while others may be more stable under certain manufacturing, storage, and biological conditions. This is particularly important from a regulatory standpoint, since drugs are approved by agencies such as the U.S. Food and Drug Administration only if they meet exacting purity and characterization standards. Indeed, the regulatory approval of one polymorph of a compound, which exhibits certain solubility and physicochemical (including spectroscopic) properties, typically does not imply the ready approval of other polymorphs of that same compound.

Polymorphic forms of a compound are known in the pharmaceutical arts to affect, for example, the solubility, stability, flowability, fractability, and compressibility of the compound, as well as the safety and efficacy of drug products comprising it. See, e.g., Knapman, K. *Modern Drug Discoveries*, 2000, 53. Therefore, the discovery of new polymorphs of a drug can provide a variety of advantages.

The present disclosure provides new polymorphic forms of Compound 1, including several crystalline forms of an anhydrous form, a hydrate form, several solvate forms, and physical forms thereof, pharmaceutical compositions, and a method of treating a disease mediated by KRAS G12C inhibition. The new polymorphic forms can further the development of formulations for the treatment of these chronic illnesses, and may yield numerous formulation, manufacturing and therapeutic benefits.

SUMMARY

The present disclosure provides crystalline and amorphous forms of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, including several anhydrous, hydrate and solvate forms, and solid state forms thereof, pharmaceutical compositions, and methods of treating a disease mediated by KRAS G12C inhibition.

DETAILED DESCRIPTION

Definitions

Figure 1:
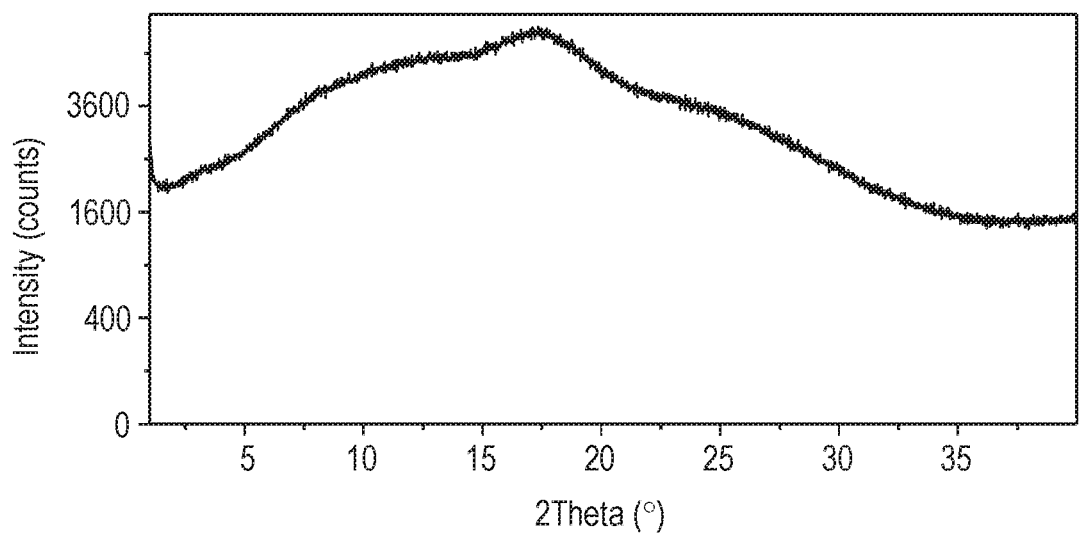
FIG. 1 shows XRPD data for an amorphous form of Compound 1. The powder X-ray pattern is characteristic of amorphous material with a broad amorphous halo and no distinct compound related diffraction peaks from 5-40° 2-theta.
Figure 2:
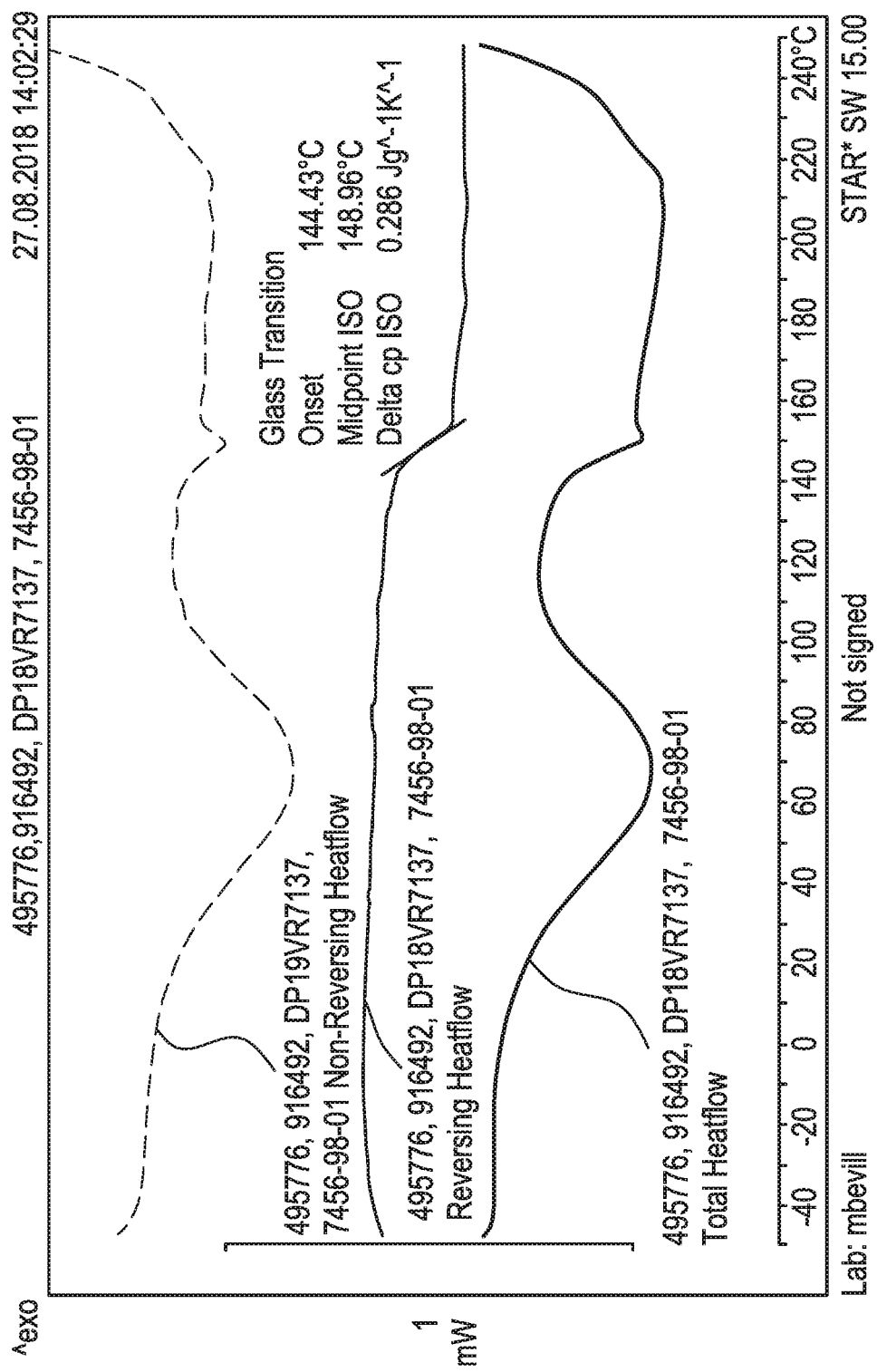
FIG. 2 shows DSC data for an amorphous form of Compound 1.
Figure 3:
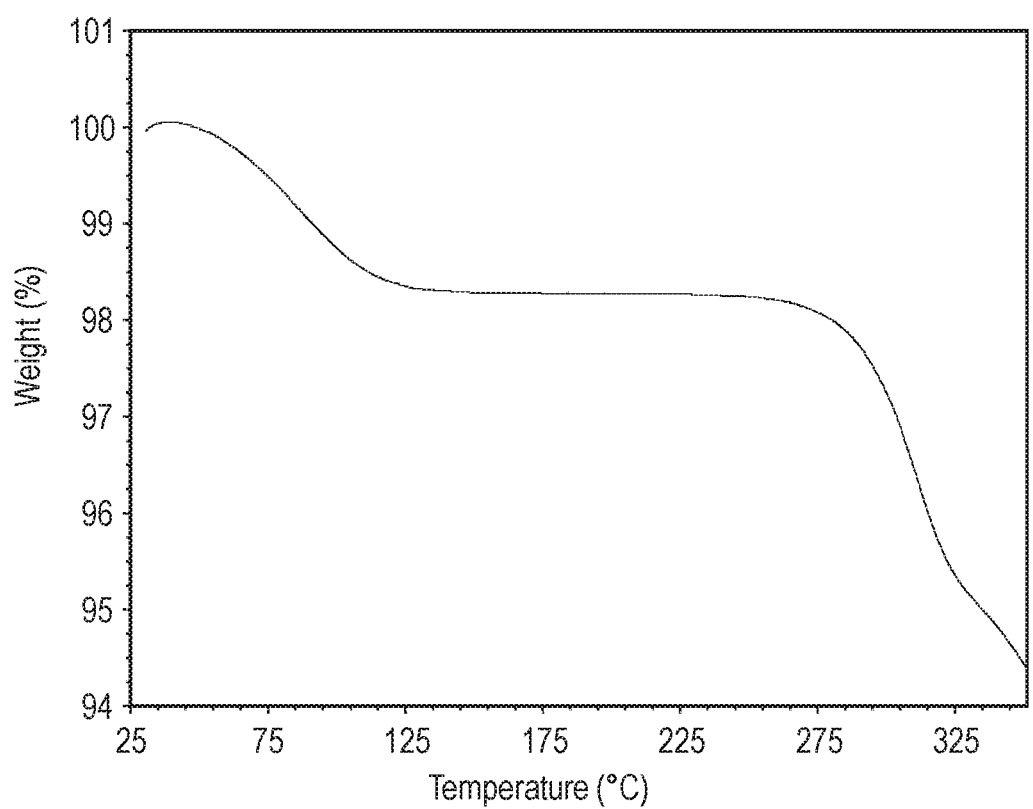
FIG. 3 shows TGA data for an amorphous form of Compound 1.

The term "Compound 1" means 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one.

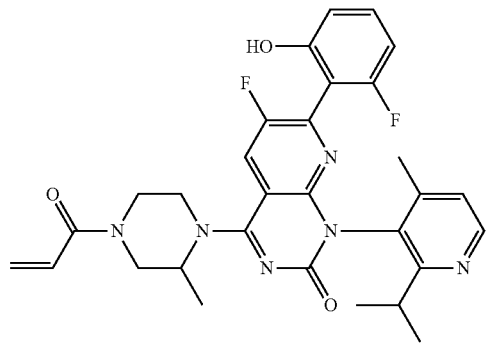

Chemical Formula: $C_{30}H_{30}F_2N_6O_3$
Exact Mass: 560.23
Molecular Weight: 560.61
Elemental Analysis: C, 64.28; H, 5.39; F, 6.78; N, 14.99; O, 8.56

Certain of the compounds disclosed herein may exist as atropisomers, which are conformational stereoisomers that occur when rotation about a single bond in the molecule is prevented, or greatly slowed, as a result of steric interactions with other parts of the molecule. The compounds disclosed herein include all atropisomers, both as pure individual atropisomer preparations, enriched preparations of each, or a non-specific mixture of each. Where the rotational barrier about the single bond is high enough, and interconversion between conformations is slow enough, separation and isolation of the isomeric species may be permitted.

For example, Compound 1 is

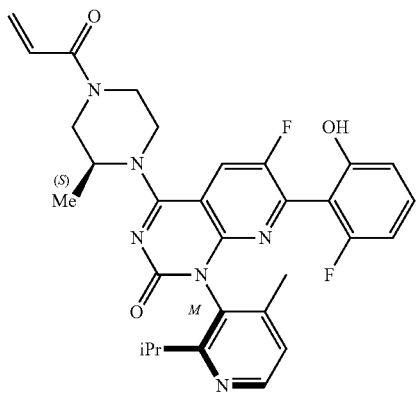

atropisomer M and may exhibit restricted rotation. The M-atropisomer of Compound 1 is also known as AMG 510. Canon, J., et al., Nature 575(7781):217-223 (2019), FIG. 1a.

Alternatively, Compound 1 has the following atropisomer P and may exhibit restricted rotation.

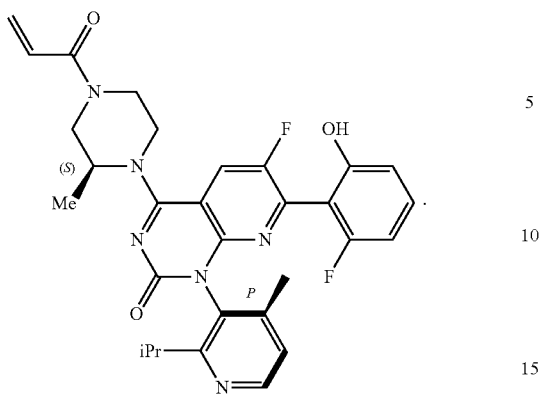

Abbreviations: The following abbreviations may be used herein:

| | |
|---|---|
| AcOH | acetic acid |
| aq or aq. | aqueous |
| DCM | dichloromethane |
| DME | 1,2-dimethoxyethane |
| DMF | N,N-dimethylformamide |
| DMSO | dimethyl sulfoxide |
| eq or eq. or equiv. | equivalent |
| ESI or ES | electrospray ionization |
| Et | ethyl |
| Et$_2$O | diethyl ether |
| EtOAc | ethyl acetate |
| EtOH | ethanol |
| g | gram(s) |
| h | hour(s) |
| HPLC | high pressure liquid chromatography |
| IPA | Isopropyl alcohol |
| iPI | isopropyl |
| iPr$_2$NEt or DIPEA | N-ethyl diisopropylamine (Hünig's base) |
| LC MS, LCMS, LC-MS or LC/MS | liquid chromatography mass spectroscopy |
| LG | leaving group (e.g., halogen, mesylate, triflate) |
| m/z | mass divided by charge |
| Me | methyl |
| MeCN | acetonitrile |
| MeOH | Methanol |
| MEK | Methyl ethyl ketone |
| Met | metal species for cross-coupling (e.g., MgX, ZnX, SnR$_3$, SiR$_3$, B(OR)$_2$) |
| mg | milligrams |
| min | minutes |
| mL | milliliters |
| MS | mass spectra |
| NaHMDS | sodium hexamethyldisilazide |
| NBS | N-bromosuccinimide |
| n-BuLi | n-butyllithium |
| NCS | N-chlorosuccinimide |
| NMR | nuclear magnetic resonance |
| Pd$_2$(dba)$_3$ | tris(dibenzylideneacetone)dipalladium(0) |
| Pd(dppf)Cl$_2$•DCM, Pd(dppf)Cl$_2$ | [1,1'-bis(diphenylphosphino)ferrocene]dichloropalladium(II), complex with dichloromethane |
| Pd(PPh$_3$)$_4$ | tetrakis(triphenylphosphine)palladium(0) |
| Ph | phenyl |
| ppm | parts per million |
| PR or PG or Prot. group | protecting group |
| rbf | round-bottomed flask |
| RP-HPLC | reverse phase high pressure liquid chromatography |
| RT or rt or r.t. | room temperature |
| sat. or satd. | saturated |
| SFC | supercritical fluid chromatography |
| SPhos Pd G3 or SPhos G3 | (2-dicyclohexylphosphino-2',6'-dimethoxybiphenyl) [2-(2'-amino-1,1'-biphenyl)]palladium(II) methanesulfonate |
| SSNMR | Solid state nuclear magnetic resonance |
| TBAF | tetra-n-butylammonium fluoride |
| TBTU | N,N,N',N'-tetramethyl-O-(benzotriazol-1-yl)uronium |

| | |
|---|---|
| | tetrafluoroborate |
| t-BuOH | tert-butanol |
| TEA or Et₃N | trimethylamine |
| TFA | trifluoroacetic acid |
| THF | tetrahydrofuran |
| UV | ultraviolet |

The use of the terms "a," "an," "the," and similar referents in the context of the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

The term "anhydrous form of Compound 1" means a form of Compound 1 substantially or completely free from water and particularly water of crystallization. Those skilled in the art appreciate that the exact number of water molecules may vary slightly at any time with variable temperature, pressure, and other environmental influences. All slight variations of the number of the associated water molecules are contemplated to be within the scope of the present disclosure.

The term "co-crystal" means a crystalline material comprising two or more compounds at ambient temperature (20° C. to 25° C., preferably 20° C.), of which at least two are held together by weak interaction, wherein at least one of the compounds is a co-crystal former and the other is Compound 1. Weak interaction is being defined as an interaction which is neither ionic nor covalent and includes for example: hydrogen bonds, van der Waals forces, and π-π interactions. The term "co-crystal" includes solvate forms.

The term "amorphous form" or "amorphous" means a material that lacks long range order and as such does not show distinct X-ray diffraction peaks, i.e. a Bragg diffraction peak. The XRPD pattern of an amorphous material is characterized by one or more amorphous halos.

The term "amorphous halo" is an approximately bell-shaped maximum in the X-ray powder pattern of an amorphous substance.

The term "excipient" means any pharmaceutically acceptable additive, carrier, diluent, adjuvant, or other ingredient, other than the active pharmaceutical ingredient (API), which is typically included for formulation and/or administration to a patient.

The term "a disease mediated by KRAS G12C inhibition" means (i) cancers and (ii) solid tumors. KRAS is the most frequently mutated oncogene in cancer and encodes a key signalling protein in tumors. Canon, J., et al., *Nature* 575 (7781):217-223 (2019), abstract. The KRAS(G12C) mutant has a cysteine residue that has been exploited to design covalent inhibitors that have promising preclinical activity. Id. A series of inhibitors was optimized, using novel binding interactions to markedly enhance their potency and selectivity. Id. The efforts have led to the discovery of AMG 510. Id. In preclinical analyses, treatment with AMG 510 led to the regression of $KRAS^{G12C}$ tumors and improved the anti-tumor efficacy of chemotherapy and targeted agents. Id. In immune-competent mice, treatment with AMG 510 resulted in a pro-inflammatory tumor microenvironment and produced durable cures alone as well as in combination with immune-checkpoint inhibitors. Id. Cured mice rejected the growth of isogenic $KRAS^{G12D}$ tumors, which suggests adaptive immunity against shared antigens. Id. Furthermore, in clinical trials, AMG 510 demonstrated anti-tumor activity in the first dosing cohorts and represents a potentially transformative therapy for patients for whom effective treatments are lacking. Id.

The term "cancer" means a hyperproliferative disorder in a mammal, such as a human, with a KRAS, HRAS or NRAS G12C mutation, which can be treated by, for example, by administering to said mammal a therapeutically effective amount of Compound 1 as disclosed herein. In some embodiments, the cancer is, for example, acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urachal cancer, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e.g., psoriasis), restenosis, or prostate (e. g., benign prostatic hypertrophy (BPH)).

The term "patient" means animals, such as dogs, cats, cows, horses, sheep and humans. Particular patients are mammals. The term patient includes males and females.

The term "therapeutically effective amount" means an amount of a compound that ameliorates, attenuates or eliminates one or more symptom of a particular disease or condition, or prevents or delays the onset of one of more symptoms of a particular disease or condition.

The term "pharmaceutically acceptable" means that the referenced substance, such as a compound of the present disclosure or a formulation containing a compound of the present disclosure, or a particular excipient, are suitable for administration to a patient.

As used herein and unless otherwise indicated, the terms "polymorph" and "polymorphic form" refer to solid crystalline forms of a compound or complex. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

Polymorphs of a molecule can be obtained by a number of methods known in the art. Such methods include, but are not limited to, melt recrystallization, melt cooling, solvent recrystallization, desolvation, rapid evaporation, rapid cooling, slow cooling, vapor diffusion and sublimation. Polymorphs can be detected, identified, classified and characterized using well-known techniques such as, but not limited to, differential scanning calorimetry (DSC), thermogravimetry (TGA), X-ray powder diffractometry (XRPD), single crystal X-ray diffractometry, vibrational spectroscopy, solution calorimetry, solid state nuclear magnetic resonance (NMR), infrared (IR) spectroscopy, Raman spectroscopy, hot stage optical microscopy, scanning electron microscopy (SEM), electron crystallography and quantitative analysis, particle size analysis (PSA), surface area analysis, solubility, and rate of dissolution.

As used herein to refer to the spectra or data presented in graphical form (e.g., XRPD, IR, Raman and NMR spectra), and unless otherwise indicated, the term "peak" refers to a peak or other special feature that one skilled in the art would recognize as not attributable to background noise.

As used herein and unless otherwise indicated, the term "substantially pure" when used to describe a polymorph of a compound means a solid form of the compound that comprises that polymorph and is substantially free of other polymorphs of the compound. A representative substantially pure polymorph comprises greater than about 80% by weight of one polymorphic form of the compound and less than about 20% by weight of other polymorphic forms of the compound, more preferably greater than about 90% by weight of one polymorphic form of the compound and less than about 10% by weight of the other polymorphic forms of the compound, even more preferably greater than about 95% by weight of one polymorphic form of the compound and less than about 5% by weight of the other polymorphic forms of the compound, and most preferably greater than about 97% by weight of one polymorphic forms of the compound and less than about 3% by weight of the other polymorphic forms of the compound.

The terms "treating", "treat" or "treatment" and the like include preventative (e.g., prophylactic) and palliative treatment.

The term "variable hydrate" means a hydrate of Compound 1 having at least about one, two, three, or four associated water molecules. In some embodiments, the hydrates of the present disclosure include from at least one to ten associated molecules of water. Those skilled in the art appreciate that the exact number of the associated water molecules may vary slightly at any time with variable temperature, pressure, and other environmental influence. All slight variations of the number of the associated water molecules are contemplated to be within the scope of the present disclosure.

In some embodiments, the methods for treatment are directed to treating lung cancers, the methods comprise administering an effective amount of any of the above described compounds (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In some embodiments, the lung cancer is a small cell lung carcinoma. Other lung cancers treatable with the disclosed compounds include, but are not limited to, glandular tumors, carcinoid tumors and undifferentiated carcinomas. In one embodiment the NSCLC is locally advanced or metastatic.

The compounds of the present disclosure are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present disclosure can be administered alone, in combination with other compounds of the present disclosure, or with other pharmaceutically active compounds. The other pharmaceutically active compounds can be intended to treat the same disease or condition as the compounds of the present disclosure or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

It is also noted that the solid state forms of the present disclosure can be administered together. For example, substantially pure crystalline anhydrous form I of Compound 1 can be administered to a patient. Alternatively, about 90% by weight of crystalline anhydrous form I of Compound 1 can be administered with the remaining Compound 1 present in other forms, such as the amorphous form of Compound I. In another embodiment, 80% by weight of crystalline anhydrous form I of Compound 1 can be administered with the remaining Compound 1 present in other forms, such as the amorphous form. All combinations are contemplated. In one embodiment of the disclosure, Compound 1 is administered to a patient in one substantially pure form. Those skilled in the art will appreciate the possible variations.

The compounds of the present disclosure may be used in the manufacture of a medicament for the treatment of a disease mediated by KRAS G12C inhibition, such as cancer, including but not limited to colorectal cancer, pancreatic cancer and lung cancer, such as non-small cell lung cancer (NSCLC).

In still a further aspect, the disclosure relates to the use of a salt, a crystalline form, an amorphous form, or co-crystal of Compound 1 for the preparation of a medicament useful for treating cancer, such as colorectal cancer, pancreatic cancer and lung cancer, such as non-small cell lung cancer (NSCLC).

Since one aspect of the present disclosure contemplates the treatment of the disease/conditions with a combination of pharmaceutically active compounds that may be administered separately, the disclosure further relates to combining separate pharmaceutical compositions in kit form. The kit comprises two separate pharmaceutical compositions: a compound of the present disclosure, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present disclosure can consist of one tablet or capsule, while a daily dose of the second compound can consist of several tablets or capsules and vice versa. The memory aid should reflect this and aid in correct administration of the active agents.

In another specific embodiment of the disclosure, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present disclosure and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated. In one embodiment, the compounds of the present disclosure and other pharmaceutically active compounds, if desired, can be administered to a patient orally.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. In one embodiment the dosage form contemplated in this disclosure is a solid dosage for, such as a tablet for oral administration.

Solid compositions of a similar type may also be used as fillers in hard filled gelatin capsules using such excipients as lactose, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs, for example in a soft filled gelatin capsules. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present disclosure include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this disclosure.

The compounds of the present disclosure can be administered to a patient at dosage levels in the range of about 0.1 to about 2000 mg per day, preferably from 5 mg to 1000 mg per day. For a normal adult human having a body weight of about 70 kg, a dosage in the range of about 0.001 mg per kilogram body weight to about 20 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art. In one embodiment the total daily dose administered to a patient is 180 mg, 360 mg, 720 mg, or 960 mg. The total daily dose can be administered orally with multiple tablets containing, e.g., 120 mg of Compound 1 (e.g., the total daily dose of 960 mg is administered with 8 tablets of 120 mg of Compound 1 each). In one embodiment the total daily dose administered to a patient is 960 mg of Compound 1. In one embodiment the total daily dose of 960 mg of Compound 1 is administered with 8 tablets comprising 120 mg of Compound 1.

Unless specifically stated otherwise, the compounds of the present disclosure may exist in unsolvated as well as solvated forms with pharmaceutically acceptable solvents such as water (hydrate), ethanol, and the like. The present disclosure contemplates and encompasses both the solvated and unsolvated forms.

It is also possible that compounds of the present disclosure may exist in different tautomeric forms. All tautomers of compounds of the present disclosure are contemplated. For example, all keto-enol forms of the compounds are included in this disclosure.

Those skilled in the art will recognize that the compound names and structures contained herein may be based on a particular tautomer of a compound. While the name or structure for only a particular tautomer may be used, it is intended that all tautomers are encompassed by the present disclosure, unless stated otherwise.

Those skilled in the art will understand that the anhydrous free forms, hydrates, salts and co-crystals of Compound 1 may exist in one or more ionization states. which typically exists as zwitterions. While the name or structure for only a particular ionization state may be used, it is intended that all ionization states are encompassed by the present disclosure, unless stated otherwise.

It is also intended that the present disclosure encompasses compounds that are synthesized in vitro using laboratory techniques, such as those well known to synthetic chemists; or synthesized using in vivo techniques, such as through metabolism, fermentation, digestion, and the like. It is also contemplated that the compounds of the present disclosure may be synthesized using a combination of in vitro and in vivo techniques.

The present disclosure also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{31}$P, $^{32}$P, $^{35}$S, $^{18}$F, and $^{36}$Cl.

Compounds of the present disclosure that contain the aforementioned isotopes and/or other isotopes of other atoms are within the scope of this disclosure. Certain isotopically-labelled compounds of the present disclosure, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this disclosure can generally be prepared by substituting a readily available isotopically labelled reagent for a non-isotopically labelled reagent.

All patents and other publications recited herein are hereby incorporated by reference.

The examples and embodiments presented below are illustrative of the invention disclosed herein and are not intended to limit the scope of the claims in any manner.

EMBODIMENTS

1. In one embodiment, the present invent provides a crystalline anhydrous form I of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1).

2. In another embodiment, the present disclosure provides the crystalline anhydrous form I of embodiment 1, wherein the anhydrous form I is the M atropisomer.

Figure 5:
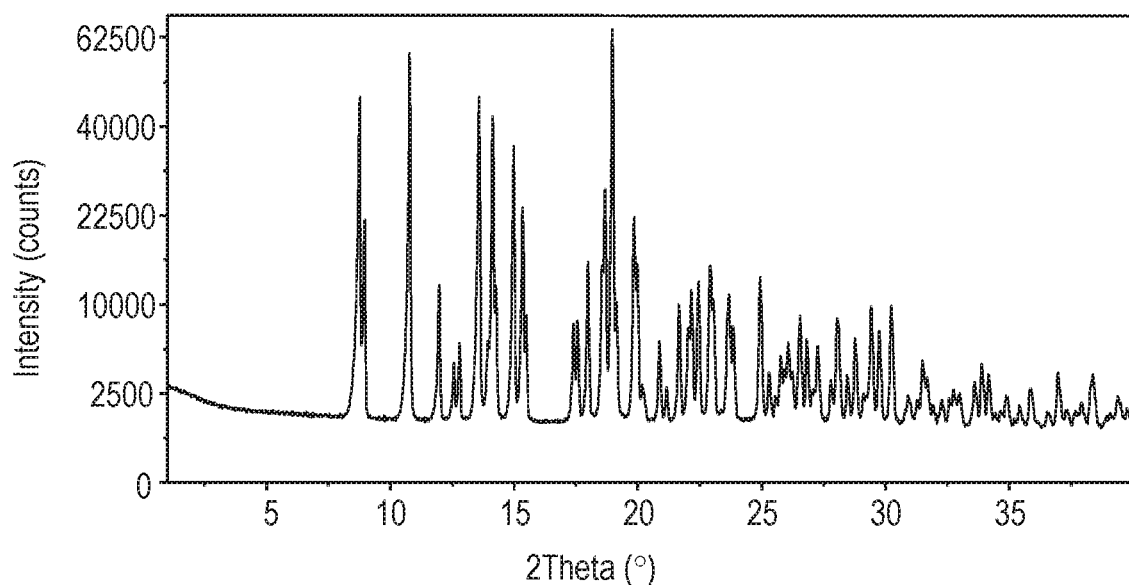
FIG. 5 shows XRPD data for the crystalline anhydrous form I of Compound 1. The powder X-ray diffraction pattern of the anhydrous forms I-III of Compound 1 is characteristic of crystalline material with distinct diffraction peaks between 3° 2-theta to 40° 2-theta.

3. In another embodiment, the present disclosure provides the crystalline anhydrous form I of embodiment 1, wherein the crystalline anhydrous form I is characterized by the powder X-ray diffraction pattern substantially as shown in FIG. 5.

4. In another embodiment, the present disclosure provides the crystalline anhydrous form I of embodiment 1, wherein said crystalline anhydrous form I is characterized by at least three peaks, at least five peaks, or at least seven peaks selected from a powder X-ray diffraction pattern comprising peaks at diffraction angle 2 theta degrees at approximately 8.8, 9.0, 10.8, 12.0, 12.6, 12.8, 13.6, 14.2, 15.0, 15.4, 18.0, 18.6, 18.7, 19.0, 19.9, 20.0, 22.9, and 25.0.

5. In another embodiment, the present disclosure provides the crystalline anhydrous form I of embodiment 1, wherein said crystalline anhydrous form I is characterized by a powder X-ray diffraction pattern comprising peaks at diffraction angle 2 theta degrees at approximately 9.0, 12.0, 12.6 and 19.0.

6. In another embodiment, the present disclosure provides the crystalline anhydrous form I of embodiment 1 having a differential scanning calorimetry thermogram comprising an endotherm with an onset of about 293° C.

7. In another embodiment, the present disclosure provides the crystalline anhydrous form of embodiment 1 having a thermogravimetric analysis thermogram comprising a weight loss of about 0.2% when heated from about 25° C. to about 275° C.

Figure 8:
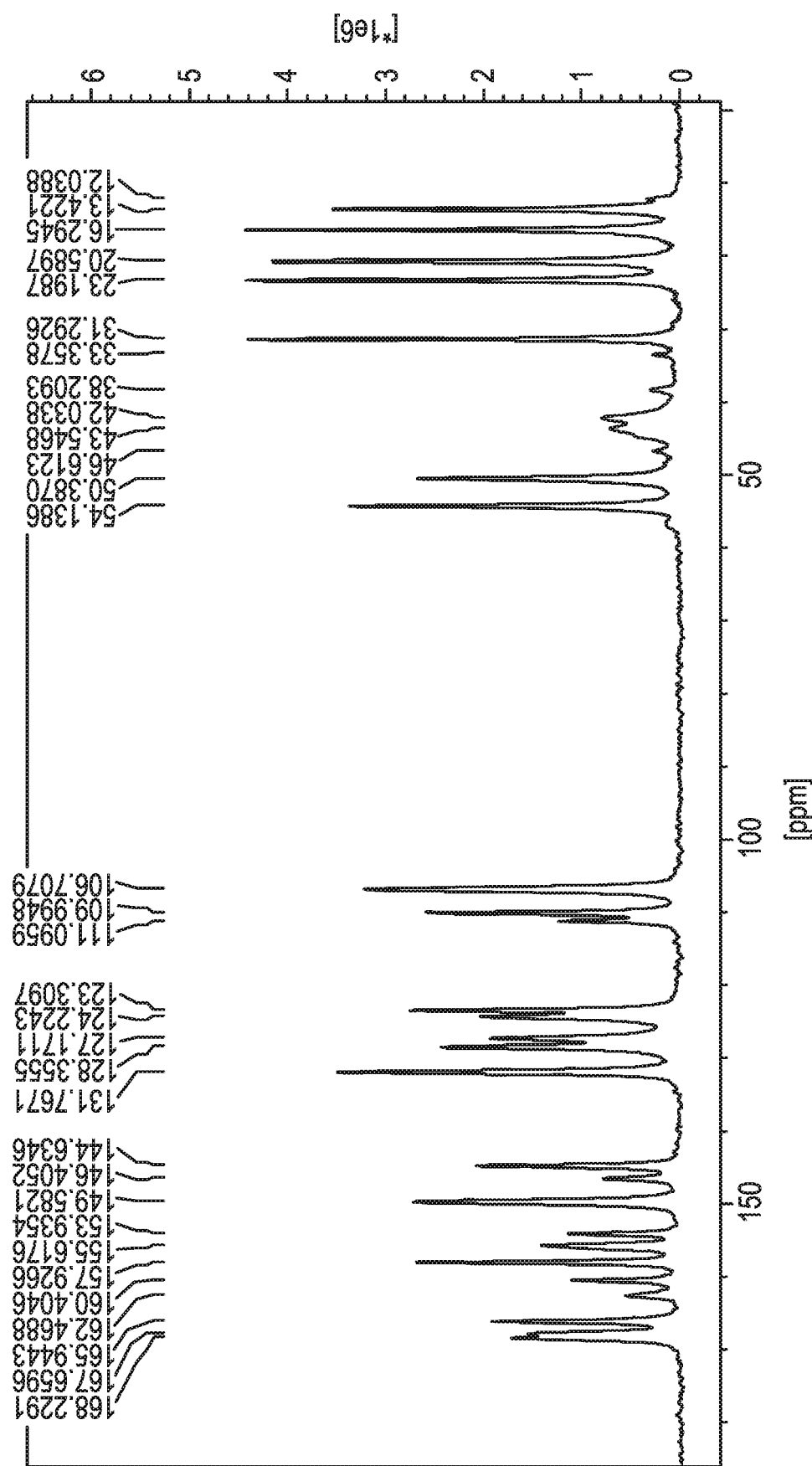
FIG. 8 shows $^{13}$C SSNMR data for crystalline anhydrous form I of Compound 1.

8. In another embodiment, the present disclosure provides the crystalline anhydrous form of embodiment 1, wherein said crystalline anhydrous form I is characterized by $^{13}$C solid state NMR as depicted in FIG. 8.

9. In another embodiment, the present disclosure provides the crystalline anhydrous form of embodiment 1, wherein said crystalline anhydrous form I is characterized by $^{13}$C solid state NMR, comprising peaks at approximately 12, 13, 16, 21, 23, 31, 33, 38, 42, 44, 47, 50, 54, 107, 110, 111, 123, 124, 127, 128, 132, 145, 146, 150, 154, 156, 158, 160, 162, 166, 167.7 and 168 ppm.

Figure 9:
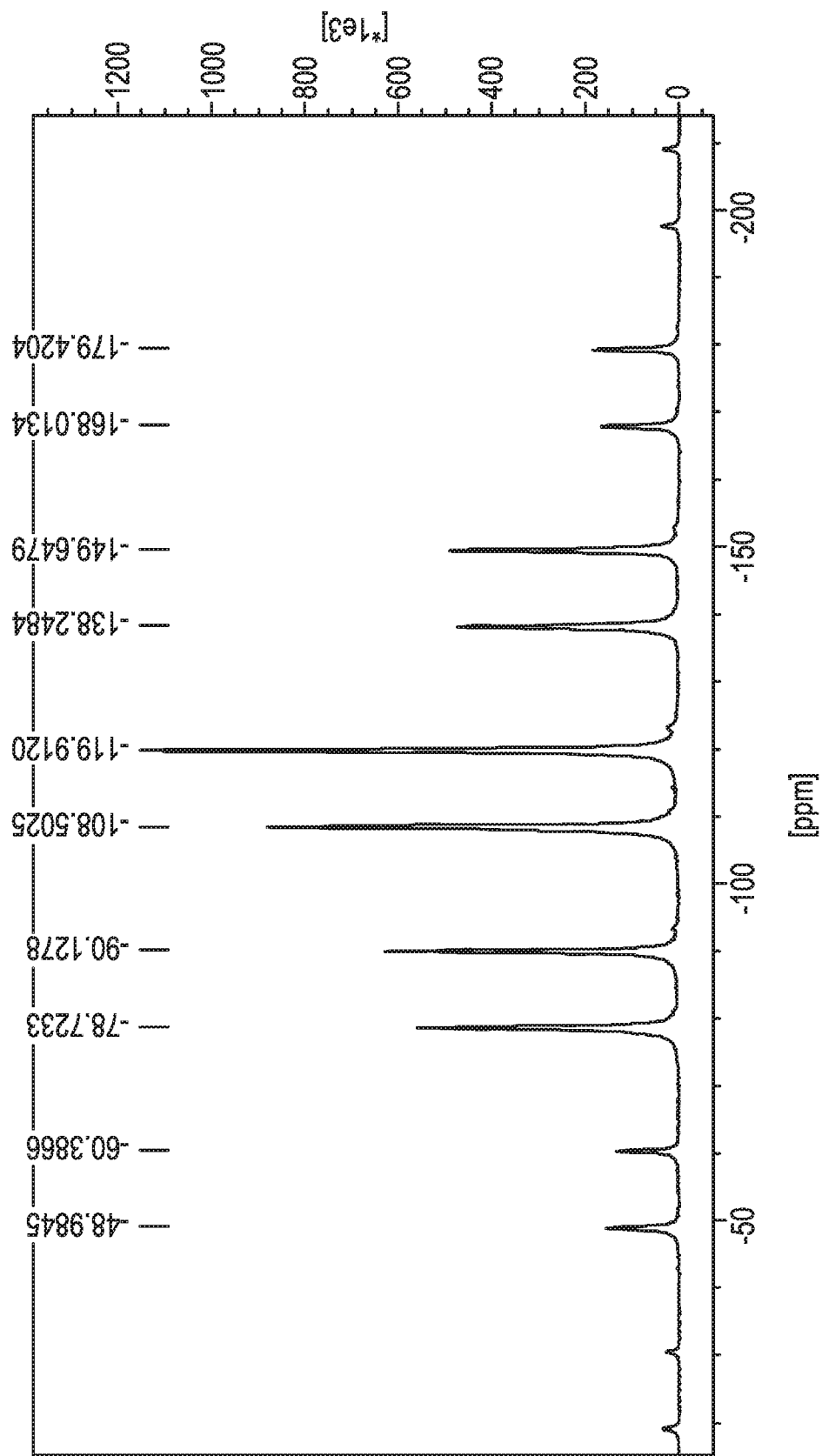
FIG. 9 shows $^{19}$F SSNMR data for crystalline anhydrous form I of Compound 1.

10. In another embodiment, the present disclosure provides the crystalline anhydrous form of embodiment 1, wherein said crystalline anhydrous form I is characterized by $^{19}$F solid state NMR as depicted in FIG. 9.

11. In another embodiment, the present disclosure provides the crystalline anhydrous form of embodiment 1, wherein said crystalline anhydrous form I is characterized by $^{19}$F solid state NMR, comprising peaks at approximately −49, −60, −79, −90, −109, −120, −138, −150, −168 and −179 ppm.

12. In another embodiment, the present disclosure provides the crystalline anhydrous form of embodiment 1 which is substantially pure.

13. In another embodiment, the present disclosure provides a pharmaceutical composition comprising the crystalline anhydrous form I of embodiment 1, and a pharmaceutically acceptable excipient.

14. In another embodiment, the present disclosure provides the pharmaceutical composition comprising the crystalline anhydrous form I as in any one of embodiments 1, 2, 3, 4, 5, 6, 7, 8, 9, 10, 11, 12 or 13, or a mixture thereof, and a pharmaceutically acceptable excipient.

15. In another embodiment, the present disclosure provides the pharmaceutical composition of embodiment 14, wherein the composition is a single dose.

16. In another embodiment, the present disclosure provides a composition comprising an amorphous form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one and the crystalline anhydrous form I of embodiment 1.

17. In another embodiment, the present disclosure provides a method for preparing the crystalline anhydrous form I of embodiment 1, the method comprising: combining form II of Compound 1 and a suitable solvent, and removing the solvent to form a crystalline anhydrous form I of Compound 1.

18. In another embodiment, the present disclosure provides the method of embodiment 17, wherein the suitable solvent is water.

19. In another embodiment, the present disclosure provides a method of treating a disease mediated by KRAS G12C inhibition, the method comprising administering to a patient in need thereof a pharmaceutically effective amount of a pharmaceutical composition comprising the crystalline anhydrous form I of embodiment 1.

20. In another embodiment, the present disclosure provides a method of treating a disease mediated by KRAS G12C inhibition, the method comprising administering to a patient in need thereof a pharmaceutically effective amount of a pharmaceutical composition of embodiment 14.

21. In another embodiment, the present disclosure provides the method of embodiment 19, wherein said disease mediated by G12C inhibition is cancer.

22. In another embodiment, the present disclosure provides the method of embodiment 21, wherein the cancer is lung cancer, pancreatic cancer or colorectal cancer.

23. In another embodiment, the present disclosure provides the method of embodiment 22, wherein the cancer is lung cancer.

24. In another embodiment, the present disclosure provides the method of embodiment 23, wherein the lung cancer is non-small cell lung cancer.

25. In another embodiment, the present disclosure provides an amorphous form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one.

26. In another embodiment, the present disclosure provides the amorphous form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one of embodiment 25, characterized by the powder X-ray diffraction pattern substantially as shown in FIG. 1.

27. In another embodiment, the present disclosure provides the amorphous form of embodiment 25, wherein the form is the M atropisomer.

28. In another embodiment, the present disclosure provides the amorphous form of embodiment 25 having a differential scanning calorimetry thermogram comprising an endotherm with an onset of about 144° C.

29. In another embodiment, the present disclosure provides the amorphous form of embodiment 25 having a thermogravimetric analysis thermogram comprising a weight loss of about 1.5% when heated from about 25° C. to about 275° C.

Figure 4:
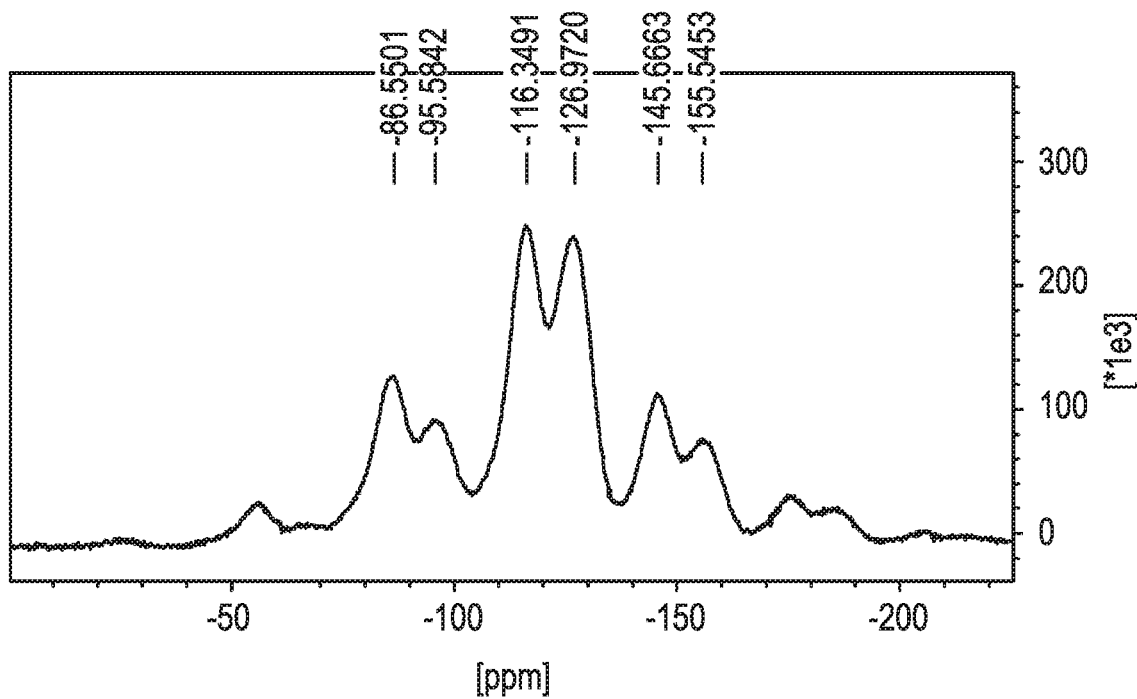
FIG. 4 shows $^{19}$F solid state NMR (SSNMR) for an amorphous form of Compound 1.

30. In another embodiment, the present disclosure provides the amorphous form of embodiment 25, wherein said form is characterized by $^{19}F$ solid state NMR as depicted in FIG. 4.

31. In another embodiment, the present disclosure provides the amorphous form of embodiment 25, wherein said form is characterized by $^{19}F$ solid state NMR, comprising peaks at approximately −86, −96, −116, −127, −146 and −156 ppm.

32. In another embodiment, the present disclosure provides the amorphous form of embodiment 25 which is substantially pure.

33. In another embodiment, the present disclosure provides a pharmaceutical composition comprising the amorphous form of embodiment 25, and a pharmaceutically acceptable excipient.

34. In another embodiment, the present disclosure provides a pharmaceutical composition comprising the amorphous form as in any one of embodiments 25, 26, 27, 28, 29, 30, 31, 32 or 33, or a mixture thereof, and a pharmaceutically acceptable excipient.

35. In another embodiment, the present disclosure provides a pharmaceutical composition of embodiment 34, wherein the composition is a single dose.

36. In another embodiment, the present disclosure provides a method for preparing the amorphous form of embodiment 35, the method comprising dissolving Compound 1 and a suitable solvent to form an amorphous form of Compound 1.

37. In another embodiment, the present disclosure provides the method of embodiment 36 wherein the suitable solvent is methanol.

38. In another embodiment, the present disclosure provides a method of treating a disease mediated by KRAS G12C inhibition, the method comprising administering to a patient in need thereof a pharmaceutically effective amount of a pharmaceutical composition comprising the amorphous form of embodiment 25.

39. In another embodiment, the present disclosure provides the method of embodiment 38, wherein said disease mediated by G12C inhibition is cancer.

40. In another embodiment, the present disclosure provides the method of embodiment 39, wherein the cancer is lung cancer, pancreatic cancer or colorectal cancer.

41. In another embodiment, the present disclosure provides the method of embodiment 40, wherein the cancer is lung cancer.

42. In another embodiment, the present disclosure provides the method of embodiment 41, wherein the lung cancer is non-small cell lung cancer.

43. In another embodiment, the present disclosure provides a crystalline anhydrous form II of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1).

44. In another embodiment, the present disclosure provides the crystalline anhydrous form II of embodiment 43, wherein the anhydrous form II is the M atropisomer.

Figure 10:
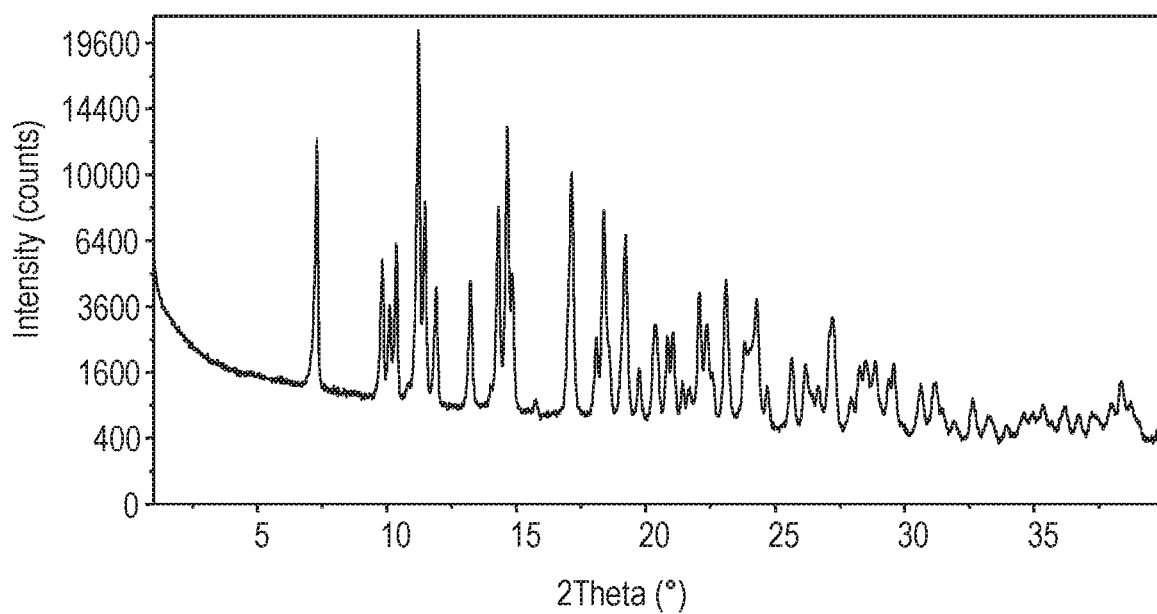
FIG. 10 shows XRPD data for the crystalline anhydrous form II of Compound 1.

45. In another embodiment, the present disclosure provides the crystalline anhydrous form II of embodiment 43, characterized by the powder X-ray diffraction pattern substantially as shown in FIG. 10.

46. In another embodiment, the present disclosure provides the crystalline anhydrous form II of Compound 1 of embodiment 43, wherein said form is characterized by at least three peaks, at least five peaks, or at least seven peaks selected from a powder X-ray diffraction pattern comprising peaks at diffraction angle 2 theta degrees at approximately 7.3, 9.8, 10.1, 10.4, 11.3, 11.5, 11.9, 13.3, 14.3, 14.7, 17.2, and 18.4.

47. In another embodiment, the present disclosure provides the crystalline anhydrous form II of Compound II of embodiment 43, wherein said form is characterized by a powder X-ray diffraction pattern comprising peaks at diffraction angle 2 theta degrees at approximately 7.3, 9.8, 10.1, 11.3, 13.3 and 17.2.

48. In another embodiment, the present disclosure provides the crystalline anhydrous form II of embodiment 43 having a differential scanning calorimetry thermogram comprising an endotherm with an onset of about 193° C.

49. In another embodiment, the present disclosure provides the crystalline anhydrous form II of embodiment 43 having a thermogravimetric analysis thermogram comprising a weight loss of about 1% to about 1.8% when heated from about 25° C. to about 250° C.

Figure 13:
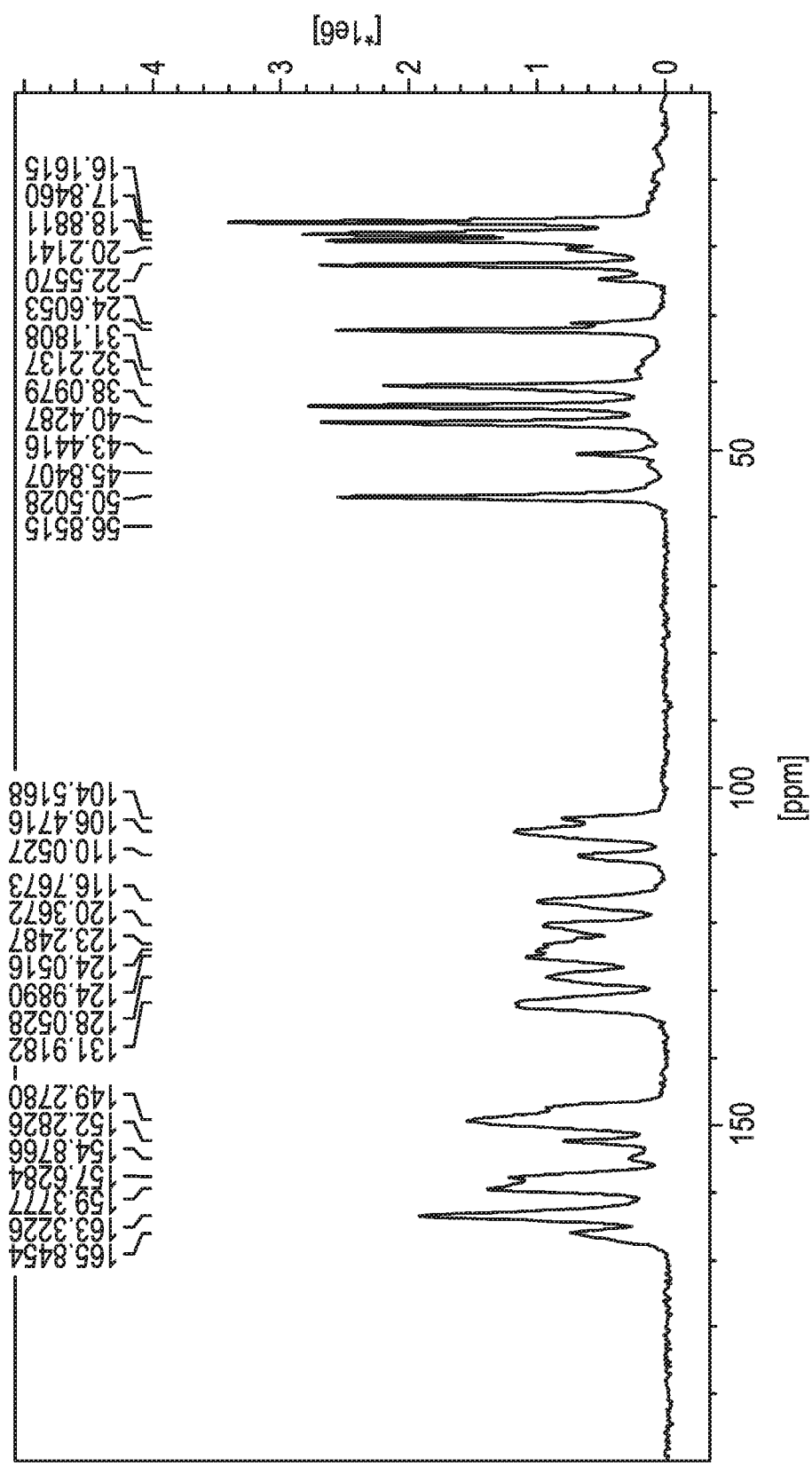
FIG. 13 shows $^{13}$C SSNMR data for crystalline anhydrous form II of Compound 1.

50. In another embodiment, the present disclosure provides the crystalline anhydrous form II of embodiment 43, wherein said form is characterized by $^{13}C$ solid state NMR as depicted in FIG. 13.

51. In another embodiment, the present disclosure provides the crystalline anhydrous form II of embodiment 43, wherein said form is characterized by $^{13}C$ solid state NMR, comprising peaks at approximately 16, 18, 19, 20, 23, 25, 31, 32, 38, 40, 43, 46, 51, 57, 105, 107, 110, 117, 120, 123, 124, 125, 128, 132, 149, 152, 155, 158, 159, 163 and 166 ppm.

Figure 14:
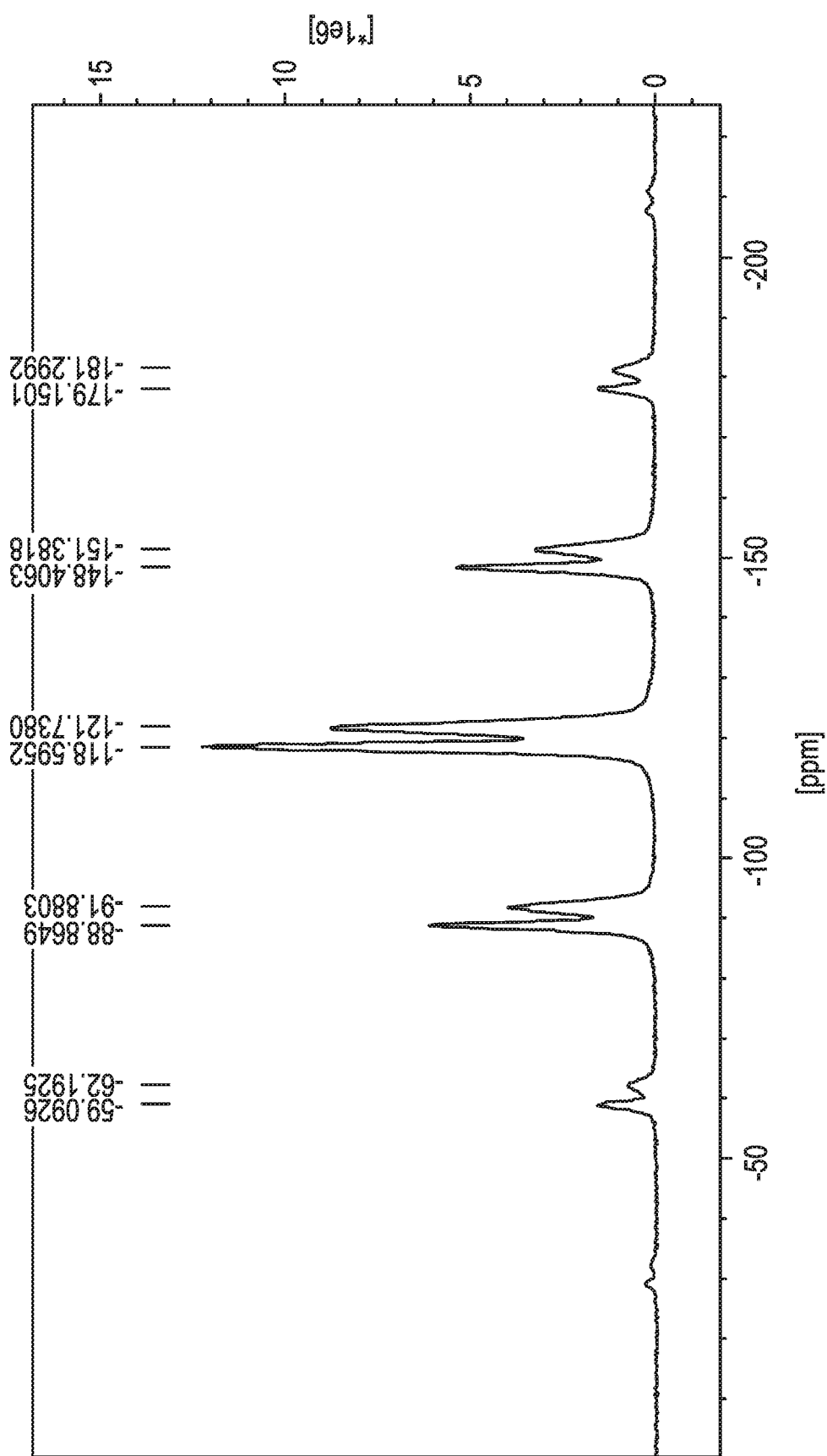
FIG. 14 shows $^{19}$F SSNMR data for crystalline anhydrous form II of Compound 1.

52. In another embodiment, the present disclosure provides the crystalline anhydrous form II of embodiment 43, wherein said form is characterized by $^{19}$F solid state NMR as depicted in FIG. 14.

53. In another embodiment, the present disclosure provides the crystalline anhydrous form II of embodiment 43, wherein said form is characterized by $^{19}$F solid state NMR, comprising peaks at approximately −59, −62, −89, −92, −119, −122, −148, −151, −179 and −181 ppm.

54. In another embodiment, the present disclosure provides the crystalline anhydrous form II of embodiment 43 which is substantially pure.

55. In another embodiment, the present disclosure provides a pharmaceutical composition comprising the crystalline anhydrous form II of embodiment 43, and a pharmaceutically acceptable excipient.

56. In another embodiment, the present disclosure provides a pharmaceutical composition comprising the crystalline anhydrous form II as in any one of embodiments 43, 44, 45, 46, 47, 48, 49, 50, 51, 52, 53, 54 or 55, or a mixture thereof, and a pharmaceutically acceptable excipient.

57. In another embodiment, the present disclosure provides the pharmaceutical composition of embodiment 56, wherein the composition is a single dose.

58. In another embodiment, the present disclosure provides the composition comprising an amorphous form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one and the crystalline anhydrous form II of embodiment 43.

59. In another embodiment, the present disclosure provides a method for preparing the crystalline anhydrous form II of embodiment 43, the method comprising: combining an amorphous form of Compound 1 and a suitable solvent to form a crystalline anhydrous form II of Compound 1.

60. In another embodiment, the present disclosure provides the method of embodiment 59 wherein the suitable solvent is methanol.

61. In another embodiment, the present disclosure provides a method of treating a disease mediated by KRAS G12C inhibition, the method comprising administering to a patient in need thereof a pharmaceutically effective amount of a pharmaceutical composition comprising the crystalline anhydrous form II of embodiment 43.

62. In another embodiment, the present disclosure provides the method of embodiment 61, wherein said disease mediated by G12C inhibition is cancer.

63. In another embodiment, the present disclosure provides the method of embodiment 62, wherein the cancer is lung cancer, pancreatic cancer or colorectal cancer.

64. In another embodiment, the present disclosure provides the method of embodiment 63, wherein the cancer is lung cancer.

65. In another embodiment, the present disclosure provides the method of embodiment 64, wherein the lung cancer is non-small cell lung cancer.

66. In another embodiment, the present disclosure provides a crystalline anhydrous form III of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl) pyrido[2,3-d]pyrimidin-2(1H)-one (Compound 1).

67. In another embodiment, the present disclosure provides the crystalline anhydrous form III of embodiment 66, wherein the anhydrous form III is the M atropisomer.

Figure 15:
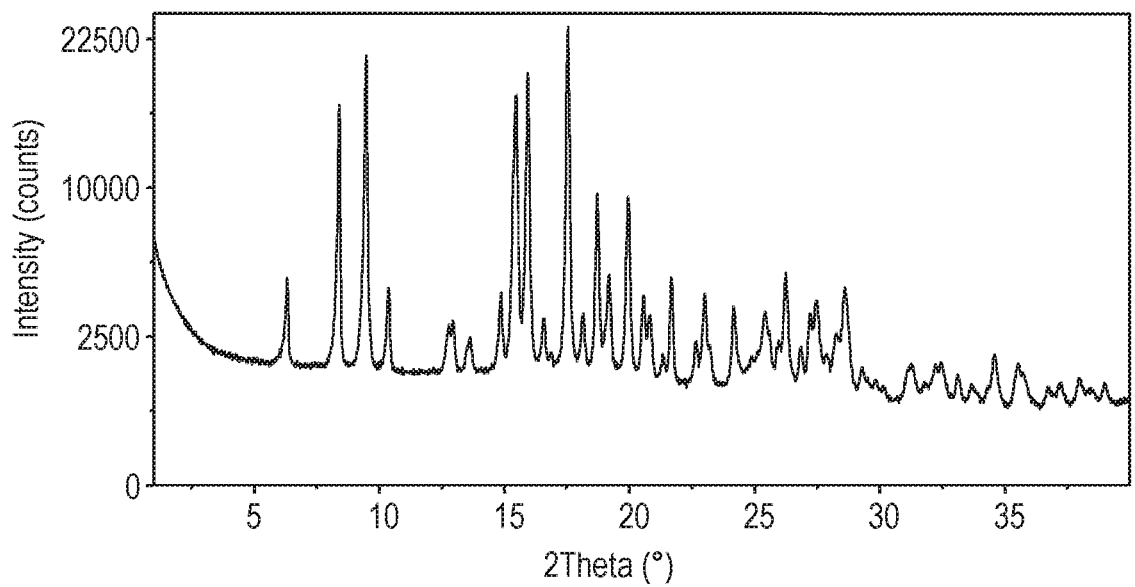
FIG. 15 shows XRPD data for the crystalline anhydrous form III of Compound 1.

68. In another embodiment, the present disclosure provides the crystalline anhydrous form III of embodiment 66, characterized by the powder X-ray diffraction pattern substantially as shown in FIG. 15.

69. In another embodiment, the present disclosure provides the crystalline anhydrous form III of Compound 1 of embodiment 66, wherein said form is characterized by at least three peaks, at least five peaks, or at least seven peaks selected from a powder X-ray diffraction pattern comprising peaks at diffraction angle 2 theta degrees at approximately 6.3, 8.4, 9.5, 10.4, 14.9, 15.4, 15.5, 16.0, and 17.6.

70. In another embodiment, the present disclosure provides the crystalline anhydrous form III of Compound II of embodiment 66, wherein said form is characterized by a powder X-ray diffraction pattern comprising peaks at diffraction angle 2 theta degrees at approximately 6.3, 8.4, 9.5, 15.5, and 16.0.

71. In another embodiment, the present disclosure provides the crystalline anhydrous form III of embodiment 66 having a differential scanning calorimetry thermogram comprising an endotherm with an onset of about 194° C.

72. In another embodiment, the present disclosure provides the crystalline anhydrous form III of embodiment 66 having a thermogravimetric analysis thermogram comprising an approximate negligible weight loss when heated from about 25° C. to about 250° C.

73. In another embodiment, the present disclosure provides the crystalline anhydrous form III of embodiment 66 which is substantially pure.

74. In another embodiment, the present disclosure provides a pharmaceutical composition comprising the crystalline anhydrous form III of embodiment 66, and a pharmaceutically acceptable excipient.

75. In another embodiment, the present disclosure provides a pharmaceutical composition comprising the crystalline anhydrous form III as in any one of embodiments 66, 67, 68, 69, 70, 71, 72, 73 or 74, or a mixture thereof, and a pharmaceutically acceptable excipient.

76. In another embodiment, the present disclosure provides the pharmaceutical composition of embodiment 75, wherein the composition is a single dose.

77. In another embodiment, the present disclosure provides a composition comprising an amorphous form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one and the crystalline anhydrous form III of embodiment 66.

78. In another embodiment, the present disclosure provides a method for preparing the crystalline anhydrous form III of embodiment 66, the method comprising: combining Compound 1 and a suitable solvent to form a crystalline anhydrous form III of Compound 1.

79. In another embodiment, the present disclosure provides the method of embodiment 78 wherein the suitable solvent is acetone.

80. In another embodiment, the present disclosure provides a method of treating a disease mediated by KRAS G12C inhibition, the method comprising administering to a patient in need thereof a pharmaceutically effective amount of a pharmaceutical composition comprising the crystalline anhydrous form III of embodiment 66.

81. In another embodiment, the present disclosure provides the method of embodiment 80, wherein said disease mediated by G12C inhibition is cancer.

82. In another embodiment, the present disclosure provides the method of embodiment 81, wherein the cancer is lung cancer, pancreatic cancer or colorectal cancer.

83. In another embodiment, the present disclosure provides the method of embodiment 82, wherein the cancer is lung cancer.

84. In another embodiment, the present disclosure provides the method of embodiment 82, wherein the lung cancer is non-small cell lung cancer.

85. In another embodiment, the present disclosure provides a crystalline hydrate form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1).

86. In another embodiment, the present disclosure provides the crystalline hydrate form of embodiment 85, wherein the hydrate form is the M atropisomer.

Figure 18:
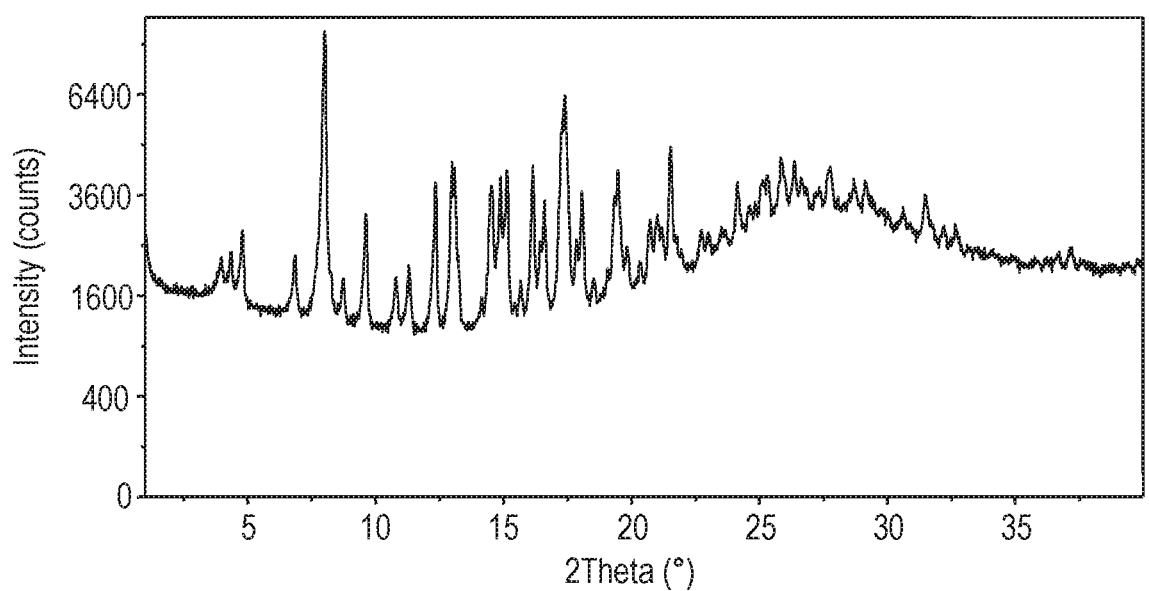
FIG. 18 shows XRPD data for the crystalline hydrate form of Compound 1.

87. In another embodiment, the present disclosure provides the crystalline hydrate form of embodiment 85, characterized by the powder X-ray diffraction pattern substantially as shown in FIG. 18.

88. In another embodiment, the present disclosure provides the crystalline hydrate form of Compound 1 of embodiment 85, wherein said form is characterized by at least three peaks, at least five peaks, or at least seven peaks selected from a powder X-ray diffraction pattern comprising peaks at diffraction angle 2 theta degrees at approximately 4.0, 4.4, 4.8, 6.9, 8.0, 8.8, 9.6, 11.3, 12.4, 13.0, 13.1, 14.6, 14.9, 15.2, 16.2, 16.4, 16.6, 17.3, 17.4, 17.9, and 19.5.

89. In another embodiment, the present disclosure provides the crystalline hydrate form of Compound I of embodiment 85, wherein said form is characterized by a powder X-ray diffraction pattern comprising peaks at diffraction angle 2 theta degrees at approximately 6.9, 8.0, 9.6, 12.4, and 13.1.

90. In another embodiment, the present disclosure provides the crystalline hydrate form of embodiment 85 having a differential scanning calorimetry thermogram comprising an endotherm with an onset of about 91° C.

91. In another embodiment, the present disclosure provides the crystalline hydrate form of embodiment 85 having a thermogravimetric analysis thermogram comprising an approximate 11% weight loss when heated from about 39° C. to about 160° C.

92. In another embodiment, the present disclosure provides the crystalline hydrate form of embodiment 85 which is substantially pure.

93. In another embodiment, the present disclosure provides a pharmaceutical composition comprising the crystalline hydrate form of embodiment 85, and a pharmaceutically acceptable excipient.

94. In another embodiment, the present disclosure provides a pharmaceutical composition comprising the crystalline hydrate form as in any one of embodiments 85, 86, 87, 88, 89, 90, 91, 92 or 93, or a mixture thereof, and a pharmaceutically acceptable excipient.

95. In another embodiment, the present disclosure provides the pharmaceutical composition of embodiment 94, wherein the composition is a single dose.

96. In another embodiment, the present disclosure provides a composition comprising an amorphous form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one and the crystalline hydrate form of embodiment 85.

97. In another embodiment, the present disclosure provides a method for preparing the crystalline hydrate form of embodiment 85, the method comprising: combining Compound 1 and a suitable solvent in the presence of water to form a crystalline hydrate form of Compound 1.

98. In another embodiment, the present disclosure provides the method of embodiment 78 wherein the suitable solvent is methanol.

99. In another embodiment, the present disclosure provides a method of treating a disease mediated by KRAS G12C inhibition, the method comprising administering to a patient in need thereof a pharmaceutically effective amount of a pharmaceutical composition comprising the crystalline hydrate form of embodiment 85.

100. In another embodiment, the present disclosure provides the method of embodiment 99, wherein said disease mediated by G12C inhibition is cancer.

101. In another embodiment, the present disclosure provides the method of embodiment 100, wherein the cancer is lung cancer, pancreatic cancer or colorectal cancer.

102. In another embodiment, the present disclosure provides the method of embodiment 101, wherein the cancer is lung cancer.

103. In another embodiment, the present disclosure provides the method of embodiment 102, wherein the lung cancer is non-small cell lung cancer.

104. In another embodiment, the present disclosure provides a crystalline solvate form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1).

105. In another embodiment, the present disclosure provides the crystalline solvate form of embodiment 104, wherein the solvate form is a THF, MeCN, MEK, EtOAc, DCM, acetone, p-dioxane, methanol, isopropyl alcohol, or ethanol solvate form.

106. In another embodiment, the present disclosure provides a pharmaceutical composition comprising an amorphous form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one and at least one crystalline form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one of any one of embodiments 1, 43, 66, 85 or 104 and a pharmaceutically acceptable excipient.

107. In another embodiment, the present disclosure provides the composition of embodiment 106, which comprises greater than about 50 weight percent crystalline 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one.

108. In another embodiment, the present disclosure provides a pharmaceutical composition comprising at least one crystalline form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one of any one of embodiments 1, 43, 66, 85 or 104 and a pharmaceutically acceptable excipient.

Alternative Embodiments

Provided herein as Embodiment 1 is a compound, wherein the compound is a crystalline form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1) or an atropisomer thereof.

Provided herein as Embodiment 2 is the compound of Embodiment 1, wherein the compound is the M atropisomer of Compound 1.

Provided herein as Embodiment 3 is the compound of Embodiment 1 or 2, wherein the compound is a crystalline anhydrous form of Compound 1.

Provided herein as Embodiment 4 is the compound of any one of Embodiments 1-3, wherein the compound is characterized by a powder X-ray diffraction pattern comprising peaks at 9.0, 12.0, 12.6, and 19.0±0.2 degrees 2 theta as measured by x-ray powder diffraction using an x-ray wavelength of 1.54 Å.

Provided herein as Embodiment 5 is the compound of any one of Embodiments 1-3, wherein the compound is characterized by a powder X-ray diffraction pattern comprising at least three peaks selected from 8.8, 9.0, 10.8, 12.0, 12.6, 12.8, 13.6, 14.2, 15.0, 15.4, 18.0, 18.6, 18.7, 19.0, 19.9, 20.0, 22.9, and 25.0±0.2 degrees 2 theta as measured by x-ray powder diffraction using an x-ray wavelength of 1.54 Å.

Provided herein as Embodiment 6 is the compound of any one of Embodiments 1-3, wherein the compound is characterized by a powder X-ray diffraction pattern comprising at least five peaks selected from 8.8, 9.0, 10.8, 12.0, 12.6, 12.8, 13.6, 14.2, 15.0, 15.4, 18.0, 18.6, 18.7, 19.0, 19.9, 20.0, 22.9, and 25.0±0.2 degrees 2 theta as measured by x-ray powder diffraction using an x-ray wavelength of 1.54 Å.

Provided herein as Embodiment 7 is the compound of any one of Embodiments 1-3, wherein the compound is characterized by a powder X-ray diffraction pattern comprising at least seven peaks selected from 8.8, 9.0, 10.8, 12.0, 12.6, 12.8, 13.6, 14.2, 15.0, 15.4, 18.0, 18.6, 18.7, 19.0, 19.9, 20.0, 22.9, and 25.0±0.2 degrees 2 theta as measured by x-ray powder diffraction using an x-ray wavelength of 1.54 Å.

Provided herein as Embodiment 8 is the compound of any one of Embodiments 1-3, wherein the compound is characterized by a powder X-ray diffraction pattern comprising peaks at 8.8, 9.0, 10.8, 12.0, 12.6, 12.8, 13.6, 14.2, 15.0, 15.4, 18.0, 18.6, 18.7, 19.0, 19.9, 20.0, 22.9, and 25.0±0.2 degrees 2 theta as measured by x-ray powder diffraction using an x-ray wavelength of 1.54 Å.

Provided herein as Embodiment 9 is the compound of any one of Embodiments 1-3, wherein the compound is characterized by the powder X-ray diffraction pattern substantially as shown in FIG. 5 as measured by x-ray powder diffraction using an x-ray wavelength of 1.54 Å.

Provided herein as Embodiment 10 is the compound of any one of Embodiments 1-9, wherein the compound is characterized by a differential scanning calorimetry thermogram comprising an endotherm with an onset of about 293° C.

Provided herein as Embodiment 11 is the compound of any one of Embodiments 1-10, wherein the compound is characterized by a thermogravimetric analysis thermogram comprising a weight loss of about 0.2% when heated from about 25° C. to about 275° C.

Provided herein as Embodiment 12 is the compound of any one of Embodiments 1-11, wherein the compound is characterized by $^{13}C$ solid state NMR comprising at least three peaks selected from peaks at approximately 12, 13, 16, 21, 23, 31, 33, 38, 42, 44, 47, 50, 54, 107, 110, 111, 123, 124, 127, 128, 132, 145, 146, 150, 154, 156, 158, 160, 162, 166, 167, and 168 ppm.

Provided herein as Embodiment 13 is the compound of any one of Embodiments 1-11, wherein the compound is characterized by $^{13}C$ solid state NMR comprising at least five peaks selected from peaks at approximately 12, 13, 16, 21, 23, 31, 33, 38, 42, 44, 47, 50, 54, 107, 110, 111, 123, 124, 127, 128, 132, 145, 146, 150, 154, 156, 158, 160, 162, 166, 167, and 168 ppm.

Provided herein as Embodiment 14 is the compound of any one of Embodiments 1-11, wherein the compound is characterized by $^{13}C$ solid state NMR comprising at least seven peaks selected from peaks at approximately 12, 13, 16, 21, 23, 31, 33, 38, 42, 44, 47, 50, 54, 107, 110, 111, 123, 124, 127, 128, 132, 145, 146, 150, 154, 156, 158, 160, 162, 166, 167, and 168 ppm.

Provided herein as Embodiment 15 is the compound of any one of Embodiments 1-11, wherein the compound is characterized by $^{13}C$ solid state NMR comprising peaks at approximately 12, 13, 16, 21, 23, 31, 33, 38, 42, 44, 47, 50, 54, 107, 110, 111, 123, 124, 127, 128, 132, 145, 146, 150, 154, 156, 158, 160, 162, 166, 167, and 168 ppm.

Provided herein as Embodiment 16 is the compound of any one of Embodiments 1-11, wherein the compound is characterized by $^{13}C$ solid state NMR substantially as depicted in FIG. 8.

Provided herein as Embodiment 17 is the compound of any one of Embodiments 1-16, wherein the compound is characterized by $^{19}F$ solid state NMR comprising peaks at approximately −49, −60, −79, −90, −109, −120, −138, −150, −168, and −179 ppm.

Provided herein as Embodiment 18 is the compound of any one of Embodiments 1-16, wherein the compound is characterized by $^{19}F$ solid state NMR substantially as depicted in FIG. 9.

Provided herein as Embodiment 19 is the compound of any one of Embodiments 1-18, wherein the compound is substantially pure.

Provided herein as Embodiment 20 is a pharmaceutical composition comprising the compound of any one of Embodiments 1-19 and a pharmaceutically acceptable excipient.

Provided herein as Embodiment 21 is the pharmaceutical composition of Embodiment 20, wherein the pharmaceutical composition is a dosage form for oral administration.

Provided herein as Embodiment 22 is the pharmaceutical composition of Embodiment 20 or 21, wherein the dosage form is a solid dosage form.

Provided herein as Embodiment 23 is the pharmaceutical composition of Embodiment 22, wherein the solid dosage form is a tablet.

Provided herein as Embodiment 24 is the pharmaceutical composition of any one of Embodiments 20-23, wherein the pharmaceutical composition comprises 120 mg of the compound.

Provided herein as Embodiment 25 is a compound of any one of Embodiments 1-19 or the pharmaceutical composition of any one of Embodiments 20-24 for use as a medicament.

Provided herein as Embodiment 26 is a compound of any one of Embodiments 1-19 or the pharmaceutical composition of any one of Embodiments 20-24 for use in treating cancer having a KRAS G12C mutation.

Provided herein as Embodiment 27 is the compound or the pharmaceutical composition for use of Embodiment 26, wherein the cancer having a KRAS G12C mutation is lung cancer, pancreatic cancer, or colorectal cancer.

Provided herein as Embodiment 28 is the compound or the pharmaceutical composition for use of Embodiment 26, wherein the cancer having a KRAS G12C mutation is non-small cell lung cancer.

Provided herein as Embodiment 29 is the compound or the pharmaceutical composition for use of Embodiment 26, wherein the cancer having a KRAS G12C mutation is pancreatic cancer.

Provided herein as Embodiment 30 is the compound or the pharmaceutical composition for use of Embodiment 26, wherein the cancer having a KRAS G12C mutation is colorectal cancer.

Provided herein as Embodiment 31 is a use of the compound of any one of Embodiments 1-19 or the pharmaceutical composition of any one of Embodiments 20-24 in the preparation of a medicament for treating cancer having a KRAS G12C mutation.

Provided herein as Embodiment 32 is the use of Embodiment 31, wherein the cancer having a KRAS G12C mutation is lung cancer, pancreatic cancer, or colorectal cancer.

Provided herein as Embodiment 33 is the use of Embodiment 31, wherein the cancer having a KRAS G12C mutation is non-small cell lung cancer.

Provided herein as Embodiment 34 is the use of Embodiment 31, wherein the cancer having a KRAS G12C mutation is pancreatic cancer.

Provided herein as Embodiment 35 is the use of Embodiment 31, wherein the cancer having a KRAS G12C mutation is colorectal cancer.

Provided herein as Embodiment 36 is a method of treating a cancer having a KRAS G12C mutation in a patient in need thereof, the method comprising administering to the patient a therapeutically effective amount of the compound of any one of Embodiments 1-19.

Provided herein as Embodiment 37 is the method of Embodiment 36, wherein the cancer having a KRAS G12C mutation is lung cancer, pancreatic cancer, or colorectal cancer.

Provided herein as Embodiment 38 is the method of Embodiment 36, wherein the cancer having a KRAS G12C mutation is small cell lung cancer.

Provided herein as Embodiment 39 is the method of Embodiment 36, wherein the cancer having a KRAS G12C mutation is pancreatic cancer.

Provided herein as Embodiment 40 is the method of Embodiment 36, wherein the cancer having a KRAS G12C mutation is colorectal cancer.

Provided herein as Embodiment 41 is the compound, use, or method of any one of Embodiments 25-40, wherein the compound is administered at a total daily dose of 960 mg.

Provided herein as Embodiment 42 is the compound, use, or method of any one of Embodiments 25-41, wherein the compound is administered to an adult.

Provided herein as Embodiment 43 is the compound of any one of Embodiments 1-3, wherein the compound is characterized by a powder X-ray diffraction pattern comprising peaks at 7.3, 9.8, 10.1, 11.3, 13.3, and 17.2±0.2 degrees 2 theta as measured by x-ray powder diffraction using an x-ray wavelength of 1.54 Å.

Provided herein as Embodiment 44 is the compound of any one of Embodiments 1-3, wherein the compound is characterized by a powder X-ray diffraction pattern comprising at least three peaks selected from 7.3, 9.8, 10.1, 10.4, 11.3, 11.5, 11.9, 13.3, 14.3, 14.7, 17.2, and 18.4±0.2 degrees 2 theta as measured by x-ray powder diffraction using an x-ray wavelength of 1.54 Å.

Provided herein as Embodiment 45 is the compound of any one of Embodiments 1-3, wherein the compound is characterized by a powder X-ray diffraction pattern comprising at least five peaks selected from 7.3, 9.8, 10.1, 10.4, 11.3, 11.5, 11.9, 13.3, 14.3, 14.7, 17.2, and 18.4±0.2 degrees 2 theta as measured by x-ray powder diffraction using an x-ray wavelength of 1.54 Å.

Provided herein as Embodiment 46 is the compound of any one of Embodiments 1-3, wherein the compound is characterized by a powder X-ray diffraction pattern comprising at least seven peaks selected from 7.3, 9.8, 10.1, 10.4, 11.3, 11.5, 11.9, 13.3, 14.3, 14.7, 17.2, and 18.4±0.2 degrees 2 theta as measured by x-ray powder diffraction using an x-ray wavelength of 1.54 Å.

Provided herein as Embodiment 47 is the compound of any one of Embodiments 1-3, wherein the compound is characterized by a powder X-ray diffraction pattern comprising peaks at 7.3, 9.8, 10.1, 10.4, 11.3, 11.5, 11.9, 13.3, 14.3, 14.7, 17.2, and 18.4±0.2 degrees 2 theta as measured by x-ray powder diffraction using an x-ray wavelength of 1.54 Å.

Provided herein as Embodiment 48 is the compound of any one of Embodiments 1-3, wherein the compound is characterized by the powder X-ray diffraction pattern substantially as shown in FIG. 10 as measured by x-ray powder diffraction using an x-ray wavelength of 1.54 Å.

Provided herein as Embodiment 49 is the compound of any one of Embodiments 1-3 and 43-48, wherein the compound is characterized by a differential scanning calorimetry thermogram comprising an endotherm with an onset of about 193° C.

Provided herein as Embodiment 50 is the compound of any one of Embodiments 1-3 and 43-49, wherein the compound is characterized by having a thermogravimetric analysis thermogram comprising a weight loss of about 1% to about 1.8% when heated from about 25° C. to about 250° C.

Provided herein as Embodiment 51 is the compound of any one of Embodiments 1-3 and 43-50, wherein the compound is characterized by $^{13}C$ solid state NMR comprising peaks at approximately 16, 18, 19, 20, 23, 25, 31, 32, 38, 40, 43, 46, 51, 57, 105, 107, 110, 117, 120, 123, 124, 125, 128, 132, 149, 152, 155, 158, 159, 163, and 166 ppm.

Provided herein as Embodiment 52 is the compound of any one of Embodiments 1-3 and 43-50, wherein the compound is characterized by $^{13}C$ solid state NMR substantially as depicted in FIG. 13.

Provided herein as Embodiment 53 is the compound of any one of Embodiments 1-3 and 43-52, wherein the compound is characterized by $^{19}F$ solid state NMR, comprising peaks at approximately −59, −62, −89, −92, −119, −122, −148, −151, −179 and −181 ppm.

Provided herein as Embodiment 54 is the compound of any one of Embodiments 1-3 and 43-52, wherein the compound is characterized by $^{19}F$ solid state NMR substantially as depicted in FIG. 14.

Provided herein as Embodiment 55 is the compound of any one of Embodiments 43-54, wherein the compound is substantially pure.

Provided herein as Embodiment 56 is a pharmaceutical composition comprising the compound of any one of Embodiments 43-55 and a pharmaceutically acceptable excipient.

Provided herein as Embodiment 57 is the compound of any one of Embodiments 1-3, wherein the compound is characterized by a powder X-ray diffraction pattern comprising peaks at 6.3, 8.4, 9.5, and 16.0±0.2 degrees 2 theta as measured by x-ray powder diffraction using an x-ray wavelength of 1.54 Å.

Provided herein as Embodiment 58 is the compound of any one of Embodiments 1-3, wherein the compound is characterized by a powder X-ray diffraction pattern comprising at least three peaks selected from 6.3, 8.4, 9.5, 10.4, 14.9, 15.4, 15.5, 16.0, and 17.6±0.2 degrees 2 theta as measured by x-ray powder diffraction using an x-ray wavelength of 1.54 Å.

Provided herein as Embodiment 59 is the compound of any one of Embodiments 1-3, wherein the compound is characterized by a powder X-ray diffraction pattern comprising at least five peaks selected from 6.3, 8.4, 9.5, 10.4, 14.9, 15.4, 15.5, 16.0, and 17.6±0.2 degrees 2 theta as measured by x-ray powder diffraction using an x-ray wavelength of 1.54 Å.

Provided herein as Embodiment 60 is the compound of any one of Embodiments 1-3, wherein the compound is characterized by a powder X-ray diffraction pattern comprising at least seven peaks selected from 6.3, 8.4, 9.5, 10.4, 14.9, 15.4, 15.5, 16.0, and 17.6±0.2 degrees 2 theta as measured by x-ray powder diffraction using an x-ray wavelength of 1.54 Å.

Provided herein as Embodiment 61 is the compound of any one of Embodiments 1-3, wherein the compound is characterized by a powder X-ray diffraction pattern comprising peaks at 6.3, 8.4, 9.5, 10.4, 14.9, 15.4, 15.5, 16.0, and 17.6±0.2 degrees 2 theta as measured by x-ray powder diffraction using an x-ray wavelength of 1.54 Å.

Provided herein as Embodiment 62 is the compound of any one of Embodiments 1-3, wherein the compound is characterized by the powder X-ray diffraction pattern substantially as shown in FIG. 15 as measured by x-ray powder diffraction using an x-ray wavelength of 1.54 Å.

Provided herein as Embodiment 63 is the compound of any one of Embodiments 1-3 and 57-62, wherein the compound is characterized by a differential scanning calorimetry thermogram comprising an endotherm with an onset of about 194° C.

Provided herein as Embodiment 64 is the compound of any one of Embodiments 1-3 and 57-63, wherein the compound is characterized by having an approximate negligible weight loss when heated from about 25° C. to about 250° C.

Provided herein as Embodiment 65 is the compound of any one of Embodiments 57-64, wherein the compound is substantially pure.

Provided herein as Embodiment 66 is a pharmaceutical composition comprising the compound of any one of Embodiments 57-65 and a pharmaceutically acceptable excipient.

Provided herein as Embodiment 67 is the compound of Embodiment 1 or 2, wherein the compound is a crystalline hydrate form of Compound 1.

Provided herein as Embodiment 68 is the compound of any one of Embodiments 1, 2, and 67, wherein the compound is characterized by a powder X-ray diffraction pattern comprising peaks at 6.9, 8.0, 9.6, 12.4, and 13.1±0.2 degrees 2 theta as measured by x-ray powder diffraction using an x-ray wavelength of 1.54 Å.

Provided herein as Embodiment 69 is the compound of any one of Embodiments 1, 2, and 67, wherein the compound is characterized by a powder X-ray diffraction pattern comprising at least three peaks selected from 4.0., 4.4, 4.8, 6.9, 8.0, 8.8, 9.6, 11.3, 12.4, 13.0, 13.1, 14.6, 14.9, 15.2, 16.6, 17.3, 17.4, 17.9, and 19.5±0.2 degrees 2 theta as measured by x-ray powder diffraction using an x-ray wavelength of 1.54 Å.

Provided herein as Embodiment 70 is the compound of any one of Embodiments 1, 2, and 67, wherein the compound is characterized by a powder X-ray diffraction pattern comprising at least five peaks selected from 4.0., 4.4, 4.8, 6.9, 8.0, 8.8, 9.6, 11.3, 12.4, 13.0, 13.1, 14.6, 14.9, 15.2, 16.6, 17.3, 17.4, 17.9, and 19.5±0.2 degrees 2 theta as measured by x-ray powder diffraction using an x-ray wavelength of 1.54 521 .

Provided herein as Embodiment 71 is the compound of any one of Embodiments 1, 2, and 67, wherein the compound is characterized by a powder X-ray diffraction pattern comprising at least seven peaks selected from 4.0., 4.4, 4.8, 6.9, 8.0, 8.8, 9.6, 11.3, 12.4, 13.0, 13.1, 14.6, 14.9, 15.2, 16.6, 17.3, 17.4, 17.9, and 19.5±0.2 degrees 2 theta as measured by x-ray powder diffraction using an x-ray wavelength of 1.54 Å.

Provided herein as Embodiment 72 is the compound of any one of Embodiments 1, 2, and 67, wherein the compound is characterized by a powder X-ray diffraction pattern comprising peaks at 4.0., 4.4, 4.8, 6.9, 8.0, 8.8, 9.6, 11.3, 12.4, 13.0, 13.1, 14.6, 14.9, 15.2, 16.2, 16.4, 16.6, 17.3, 17.4, 17.9, and 19.5±0.2 degrees 2 theta as measured by x-ray powder diffraction using an x-ray wavelength of 1.54 Å.

Provided herein as Embodiment 73 is the compound of any one of Embodiments 1, 2, and 67, wherein the compound is characterized by the powder X-ray diffraction pattern substantially as shown in FIG. 18 as measured by x-ray powder diffraction using an x-ray wavelength of 1.54 Å.

Provided herein as Embodiment 74 is the compound of any one of Embodiments 1, 2, and 67-73, wherein the compound is characterized by a differential scanning calorimetry thermogram comprising an endotherm with an onset of about 91° C.

Provided herein as Embodiment 75 is the compound of any one of Embodiments 1, 2, and 67-74, wherein the compound is characterized by having a thermogravimetric analysis thermogram comprising an approximate 11% weight loss when heated from about 39° C. to about 160° C.

Provided herein as Embodiment 76 is the compound of any one of Embodiments 67-75, wherein the compound is substantially pure.

Provided herein as Embodiment 77 is a pharmaceutical composition comprising the compound of any one of Embodiments 67-76 and a pharmaceutically acceptable excipient.

Provided herein as Embodiment 78 is the compound of Embodiment 1 or 2, wherein the compound is a crystalline solvate form of Compound 1.

Provided herein as Embodiment 79 is the compound of Embodiment 78, wherein the compound is a solvate with tetrahydrofuran, acetonitrile, methyl ethylketone, ethyl acetate, dichloromethane, acetone, p-dioxane, methanol, isopropyl alcohol, or ethanol.

Provided herein as Embodiment 80 is a compound, wherein the compound is an amorphous form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1) or an atropisomer thereof.

Provided herein as Embodiment 81 is the compound of Embodiment 80, wherein the compound is the M atropisomer of Compound 1.

Provided herein as Embodiment 82 is the compound of Embodiments 80 or 81, wherein the compound is characterized by the powder X-ray diffraction pattern substantially as shown in FIG. 5 as measured by x-ray powder diffraction using an x-ray wavelength of 1.54 Å.

Provided herein as Embodiment 83 is the compound of any one of Embodiments 80-82, wherein the compound is characterized by a differential scanning calorimetry thermogram comprising an endotherm with an onset of about 144° C.

Provided herein as Embodiment 84 is the compound of any one of Embodiments 80-83, wherein the compound is characterized by a thermogravimetric analysis thermogram comprising a weight loss of about 1.5% when heated from about 25° C. to about 275° C.

Provided herein as Embodiment 85 is the compound of any one of Embodiments 80-84, wherein the compound is characterized by $^{19}$F solid state NMR comprising peaks at approximately −86, −96, −116, −127, −146, and −156 ppm.

Provided herein as Embodiment 86 is the compound of any one of Embodiments 80-85, wherein the compound is characterized by $^{19}$F solid state NMR substantially as depicted in FIG. 4.

Provided herein as Embodiment 87 is the compound of any one of Embodiments 80-86, wherein the compound is substantially pure.

Provided herein as Embodiment 88 is a pharmaceutical composition comprising the compound of any one of Embodiments 80-87 and a pharmaceutically acceptable excipient.

Provided herein as Embodiment 89 is a pharmaceutical composition comprising (1) the compound of any one of Embodiments 4-18, (2) the compound of any one of Embodiments 43-54, (3) the compound of any one of Embodiments 57-64, (4) the compound of any one of Embodiments 67-75, or (5) the compound of any one of Embodiments 80-86, or any mixtures thereof; and a pharmaceutically acceptable excipient.

Crystallization Techniques

Anti-Solvent Precipitation

Solutions of the compounds of the disclosure were prepared in various solvents and an anti-solvent was then added. The solids that formed were isolated and analyzed.

Alternatively, solutions of the compounds of the disclosure were prepared in various solvents, an anti-solvent was then added and the samples were allowed to evaporate. The solids that formed were isolated and analyzed.

Alternatively, solutions of the compounds of the disclosure were prepared in various solvents, an anti-solvent was then added and the samples were cooled to 2° C. to 8° C. The solids that formed were isolated and analyzed.

Sonication

Solutions or suspensions of the compounds of the disclosure were prepared in various solvents and sonicated in an ice bath for 90-180 minutes. The solids were isolated and analyzed.

Slow Cool

Saturated solutions of the compounds of the disclosure were prepared in various solvents at either ambient or elevated temperature. Samples prepared at elevated temperature were allowed to cool to ambient or 2-8° C. The solids that formed were isolated and analyzed.

Evaporation

Solutions of the compounds of the disclosure were prepared in various solvents. Once complete dissolution was observed, the solvent was evaporated by vacuum at ambient or heated temperatures. The solids that formed were isolated and analyzed.

Slow Evaporation

Solutions of the compounds of the disclosure were prepared in various solvents. Once complete dissolution was observed, the solution was allowed to evaporate at ambient in a partially covered vial, with or without a blanket of nitrogen gas. The solids that formed were isolated and analyzed.

Alternatively, solutions of the compounds of the disclosure were prepared followed by sonication for about 90 minutes. Following sonication the samples were allowed to evaporate. Experiments that yielded glasses, were reworked by slurrying the materials with a 15 fold addition of anti-solvent (hexane at 50° C. or water at room temperature). Any resulting solids were isolated and analyzed.

Stress Experiments

Solutions or suspensions of the compounds of the disclosure were prepared in various solvents followed by sonication for 60 minutes. Samples were then stirred to 30° C. for 24-72 hours, followed by stirring at 50° C. for 24 hours. Samples were analyzed by XRPD at each stage before final isolation and analysis.

Slurry Experiments

Solutions of the compounds of the disclosure were prepared by adding enough solids to a given solvent so that excess solids were present. All forms described below can be obtained from various solvents, including, but not limited to, the specific solvents described in the Examples. The mixture was then agitated in a sealed vial at either ambient or elevated temperature. After a given amount of time, the solids were isolated by vacuum or centrifuge filtration and analyzed.

Analytical Techniques

X-Ray Powder Diffraction (XRPD)

X-ray powder diffraction data was obtained using the Phillips X-ray automated powder diffractometer (X'Pert) that was equipped with a fixed slit and a real time multi strip (RTMS) detector. The radiation was CuKα (1.54 Å) and the voltage and current were 45 kV and 40 mA, respectively. Data were collected at room temperature from 3.0 to 40.0 degree 2-theta; step size was 0.0167 degrees; counting time was 15.240 seconds. The stage was rotated at a revolution time of 1.0 second.

Alternatively, X-ray powder diffraction data was obtained using the PANalytical Empyrean automated powder diffractometer that was equipped with a soller slit, beam stop, short antiscatter extension, antiscatter knife edge and a scanning position-sensitive detector (X'Celerator). The radiation was CuKα (1.54 Å). A specimen of the sample was sandwiched between 3 um thick films and analyzed in transmission geometry.

Alternatively, X-ray powder diffraction data was obtained using the PANalytical X'Pert PRO X-ray diffraction system that was equipped with a programmable divergence slit and a real time multi strip (RTMS) detector. The radiation was CuKα (1.54 Å) and the voltage and current were 45 kV and 40 mA, respectively. Data were collected at room temperature from 3.0 to 30.0 or 5 to 45 degrees 2-theta; step size was 0.0334 degrees. The stage was rotated at a revolution time of 2.0 seconds.

It is noted that peak shift of about ±0.2 degrees can occur in XRPD patterns and could be caused by factors such as sample preparation and instrument alignment.

Thermogravimetric Analysis (TGA)

Thermogravimetric analysis was performed on a TGA Discovery Series, TA Instruments. Samples were analyzed under nitrogen at heating rates of 10° C./min over a temperature range from 25° C. to 325° C.

Differential Scanning Calorimetry (DSC)

Differential scanning calorimetry data was collected using standard DSC mode (Discovery Series, TA Instruments). A heating rate of 10° C./min was employed over a temperature range from 25° C. to 350° C. Analysis was run under nitrogen and samples were loaded in aluminum pans. Indium was used as a calibration standard.

Solid State NMR

Approximately 100 mg of sample was packed into a 4 mm ceramic rotor using the SSNMR packing tool. SSNMR spectra were acquired on a Bruker Avance III 500 MHz WB spectrometer. $^{19}F$ spectra were collected using a Bruker double resonance MAS probe operating at a $^1H$ resonance frequency of 500 MHz. A 4-mm H/F/X spinning probe operating at a spinning frequency of 14 kHz was used for all experiments. For $^{19}F$ measurement, a 4 us pi/2 pulse was used and $^1H$ decoupling was carried out using a spinal 64 sequence. A recycle delay of 1.26*T1 was used for optimal S/N/time.

EXAMPLES

Example 1: Identification of Solid State Forms of Compound 1

Within the pharmaceutical research and development field, the investigation of a suitable solid-state form represents a crucial step. Investigating a solid-state form comprises several decisions, mainly the investigation of an anhydrous, salt or co-crystal form and the investigation of a polymorph of the respective anhydrous, salt or co-crystal. During a lead optimization program, several properties of research compounds are optimized, typically leading to one or a few candidates that continue into exploratory development programs. Typically, in the assessment and optimization of physical chemical parameters during lead optimization, the main focus is on solubility. In the present case, Compound 1 has good solubility features. Beyond the optimization of solubility, further physical chemical parameters, such as (1) melting point, (2) thermal behavior, (3) hygroscopicity, (4) crystal habit, (5) polymorphic behavior or physical stability, (6) impurity profile, and (7) chemical stability of the anhydrous or salt form, must be borne in mind when investigating the salt. The melting point of a drug, either as a free base, acid or salt form, should be higher than a certain threshold to allow processing steps such as drying or tabletting. The assessment of thermal behavior, which is typically done by thermogravimetry (TGA) and differential scanning calorimetry (DSC), also includes solid-solid phase transitions. These may be either enantiotropic or monotropic and can be related to the conversion of one polymorph to another or one pseudo-polymorph to another pseudo-polymorph—e.g. a lower solvate or hydrate—or a true polymorph. Hygroscopicity plays a key role in the evaluation of solid-state forms, as this property is highly relevant for many process steps such as drying, storage, blending, granulation, to name but a few. Hygroscopicity can be investigated by dynamic vapor sorption (DVS). Basically, this technique yields information on the amount of moisture that is taken up by the compound at a certain relative humidity level. Discussing thermal behavior and hygroscopicity represents the link to another parameter that has to be considered in anhydrous or salt investigation: a manageable polymorphic behavior is required for an anhydrous or salt form to continue in pharmaceutical development. Therefore, at least a brief assessment of polymorphism is typically carried out in an anhydrous or salt-investigation procedure. In this sense, a manageable polymorphic behavior is not equivalent to the existence of only one or two polymorphic forms, but rather to render a situation where the conversion of polymorphic forms that are not equivalent. Crystal habits can influence anhydrous or salt investigations, and optimization in many cases means moving away a drug in the form of needle-shaped crystals towards e.g. platelets or even cubic crystals exhibiting better flowability. Salt investigation can be a tool to improve impurity profiles of drugs since pharmaceutical salts often exhibit crystal structures that are quite different from the structure of the corresponding free base or acid.

Polymorph and Salt Screen

Accordingly, a polymorph and salt screen of Compound 1 was conducted. Crystalline chloride, phosphate, and mesylate salts as well as crystalline anhydrate, hydrate and solvate forms were identified. None of the identified salts displayed particularly advantageous thermal properties based on DSC data or appeared of lower crystallinity. Of the several remaining free base polymorphs, including the hydrate and solvates, the crystalline anhydrous Form I showed surprising and unexpected advantages.

First, the crystalline anhydrous Form I of Compound 1 is the most thermodynamically stable polymorph identified in the screening process. The crystalline anhydrous Form II and III described herein below convert to crystalline anhydrous Form I upon heating or slurrying.

Specifically, crystalline anhydrous Form II converts to crystalline anhydrous Form I upon heating and recrystallization at 193° C. Crystalline anhydrous Form II converts to crystalline anhydrous Form I upon slurrying in water at 90° C. for 1 hour. A mixture of crystalline anhydrous Form I and crystalline anhydrous Form II converts to crystalline anhydrous Form I upon slurrying in 90/10 v/v water/acetonitrile at RT for 7 days. A mixture of crystalline anhydrous Form I and crystalline anhydrous Form II converts to crystalline anhydrous Form I upon slurrying in heptane at 80° C. for 1 day.

Crystalline anhydrous Form III melts at 180° C. Crystalline anhydrous Form III converts to crystalline anhydrous Form I upon melting and recrystallization at 220° C. A mixture of crystalline anhydrous Form I and crystalline anhydrous Form III converts to crystalline anhydrous Form I upon slurrying in ethanol at RT for 10 days. A mixture of crystalline anhydrous Form I and crystalline anhydrous Form III converts to crystalline anhydrous Form I upon slurrying in methanol at RT for 10 days.

The high melting point of crystalline anhydrous Form I is a further indicator of its thermodynamic stability (DSC endotherm onset of about 293° C.).

Second, crystalline anhydrous Form I is less hygroscopic compared to crystalline anhydrous Forms II and III (Form I absorbed 0.5-1.0% wt moisture between 0 and 90% RH at 25° C.; Form II absorbed 2-2.5% wt moisture between 0 and 90% RH at 25° C.; Form III absorbed 7.0% wt moisture between 0-95% RH at 25° C.).

Moreover, crystalline anhydrous Form I was physically and chemically stable in the solid state, showing no degradation peaks by HPLC or any changes in the investigated solid state properties, including XRPD, melting point onset and heat of fusion by DSC, and volatiles content by TGA, for 14 weeks at 25° C./60% RH, 40° C./75% RH, 40° C./ambient RH, and 60° C./ambient RH. Furthermore, crystalline anhydrous Form I was stable in an excipient compatibility study in 3 prototype blends that were stored for 4 weeks at 40° C./75% RH. Crystalline anhydrous Form I was also stable to ultraviolet and visible light in the solid state.

Accordingly, crystalline anhydrous Form I shows advantageous and unexpected overall properties, in particular when compared with other forms and salts identified.

Polymorph Screen

A polymorph screen to generate the different solid forms of the M atropisomer of 6-fluoro-7-(2-fluoro-6-hydroxyphenyl)-1-(4-methyl-2-(2-propanyl)-3-pyridinyl)-4-((2S)-2- methyl-4-(2-propenoyl)-1-piperazinyl)pyrido[2,3-d]pyrimidin-2(1H)-one (Compound 1) was carried out as described below. As a matter of convenience, "Compound 1" as referred to in the Examples that follow is to be understood to be the M atropisomer of Compound 1.

Example 1

Compound 1 can be made according to the procedure disclosed in US Publication 2018/0334454 published on Nov. 22, 2018, which is herein incorporated by reference in its entirety.

Amorphous Form I of Compound 1 was prepared by rotary evaporation from MeOH with secondary drying under vacuum at RT.

The relative peak areas of the amorphous form of the XRPD, TGA, DSC and $^{19}$F SSNMR are represented in FIGS. 1, 2, 3 and 4.

Differential scanning calorimetry (DSC) thermogram comprising an endotherm with an onset of about 144° C.

Thermogravimetric analysis (TGA) thermogram comprising a weight loss of about 1.5% when heated from about 25° C. to about 275° C.

$^{19}$F SSNMR: −86, −96, −116, −127, −146 and −156 ppm.

A number of anhydrous and hydrate forms of Compound 1 were investigated (see Table 1 below). Further characterization of these crystalline forms, such as melting point, thermal behavior, hygroscopicity, crystal habit, particle size, polymorphic behavior, stability, and purity, were investigated. These forms were characterized by methods including XRPD, TGA, and DSC analysis. Rel. Int % is the percent relative intensity based on the largest peak.

Figure 21:
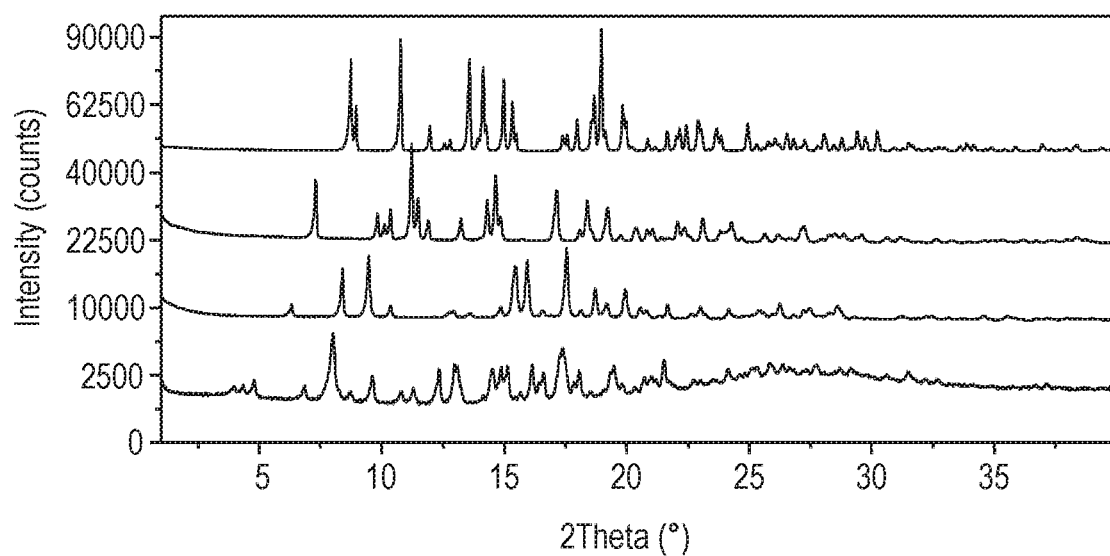
FIG. 21 is the overlay XRPD data (from top to bottom) for the crystalline anhydrous forms I, II, and III and the crystalline hydrate form of Compound 1.

FIG. 21 illustrates the overlay of crystalline anhydrous Forms I, II, III and the variable hydrate Form I of Compound 1 (Forms I-III and variable hydrate Form I are in order from top to bottom).

TABLE 1

XRPD Differentiating Peaks

| Free Base Form | Peaks Unique to Each Form (KA1 °) | | | | | |
|---|---|---|---|---|---|---|
| Form I | 9.0 | 12.0 | 12.6 | 19.0 | — | — |
| Form II | 7.3 | 9.8 | 10.1 | 11.3 | 13.3 | 17.2 |
| Form III | 6.3 | 8.4 | 9.5 | 16.0 | — | — |
| Hydrate Form I | 6.9 | 8.0 | 9.6 | 12.4 | 13.1 | — |

Example 2: Preparation of Crystalline Anhydrous Form I of Compound 1

Crystalline anhydrous Form I was prepared by charging 1.5 g of crystalline anhydrous Form II of Compound 1 with 10 mL of water to form a slurry. The slurry was heated to 90° C. for 2 h, then stirred overnight at RT. The solids were filtered, dried under vacuum and identified as crystalline anhydrous Form I by XRPD. DSC endotherm onset of about 292.6° C., TGA comprising a weight loss of about 0.2% when heated from about 25° C. to about 275° C.

Figure 6:
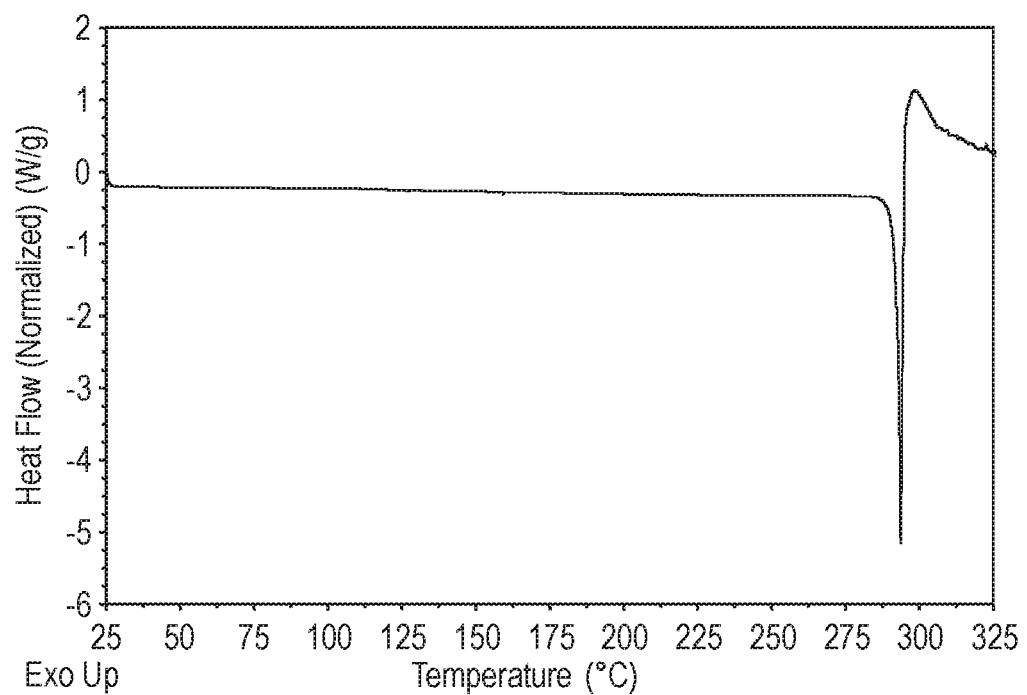
FIG. 6 shows DSC data for crystalline anhydrous form I of Compound 1.
Figure 7:
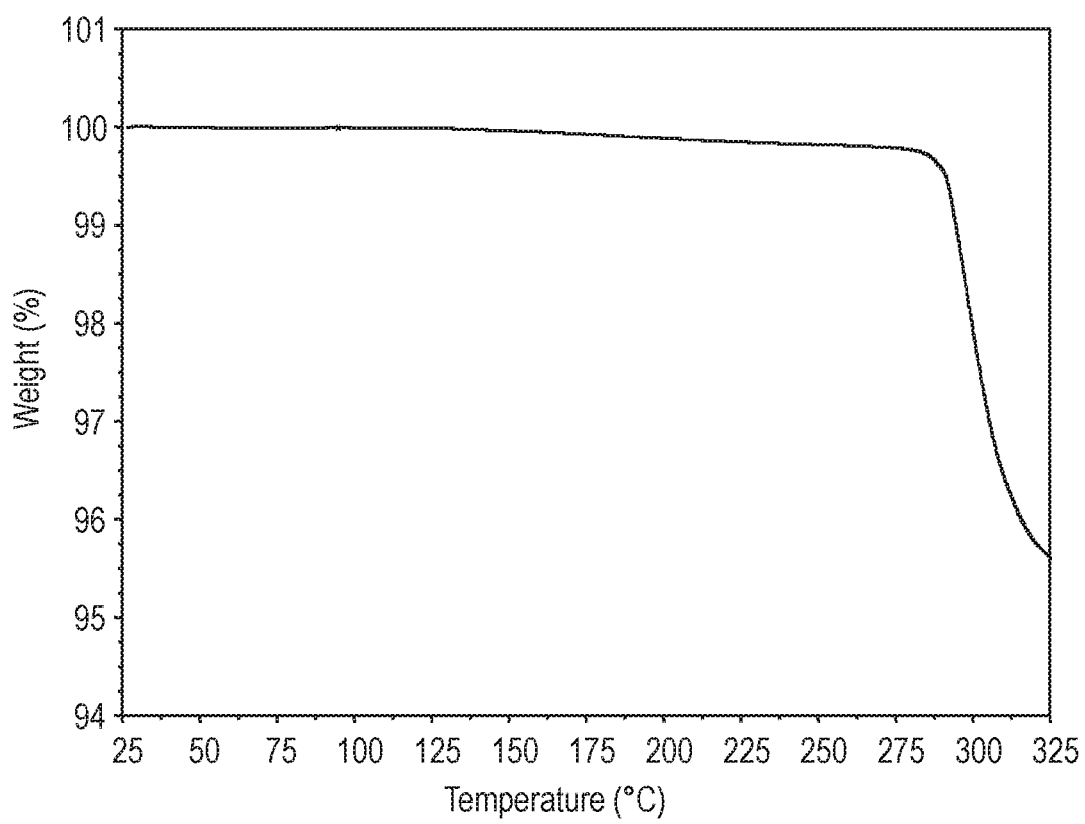
FIG. 7 shows TGA data for crystalline anhydrous form I of Compound 1.

The crystalline anhydrous Form I prepared above was characterized by proton NMR, X-ray powder diffraction (XRPD) data (FIG. 5), DSC (FIG. 6), TGA (FIG. 7), carbon 13 SSNMR (FIGS. 8), and $^{19}$F SSNMR (FIG. 9).

$^1$H NMR (400 MHz, DMSO-$d_6$) δ ppm 0.93 (d, J=6.84 Hz, 3 H) 1.07 (d, J=6.63 Hz, 3 H) 1.35 (d, J=6.84 Hz, 3 H) 1.90 (s, 3 H) 2.66-2.75 (m, 1 H) 3.14 (br t, J=11.20 Hz, 1 H) 3.59-3.75 (m, 2 H) 3.97-4.08 (m, 1 H) 4.08-4.22 (m, 1 H) 4.22-4.43 (m, 2 H) 4.90 (br s, 1 H) 5.74-5.79 (m, 1 H) 6.21 (br d, J=17.00 Hz, 1 H) 6.65-6.75 (m, 2 H) 6.79-6.92 (m, 1H) 7.18 (d, J=4.98 Hz, 1 H) 7.23-7.31 (m, 1 H) 8.22-8.33 (m, 1 H) 8.38 (d, J=4.77 Hz, 1 H) 10.19 (s, 1 H)

$^{13}$C SSNMR: 12, 13, 16, 21, 23, 31, 33, 38, 42, 44, 47, 50, 54, 107, 110, 111, 123, 124, 127, 128, 132, 145, 146, 150, 154, 156, 158, 160, 162, 166, 167.7 and 168 ppm.

$^{19}$F SSNMR: −49, −60, −79, −90, −109, −120, −138, −150, −168 and −179 ppm.

TABLE 2

XRPD data of the crystalline anhydrous Form I of Compound 1
XRPD Peak Table:

| Pos. [°2 Th.] | Rel. Int. [%] |
|---|---|
| 8.8 | 72.02 |
| 9.0 | 32.38 |
| 10.8 | 89.48 |
| 12.0 | 17.57 |
| 12.6 | 5.21 |
| 12.8 | 7.83 |
| 13.6 | 70.38 |
| 13.9 | 8.16 |
| 14.2 | 64.52 |
| 14.3 | 15.98 |
| 15.0 | 54.34 |
| 15.4 | 34.78 |
| 15.5 | 11.84 |
| 17.4 | 10.60 |
| 17.6 | 11.10 |
| 18.0 | 22.28 |
| 18.6 | 20.76 |
| 18.7 | 41.59 |
| 19.0 | 100.00 |
| 19.2 | 13.83 |
| 19.9 | 34.21 |
| 20.0 | 20.81 |
| 20.2 | 2.92 |
| 20.9 | 8.05 |
| 21.2 | 2.59 |
| 21.7 | 14.40 |
| 22.0 | 9.77 |
| 22.2 | 16.27 |
| 22.5 | 18.45 |
| 22.9 | 21.27 |
| 23.1 | 14.15 |
| 23.7 | 15.87 |
| 23.9 | 10.39 |
| 25.0 | 19.32 |
| 25.3 | 4.26 |
| 25.6 | 1.90 |
| 25.8 | 6.05 |
| 26.1 | 7.93 |
| 26.3 | 4.28 |
| 26.6 | 12.27 |
| 26.8 | 8.19 |
| 27.3 | 7.42 |
| 27.8 | 3.31 |
| 28.0 | 11.20 |
| 28.5 | 3.83 |
| 28.8 | 8.53 |
| 29.1 | 2.01 |
| 29.4 | 13.68 |
| 29.7 | 9.66 |
| 30.2 | 13.60 |
| 30.9 | 1.84 |
| 31.3 | 1.53 |
| 31.5 | 5.71 |
| 31.7 | 3.54 |
| 31.9 | 1.13 |
| 32.3 | 1.55 |
| 32.6 | 1.69 |
| 32.8 | 2.47 |
| 33.0 | 2.11 |

TABLE 2-continued

XRPD data of the crystalline anhydrous Form I of Compound 1
XRPD Peak Table:

| Pos. [°2 Th.] | Rel. Int. [%] |
| --- | --- |
| 33.6 | 3.23 |
| 33.9 | 5.14 |
| 34.2 | 3.90 |
| 34.7 | 0.67 |
| 34.9 | 1.76 |
| 35.0 | 1.62 |
| 35.4 | 1.10 |
| 35.8 | 2.43 |
| 36.5 | 0.59 |
| 37.0 | 4.04 |
| 37.0 | 2.30 |
| 37.3 | 0.80 |
| 37.7 | 0.66 |
| 38.0 | 1.27 |
| 38.3 | 2.60 |
| 38.4 | 4.02 |
| 39.1 | 0.51 |
| 39.4 | 1.88 |
| 39.8 | 0.90 |

Example 3: Preparation of The Anhydrous Form II of the Compound 1

The crystalline anhydrous Form II of Compound 1 was prepared by charging 0.987 g of amorphous Compound 1 with 15 mL MeOH to produce a slurry. The isolated solids were identified as crystalline anhydrous Form II by XRPD.

DSC onset of about 192.5° C., TGA comprising a weight loss of about 1% to about 1.8% when heated from about 25° C. to about 250° C.

Figure 11:
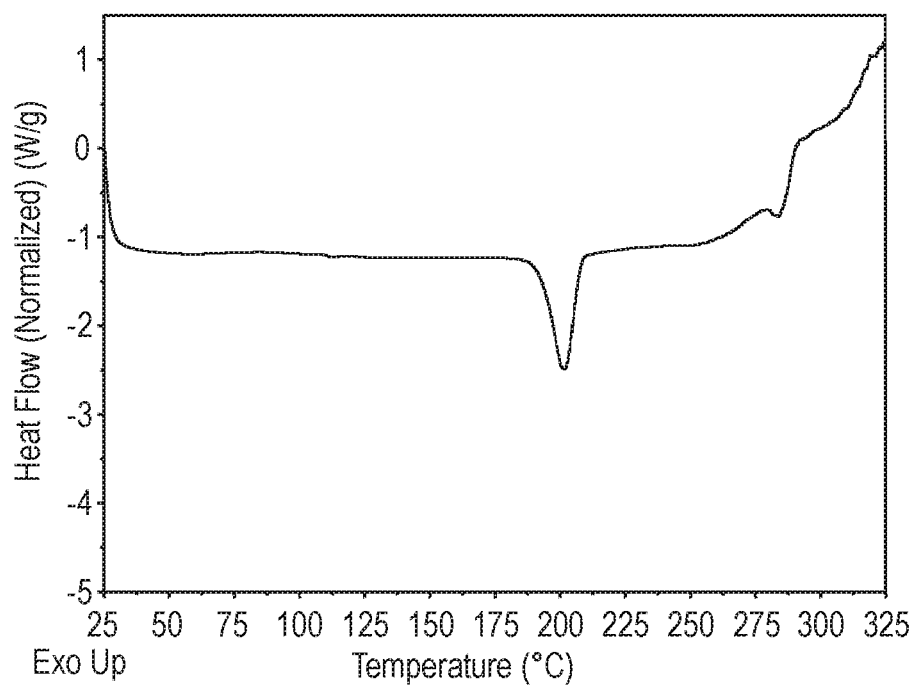
FIG. 11 shows DSC data for crystalline anhydrous form II of Compound 1.
Figure 12:
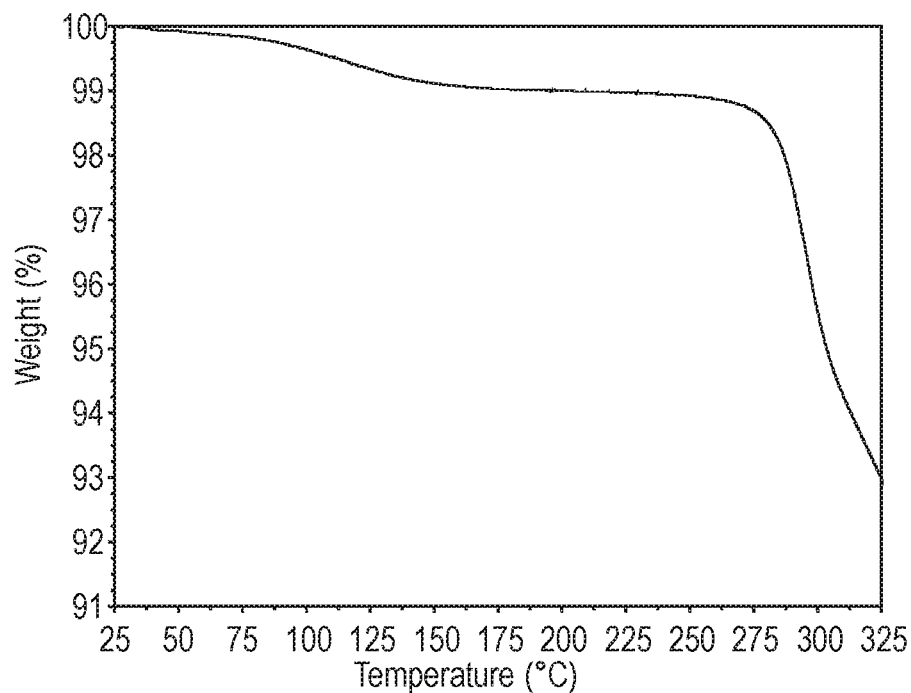
FIG. 12 shows TGA data for crystalline anhydrous form II of Compound 1.

The crystalline anhydrous Form II of Compound 1 prepared above was characterized by proton NMR, X-ray powder diffraction (XRPD) data (FIG. 10), DSC (FIG. 11), TGA (FIG. 12), carbon 13SSNMR (FIGS. 13), and $^{19}$F SSNMR (FIG. 14).

$^1$H NMR (400 MHz, DMSO-d$_6$) δ ppm 0.93 (d, J=6.63 Hz, 4 H) 1.07 (d, J=6.84 Hz, 4 H) 1.35 (d, J=6.63 Hz, 4 H) 1.90 (s, 3 H) 2.60-2.76 (m, 1 H) 3.11-3.28 (m, 2 H) 3.68 (br d, J=13.89 Hz, 2 H) 4.08 (d, J=5.18 Hz, 2 H) 4.32 (br d, J=13.68 Hz, 2 H) 4.90 (br s, 1 H) 5.74-5.79 (m, 1 H) 6.21 (br d, J=16.17 Hz, 1 H) 6.65-6.76 (m, 2 H) 6.80-6.92 (m, 1 H) 7.18 (d, J=4.98 Hz, 1 H) 7.23-7.31 (m, 1 H) 8.29 (br d, J=9.33 Hz, 1 H) 8.38 (d, J=4.98 Hz, 1 H) 10.19 (s, 1 H).

$^{13}$C SSNMR: 16, 18, 19, 20, 23, 25, 31, 32, 38, 40, 43, 46, 51, 57, 105, 107, 110, 117, 120, 123, 124, 125, 128, 132, 149, 152, 155, 158, 159, 163 and 166 ppm.

$^{19}$F SSNMR: −59, −62, −89, −92, −119, −122, −148, −151, −179 and −181 ppm.

TABLE 3

XRPD data of the crystalline anhydrous Form II of Compound 1

| Pos. [°2Th.] | Rel. Int. [%] |
| --- | --- |
| 7.3 | 55.69 |
| 9.8 | 22.74 |
| 10.1 | 13.34 |
| 10.4 | 26.87 |
| 11.3 | 100.00 |
| 11.5 | 38.51 |
| 11.9 | 17.55 |
| 13.3 | 19.19 |
| 14.3 | 37.78 |
| 14.7 | 63.63 |
| 14.9 | 20.80 |
| 15.8 | 1.24 |
| 17.2 | 47.51 |
| 18.1 | 9.48 |
| 18.4 | 37.17 |
| 18.6 | 6.86 |
| 19.2 | 31.06 |
| 19.8 | 5.10 |
| 20.4 | 11.69 |
| 20.9 | 10.16 |
| 21.1 | 10.57 |
| 21.4 | 3.78 |
| 21.7 | 3.26 |
| 22.1 | 18.04 |
| 22.4 | 12.23 |
| 22.6 | 4.78 |
| 23.1 | 20.56 |
| 23.8 | 9.50 |
| 24.3 | 17.04 |
| 24.7 | 3.75 |
| 25.6 | 6.63 |
| 26.2 | 6.15 |
| 27.1 | 9.80 |
| 27.3 | 12.94 |
| 27.9 | 2.58 |
| 28.3 | 6.04 |
| 28.5 | 7.17 |
| 28.9 | 7.06 |
| 29.4 | 4.82 |
| 29.6 | 6.76 |
| 30.7 | 4.35 |
| 31.2 | 4.41 |
| 31.5 | 1.70 |
| 31.9 | 0.83 |
| 32.6 | 2.54 |
| 33.3 | 1.23 |
| 34.0 | 0.53 |
| 34.6 | 1.58 |
| 35.0 | 1.66 |
| 35.4 | 2.35 |
| 36.2 | 2.20 |
| 36.8 | 1.47 |
| 37.2 | 1.73 |
| 38.0 | 2.55 |
| 38.4 | 4.75 |
| 38.8 | 2.68 |

Example 4: Preparation Of Crystalline Anhydrous Form III Of Compound 1

The crystalline anhydrous Form III of Compound 1 was prepared by drying the acetone solvate Form I of Compound 1 by vacuum at ~65-76° C. DSC endotherm onset of about 194° C., TGA comprising an approximate negligible weight loss when heated from about 25° C. to about 250° C.

Figure 16:
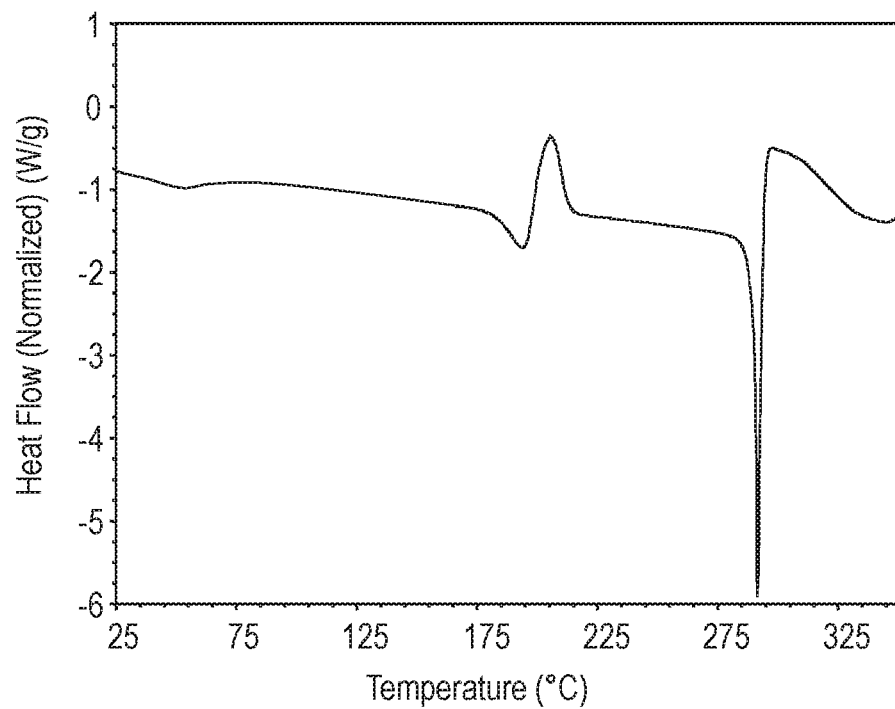
FIG. 16 shows DSC data for crystalline anhydrous form III of Compound 1.
Figure 17:
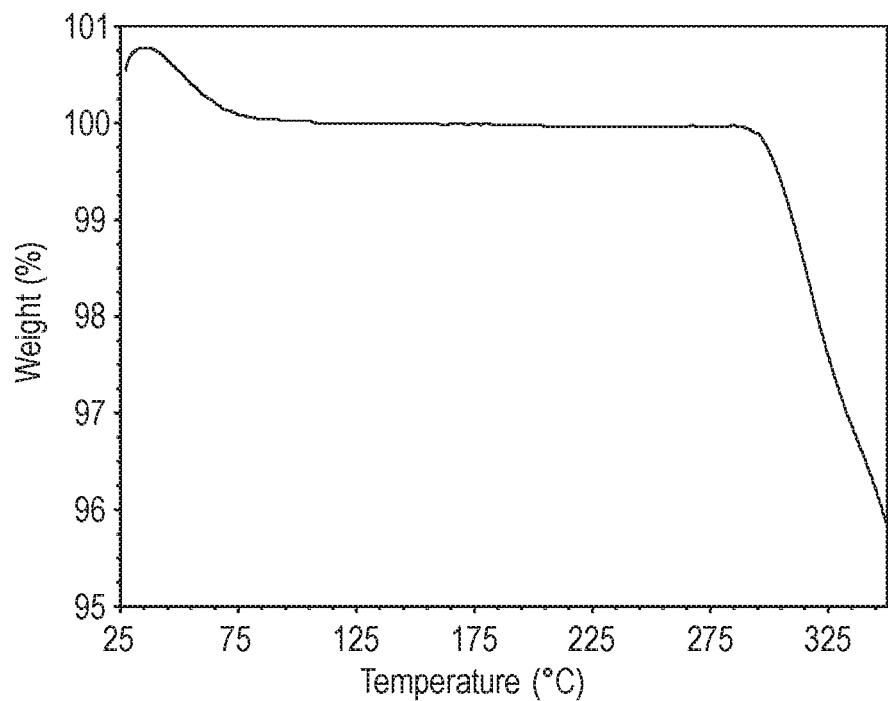
FIG. 17 shows TGA data for crystalline anhydrous form III of Compound 1.

The crystalline anhydrous Form III of Compound 1 prepared above was characterized by proton NMR, X-ray powder diffraction (XRPD) data (FIG. 15), DSC (FIG. 16), and TGA (FIG. 17).

$^1$H NMR (400 MHz, DMSO-d$_6$) δ ppm 0.93 (d, J=6.82 Hz, 3 H) 1.07 (d, J=6.61 Hz, 3 H) 1.35 (d, J=6.61 Hz, 2 H) 1.90 (s, 2 H) 2.64-2.80 (m, 1 H) 3.14 (br t, J=10.66 Hz, 1 H) 3.45-3.57 (m, 1 H) 3.58-3.76 (m, 1 H) 3.94-4.08 (m, 1 H) 4.14 (br d, J=13.00 Hz, 1 H) 4.21-4.47 (m, 2 H) 4.90 (br s, 1 H) 5.76 (dd, J=10.44, 2.13 Hz, 1 H) 6.21 (br d, J=16.84 Hz, 1 H) 6.55-6.78 (m, 2 H) 6.86 (dt, J=16.20, 11.29 Hz, 1 H) 7.13-7.21 (m, 1 H) 7.21-7.33 (m, 1 H) 8.21-8.34 (m, 1 H) 8.39 (d, J=4.90 Hz, 1 H) 10.20 (br s, 1 H).

TABLE 4

XRPD data of the Anhydrous Form III of Compound 1

| Pos. [°2Th.] | Rel. Int. [%] |
|---|---|
| 6.3 | 14.11 |
| 8.4 | 63.06 |
| 9.5 | 84.68 |
| 10.4 | 12.93 |
| 12.8 | 6.80 |
| 13.0 | 6.79 |
| 13.7 | 4.59 |
| 14.9 | 12.72 |
| 15.4 | 45.73 |
| 15.5 | 69.05 |
| 16.0 | 79.08 |
| 16.6 | 8.35 |
| 17.6 | 100.00 |
| 18.2 | 9.32 |
| 18.7 | 37.73 |
| 19.2 | 16.82 |
| 20.0 | 36.44 |
| 20.6 | 13.07 |
| 20.8 | 9.52 |
| 21.7 | 3.50 |
| 21.7 | 16.74 |
| 22.7 | 5.52 |
| 23.0 | 13.50 |
| 23.2 | 4.81 |
| 24.2 | 11.39 |
| 24.9 | 3.83 |
| 25.4 | 10.81 |
| 25.9 | 5.35 |
| 26.7 | 17.58 |
| 26.8 | 5.18 |
| 27.2 | 10.38 |
| 27.5 | 12.87 |
| 27.9 | 4.42 |
| 28.3 | 7.66 |
| 28.6 | 15.70 |
| 29.3 | 3.10 |
| 29.7 | 1.70 |
| 30.2 | 1.02 |
| 31.4 | 2.93 |
| 32.2 | 3.52 |
| 32.5 | 3.97 |
| 33.1 | 2.31 |
| 33.7 | 1.35 |
| 34.6 | 4.91 |
| 35.5 | 3.74 |
| 35.8 | 2.54 |
| 36.7 | 1.18 |
| 37.3 | 1.65 |
| 38.0 | 2.18 |
| 39.0 | 1.57 |

Example 5: Preparation of Variable Hydrate Form I of Compound 1

The variable hydrate Form I of Compound 1 was prepared by dissolving Compound 1 in MeOH at RT, polish filtering then charging with aliquots of water as an antisolvent until precipitation occurred. Solids were isolated after stirring at RT for 13 days.

DSC first endotherm onset of about at 91° C., TGA comprising an approximate 11% weight loss when heated from about 39° C. to about 160° C. (3.9 mol water).

Karl Fischer 10.63% (3.7 mol) water.

Figure 19:
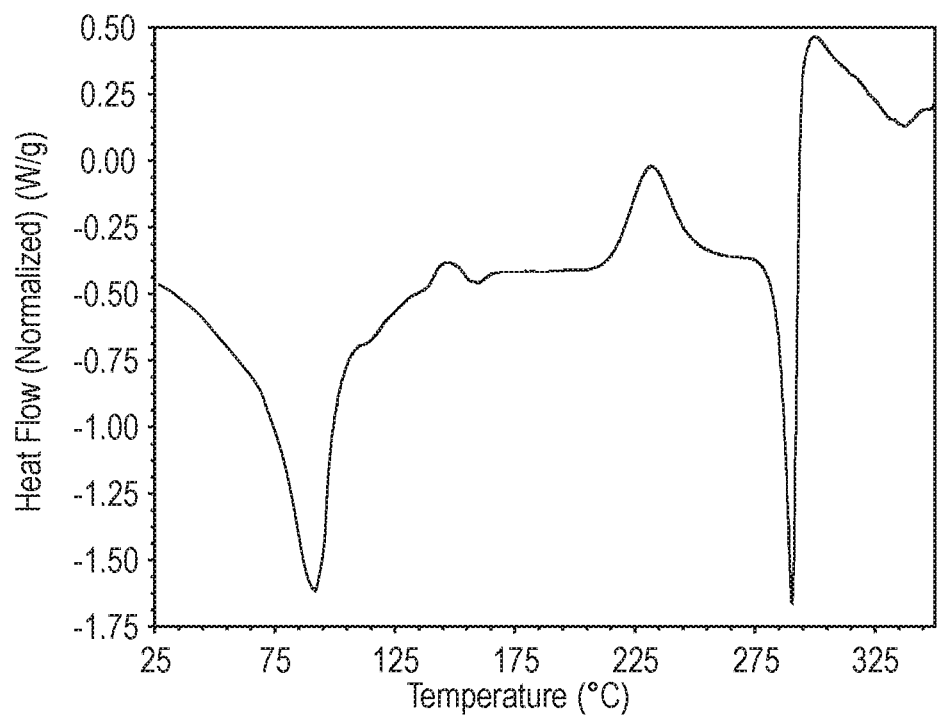
FIG. 19 shows DSC data for the crystalline hydrate form of Compound 1.
Figure 20:
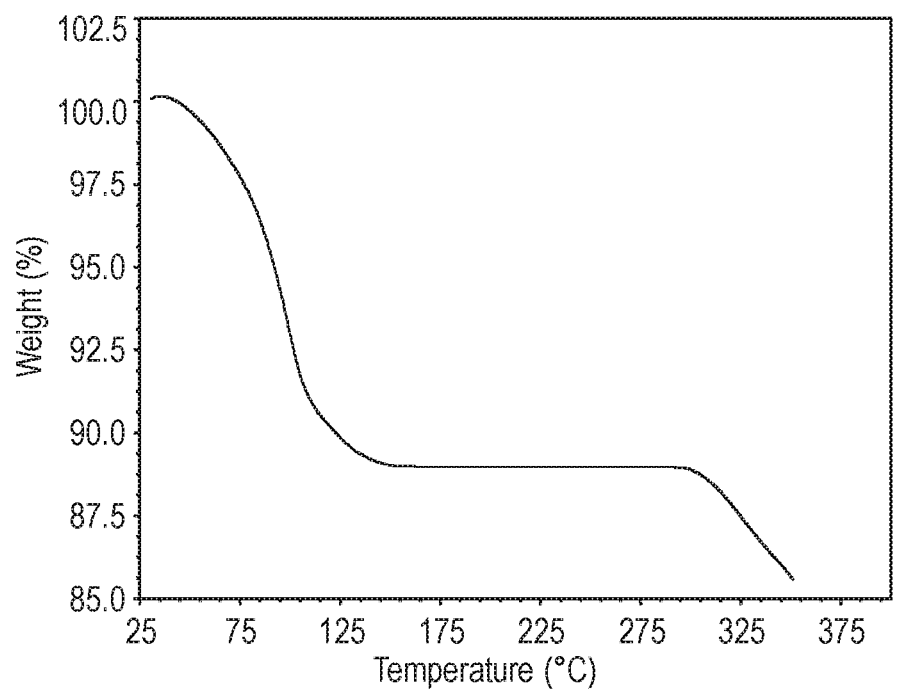
FIG. 20 shows TGA data for the crystalline hydrate form of Compound 1.

The crystalline variable hydrate Form I prepared above was characterized by proton NMR, X-ray powder diffraction (XRPD) data (FIG. 18), DSC (FIG. 19), and TGA (FIG. 20).

$^1$H NMR (400 MHz, DMSO-d$_6$) δ ppm 0.94 (d, J=6.62 Hz, 3 H) 1.08 (d, J=6.84 Hz, 3 H) 1.35 (d, J=6.63 Hz, 3 H) 1.90 (s, 3 H) 2.61-2.79 (m, 1 H) 3.15 (br t, J=11.01 Hz, 1 H) 3.40-3.58 (m, 2 H) 3.59-3.84 (m, 3 H) 3.86-4.09 (m, 1 H) 4.15 (br d, J=12.39 Hz, 1 H) 4.21-4.47 (m, 3 H) 4.90 (br s, 2 H) 5.73-5.82 (m, 1 H) 6.15-6.21 (m, 1 H) 6.23 (br d, J=4.92 Hz, 1 H) 6.63-6.77 (m, 3 H) 6.78-7.03 (m, 2 H) 7.14-7.31 (m, 3 H) 8.14-8.35 (m, 1 H) 8.39 (d, J=4.92 Hz, 1 H).

TABLE 5

XRPD data of the Crystalline Variable Hydrate Form I of Compound 1
XRPD Peak Table:

| Pos. [°2Th.] | Rel. Int. [%] |
|---|---|
| 4.0 | 10.00 |
| 4.4 | 12.08 |
| 4.8 | 17.94 |
| 6.9 | 12.94 |
| 8.0 | 100.00 |
| 8.8 | 8.55 |
| 9.6 | 26.66 |
| 10.8 | 10.41 |
| 11.3 | 13.06 |
| 12.4 | 36.89 |
| 13.0 | 43.60 |
| 13.1 | 41.65 |
| 14.2 | 5.04 |
| 14.6 | 35.20 |
| 14.9 | 38.07 |
| 15.2 | 40.25 |
| 15.7 | 7.44 |
| 16.2 | 40.04 |
| 16.4 | 17.22 |
| 16.6 | 29.36 |
| 17.3 | 54.43 |
| 17.4 | 68.45 |
| 17.9 | 16.60 |
| 18.1 | 30.16 |
| 18.6 | 5.51 |
| 19.3 | 27.13 |
| 19.5 | 35.91 |
| 19.8 | 13.20 |
| 20.4 | 8.31 |
| 20.8 | 20.25 |
| 21.0 | 21.40 |
| 21.5 | 43.72 |
| 22.8 | 14.71 |
| 23.0 | 13.61 |
| 23.6 | 14.15 |
| 24.1 | 28.65 |
| 24.6 | 20.05 |
| 25.1 | 28.24 |
| 25.3 | 31.05 |
| 25.8 | 35.64 |
| 26.4 | 35.12 |
| 26.7 | 28.61 |
| 27.8 | 31.13 |
| 28.7 | 25.99 |
| 29.2 | 25.20 |
| 30.6 | 14.61 |
| 31.5 | 19.08 |
| 32.2 | 8.81 |
| 32.7 | 8.36 |
| 36.7 | 2.96 |
| 37.2 | 4.34 |

Example 6: Preparation of Crystalline THF Solvate Form I of Compound 1

The crystalline THF solvate Form I of Compound 1 was prepared by placing amorphous Compound 1 in a small open vial then placing this vial inside a larger vial containing THF and capped to vapor stress the solids at RT for 4 days.

DSC endotherm onset of about 165° C., TGA comprising an approximate 13.4% weight loss when heated from about 130° C. to about 160° C. (1.2 mol THF)

NMR 1.1 mol THF

Figure 22:
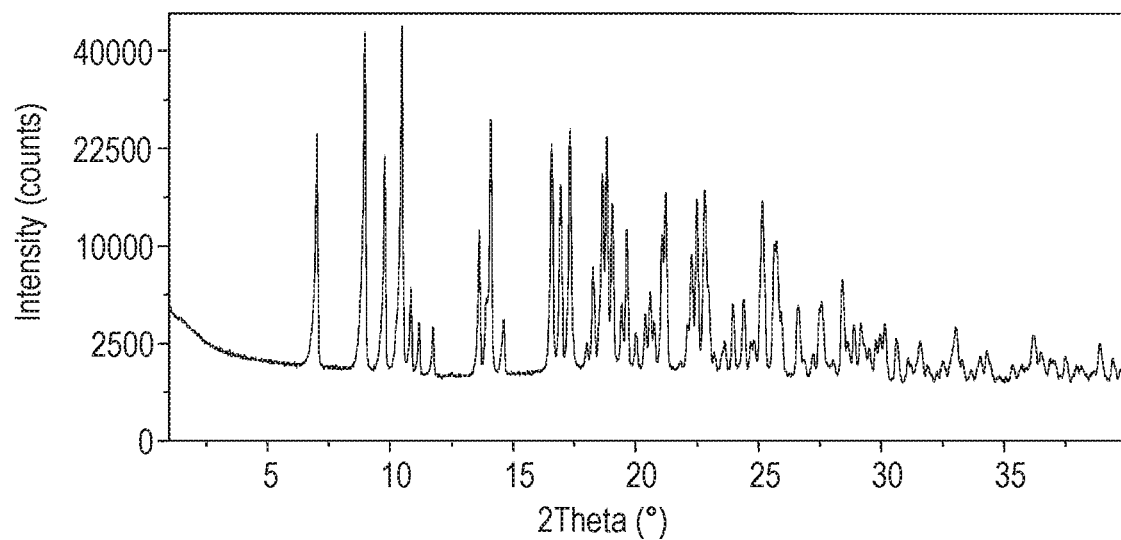
FIG. 22 shows XRPD data for the crystalline THF Solvate Form I of Compound 1.
Figure 23:
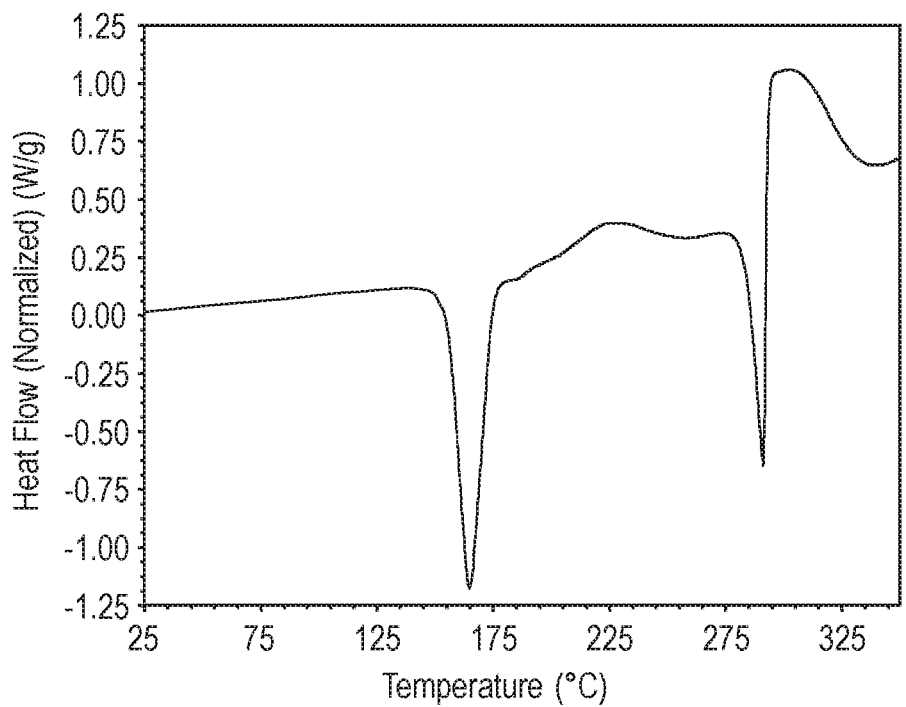
FIG. 23 shows DSC data for the crystalline THF Solvate Form I of Compound 1.
Figure 24:
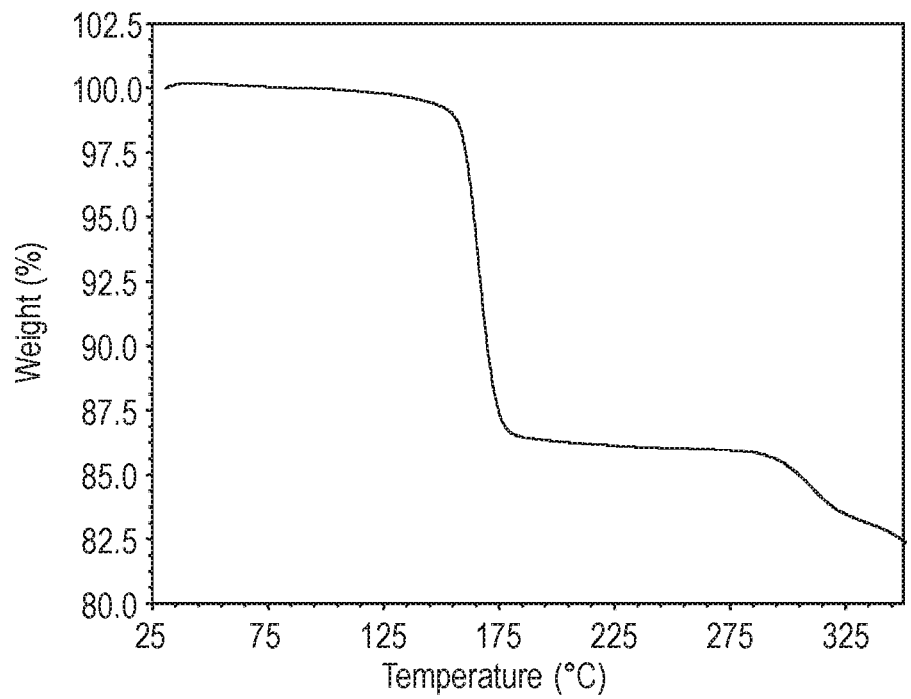
FIG. 24 shows TGA data for the crystalline THF Solvate Form I of Compound 1.

The crystalline THF solvate Form I prepared above was characterized by proton NMR, X-ray powder diffraction (XRPD) data (FIG. 22), DSC (FIG. 23), and TGA (FIG. 24).

$^1$H NMR (400 MHz, DMSO-$d_6$) δ ppm 0.94 (d, J=6.62 Hz, 3 H) 1.08 (d, J=6.62 Hz, 3 H) 1.35 (d, J=6.62 Hz, 3 H) 1.68-1.84 (m, 4 H) 1.90 (s, 3 H) 2.62-2.93 (m, 1 H) 3.15 (br t, J=11.33 Hz, 1 H) 3.49-3.75 (m, 10 H) 3.87-4.09 (m, 1 H) 4.09-4.21 (m, 1 H) 4.22-4.47 (m, 4 H) 4.91 (br s, 2 H) 5.71-5.83 (m, 2 H) 6.21 (br dd, J=16.88, 4.70 Hz, 1 H) 6.64-6.78 (m, 3 H) 6.78-6.99 (m, 1 H) 7.14-7.22 (m, 1 H) 7.28 (td, J=8.33, 7.05 Hz, 1 H) 8.18-8.35 (m, 1 H) 8.39 (d, J=4.92 Hz, 1 H) 10.21 (br s, 1 H)

TABLE 6

XRPD data of the Crystalline THF solvate Form I of Compound 1
XRPD Peak Table:

| Pos. [°2Th.] | Rel. Int. [%] |
|---|---|
| 7.0 | 54.90 |
| 9.0 | 100.00 |
| 9.8 | 46.41 |
| 10.3 | 5.55 |
| 10.5 | 99.74 |
| 10.9 | 11.45 |
| 11.2 | 5.67 |
| 11.8 | 5.10 |
| 13.7 | 24.35 |
| 14.0 | 9.45 |
| 14.1 | 59.90 |
| 14.7 | 6.49 |
| 16.6 | 52.03 |
| 17.0 | 37.49 |
| 17.3 | 56.50 |
| 18.0 | 3.30 |
| 18.3 | 16.05 |
| 18.7 | 41.48 |
| 18.8 | 54.81 |
| 19.1 | 31.94 |
| 19.4 | 8.97 |
| 19.7 | 25.38 |
| 20.0 | 4.56 |
| 20.4 | 7.31 |
| 20.6 | 11.11 |
| 20.8 | 6.26 |
| 21.1 | 22.76 |
| 21.2 | 34.92 |
| 22.1 | 5.75 |
| 22.3 | 18.70 |
| 22.5 | 33.36 |
| 22.8 | 36.37 |
| 23.0 | 10.85 |
| 23.2 | 2.20 |
| 23.6 | 3.63 |
| 24.0 | 9.03 |
| 24.4 | 9.86 |
| 24.7 | 3.54 |
| 24.8 | 3.71 |
| 25.2 | 32.94 |
| 25.6 | 20.13 |
| 25.8 | 21.45 |
| 26.0 | 7.67 |
| 26.6 | 8.01 |
| 26.9 | 1.62 |
| 27.3 | 2.20 |
| 27.5 | 7.64 |
| 27.6 | 9.42 |
| 28.1 | 1.43 |
| 28.4 | 13.20 |
| 28.7 | 3.64 |
| 28.9 | 5.81 |
| 29.2 | 5.97 |
| 29.5 | 2.80 |

TABLE 6-continued

XRPD data of the Crystalline THF solvate Form I of Compound 1
XRPD Peak Table:

| Pos. [°2Th.] | Rel. Int. [%] |
|---|---|
| 29.8 | 3.78 |
| 30.0 | 4.57 |
| 30.2 | 5.86 |
| 30.6 | 3.73 |
| 31.1 | 1.64 |
| 31.6 | 3.62 |
| 31.9 | 1.07 |
| 32.5 | 1.55 |
| 33.1 | 5.45 |
| 33.3 | 1.71 |
| 33.7 | 0.66 |
| 34.1 | 2.01 |
| 34.3 | 2.49 |
| 35.4 | 1.19 |
| 35.7 | 1.20 |
| 36.2 | 4.29 |
| 36.3 | 4.30 |
| 36.5 | 2.51 |
| 36.9 | 1.70 |
| 37.1 | 1.30 |
| 37.5 | 2.10 |
| 38.0 | 1.09 |
| 38.2 | 1.05 |
| 38.9 | 3.39 |
| 39.4 | 1.73 |

Example 7: Preparation of Crystalline MeCN Solvate Form I of Compound 1

The crystalline MeCN solvate Form I was prepared by slurry of compound 1 in MeCN at RT for 14 days.

DSC endotherm onset of about 112° C., TGA comprising an approximate 6.9% weight loss when heated from about 38° C. to about 170° C. (1 mol MeCN).

NMR 0.9 mol MeCN.

Figure 25:
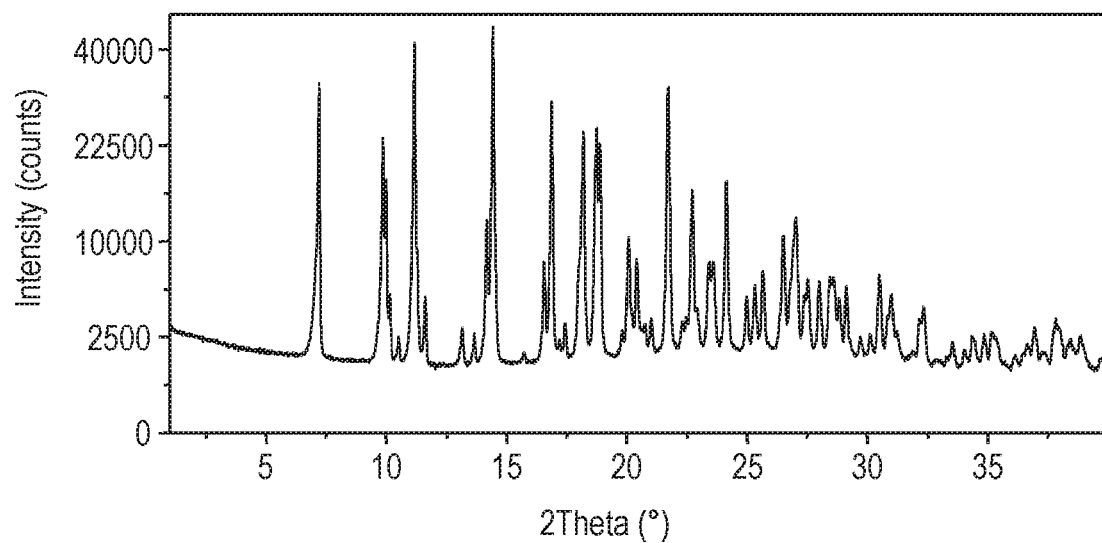
FIG. 25 shows XRPD data for the crystalline MeCN Solvate Form I of Compound 1.
Figure 26:
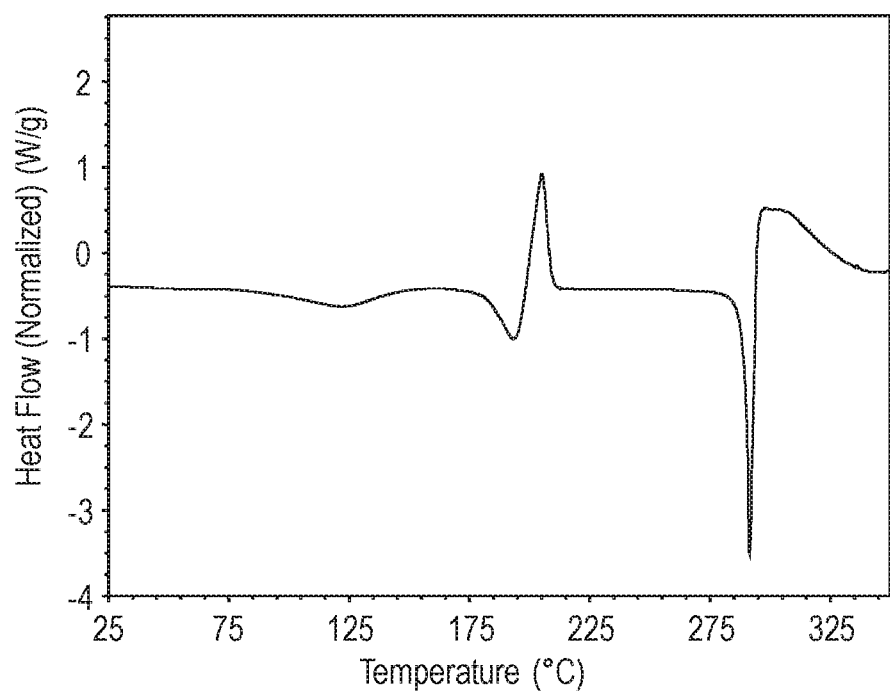
FIG. 26 shows DSC data for the crystalline MeCN Solvate Form I of Compound 1.
Figure 27:
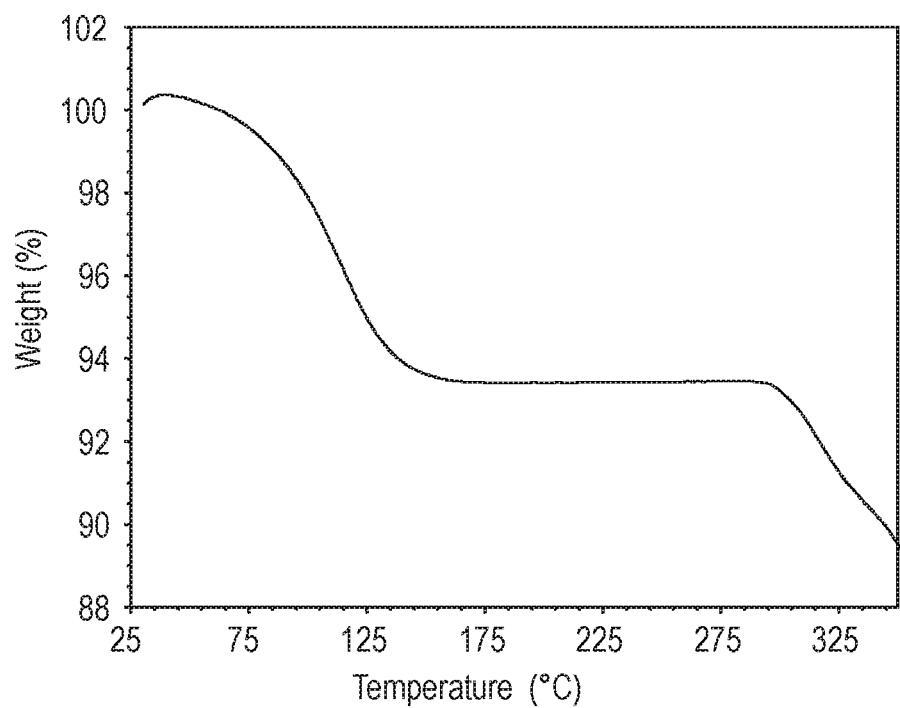
FIG. 27 shows TGA data for the crystalline MeCN Solvate Form I of Compound 1.

The crystalline MeCN solvate Form I prepared above was characterized by proton NMR, X-ray powder diffraction (XRPD) data (FIG. 25), DSC (FIG. 26), and TGA (FIG. 27).

$^1$H NMR (400 MHz, DMSO-$d_6$) δ ppm 0.85-1.00 (m, 3 H) 1.07 (d, J=6.82 Hz, 3 H) 1.35 (d, J=6.82 Hz, 3 H) 1.90 (s, 3 H) 1.99-2.16 (m, 2 H) 2.52-2.78 (m, 1 H) 3.14 (br s, 1 H) 3.35-3.56 (m, 1 H) 3.57-3.84 (m, 2 H) 3.86-4.09 (m, 1 H) 4.09-4.19 (m, 1 H) 4.19-4.47 (m, 2 H) 4.90 (br s, 1 H) 5.66-5.80 (m, 1 H) 6.20 (br dd, J=16.73, 4.58 Hz, 1 H) 6.61-6.76 (m, 2 H) 6.78-6.94 (m, 1 H) 7.11-7.21 (m, 1 H) 7.21-7.31 (m, 1 H) 8.16-8.36 (m, 2 H) 8.39 (d, J=4.69 Hz, 1 H) 10.21 (br s, 1 H).

TABLE 7

XRPD data of the Crystalline MeCN solvate Form I of Compound 1
XRPD Peak Table:

| Pos. [°2Th.] | Rel. Int. [%] |
|---|---|
| 7.2 | 72.45 |
| 9.9 | 52.43 |
| 10.0 | 37.15 |
| 10.2 | 8.87 |
| 10.5 | 2.74 |
| 11.2 | 91.77 |
| 11.3 | 15.89 |
| 11.6 | 8.89 |
| 13.2 | 4.06 |
| 13.7 | 3.17 |
| 14.2 | 25.71 |
| 14.5 | 100.00 |

TABLE 7-continued

XRPD data of the Crystalline MeCN solvate Form I of Compound 1
XRPD Peak Table:

| Pos. [°2Th.] | Rel. Int. [%] |
|---|---|
| 15.7 | 1.02 |
| 16.6 | 15.62 |
| 16.9 | 66.32 |
| 17.2 | 2.44 |
| 17.4 | 4.61 |
| 18.0 | 14.01 |
| 18.2 | 53.02 |
| 18.7 | 56.63 |
| 18.9 | 49.31 |
| 19.8 | 3.70 |
| 20.1 | 21.31 |
| 20.4 | 16.05 |
| 20.8 | 4.63 |
| 21.0 | 5.42 |
| 21.7 | 73.71 |
| 22.3 | 5.02 |
| 22.5 | 5.69 |
| 22.7 | 34.41 |
| 23.0 | 6.77 |
| 23.4 | 15.57 |
| 23.6 | 15.11 |
| 24.1 | 37.36 |
| 25.0 | 8.92 |
| 25.3 | 10.74 |
| 25.7 | 13.79 |
| 26.5 | 21.93 |
| 26.8 | 9.15 |
| 27.0 | 26.55 |
| 27.4 | 8.80 |
| 27.5 | 12.09 |
| 28.0 | 11.68 |
| 28.4 | 12.41 |
| 28.6 | 11.67 |
| 28.8 | 8.71 |
| 29.1 | 10.79 |
| 29.7 | 3.00 |
| 30.1 | 3.21 |
| 30.5 | 13.17 |
| 30.8 | 5.66 |
| 31.0 | 9.44 |
| 31.2 | 3.79 |
| 31.9 | 1.38 |
| 32.2 | 5.20 |
| 32.3 | 7.29 |
| 33.5 | 2.46 |
| 34.0 | 1.40 |
| 34.4 | 2.91 |
| 34.9 | 3.17 |
| 35.2 | 3.57 |
| 35.4 | 2.40 |
| 36.2 | 0.94 |
| 36.6 | 2.12 |
| 37.0 | 4.21 |
| 37.7 | 3.05 |
| 37.9 | 5.41 |
| 38.0 | 3.75 |
| 38.5 | 2.87 |
| 38.9 | 3.18 |

Example 8: Preparation of Crystalline MEK Solvate Form I of Compound 1

The crystalline MEK solvate Form I was prepared by dissolving Compound 1 in MEK at RT, polish filtering then charging with aliquots of heptane as an antisolvent until precipitation occurred. Solids were isolated after stirring at RT for 13 days. Also prepared by slurry of amorphous Compound 1 in MEK at RT.

DSC endotherm onset of about 106° C., TGA comprising an approximate 10.7% weight loss when heated from about 39° C. to about 197° C. (0.9 mol MEK)

NMR 0.8 mol MEK.

Figure 28:
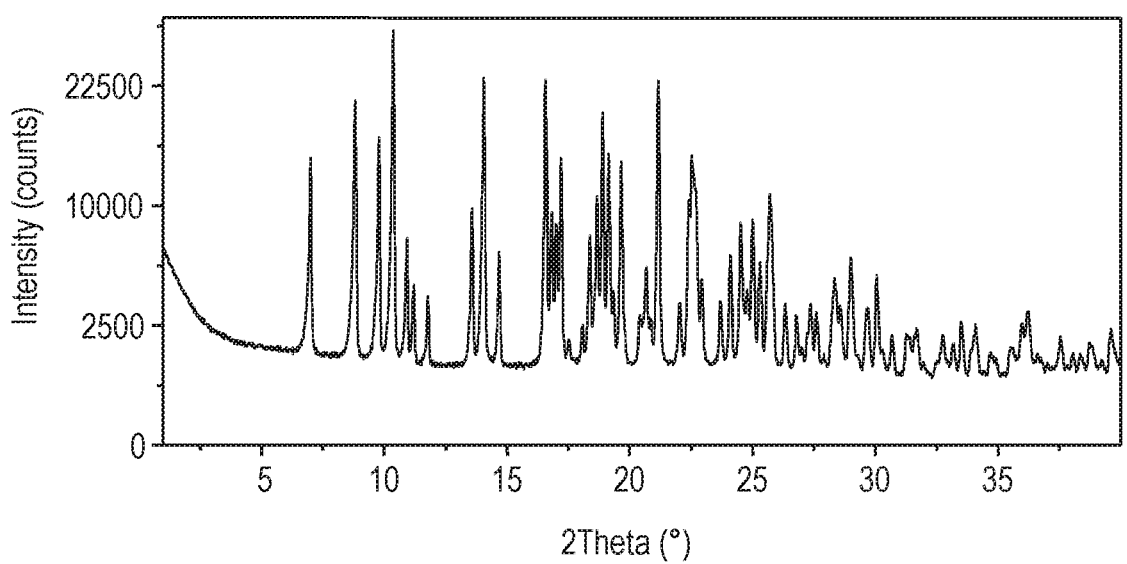
FIG. 28 shows XRPD data for the crystalline MEK Solvate Form I of Compound 1.
Figure 29:
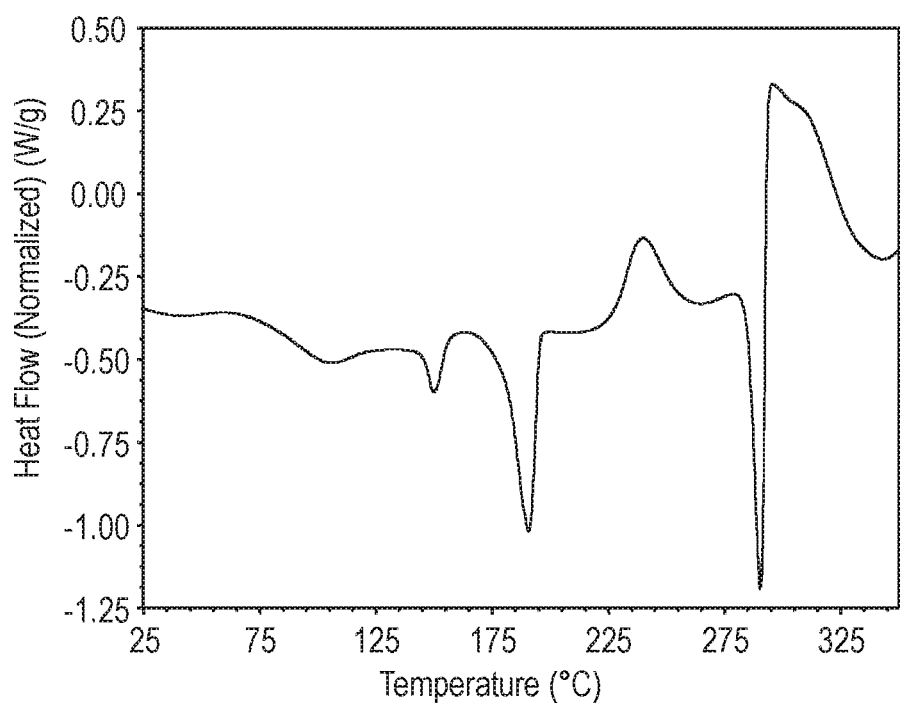
FIG. 29 shows DSC data for the crystalline MEK Solvate Form I of Compound 1
Figure 30:
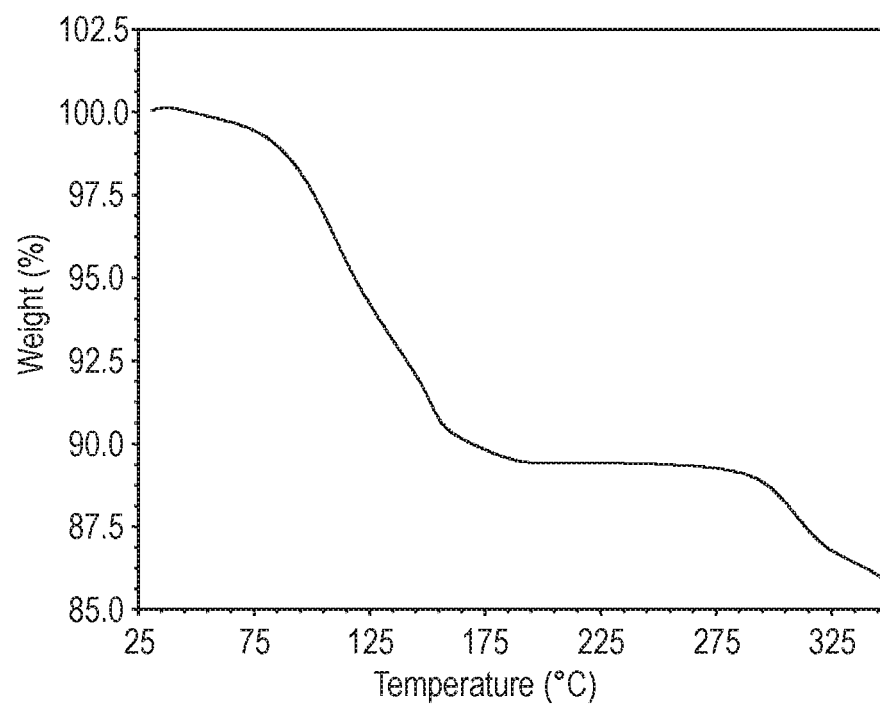
FIG. 30 shows TGA data for the crystalline MEK Solvate Form I of Compound 1.

The crystalline MEK solvate Form I prepared above was characterized by proton NMR, X-ray powder diffraction (XRPD) data (FIG. 28), DSC (FIG. 29), and TGA (FIG. 30).

$^1$H NMR (400 MHz, DMSO-d$_6$) δ ppm 0.92 (q, J=7.05 Hz, 5 H) 1.08 (d, J=6.62 Hz, 3 H) 1.35 (d, J=6.62 Hz, 3 H) 1.90 (s, 3 H) 2.04-2.10 (m, 2 H) 2.36-2.49 (m, 2 H) 2.60-2.93 (m, 1 H) 3.15 (br s, 1 H) 3.36-3.57 (m, 2 H) 3.57-3.84 (m, 4 H) 3.86-4.09 (m, 2 H) 4.15 (br d, J=12.82 Hz, 1 H) 4.22-4.46 (m, 4 H) 4.91 (br s, 2 H) 5.72-5.83 (m, 2 H) 6.00-6.21 (m, 1 H) 6.23 (br d, J=4.49 Hz, 1 H) 6.64-6.78 (m, 3 H) 6.78-7.00 (m, 2 H) 7.17-7.31 (m, 3 H) 8.16-8.35 (m, 1 H) 8.39 (d, J=4.92 Hz, 1 H) 10.22 (br s, 1 H).

TABLE 8

XRPD data of the Crystalline MEK solvate Form I of Compound 1
XRPD Peak Table:

| Pos. [°2Th.] | Rel. Int. [%] |
|---|---|
| 7.0 | 47.52 |
| 8.8 | 70.25 |
| 9.8 | 56.17 |
| 10.4 | 100.00 |
| 10.9 | 22.80 |
| 11.2 | 11.60 |
| 11.8 | 9.64 |
| 13.6 | 31.04 |
| 14.1 | 78.89 |
| 14.7 | 19.18 |
| 16.6 | 79.53 |
| 16.8 | 30.39 |
| 17.0 | 26.79 |
| 17.2 | 47.48 |
| 17.5 | 3.12 |
| 18.1 | 5.01 |
| 18.4 | 23.39 |
| 18.7 | 35.48 |
| 18.9 | 65.12 |
| 19.2 | 48.49 |
| 19.4 | 10.83 |
| 19.7 | 46.72 |
| 20.4 | 6.72 |
| 20.7 | 15.78 |
| 20.9 | 6.30 |
| 21.2 | 80.14 |
| 22.1 | 8.83 |
| 22.4 | 32.98 |
| 22.6 | 48.82 |
| 22.7 | 34.64 |
| 22.9 | 13.33 |
| 23.7 | 9.34 |
| 24.1 | 18.80 |
| 24.5 | 27.07 |
| 24.8 | 11.35 |
| 25.0 | 28.12 |
| 25.3 | 17.14 |
| 25.7 | 36.16 |
| 25.8 | 25.93 |
| 26.3 | 8.43 |
| 26.8 | 6.92 |
| 27.0 | 2.12 |
| 27.2 | 3.88 |
| 27.4 | 8.69 |
| 27.6 | 7.15 |
| 27.9 | 1.14 |
| 28.2 | 6.71 |
| 28.3 | 13.70 |
| 28.6 | 8.63 |
| 29.0 | 18.29 |
| 29.6 | 7.09 |
| 30.1 | 14.00 |
| 30.3 | 2.13 |
| 30.7 | 3.85 |

TABLE 8-continued

XRPD data of the Crystalline MEK solvate Form I of Compound 1
XRPD Peak Table:

| Pos. [°2Th.] | Rel. Int. [%] |
|---|---|
| 31.3 | 3.80 |
| 31.71 | 4.92 |
| 32.0 | 0.54 |
| 32.5 | 0.62 |
| 32.8 | 4.00 |
| 33.2 | 2.69 |
| 33.5 | 5.80 |
| 34.1 | 5.30 |
| 34.7 | 1.61 |
| 35.0 | 0.76 |
| 35.5 | 2.20 |
| 36.0 | 5.55 |
| 36.2 | 7.66 |
| 36.6 | 1.43 |
| 37.0 | 0.51 |
| 37.5 | 3.76 |
| 38.1 | 1.54 |
| 38.4 | 1.60 |
| 38.7 | 2.93 |
| 39.3 | 0.73 |
| 39.6 | 4.20 |

Example 9: Preparation of the Crystalline EtOAc Solvate Form I of Compound 1

The crystalline EtOAc Solvate Form I was prepared by a slurry of Compound 1 with ethyl acetate (EtOAc) at RT for 24 h.

Figure 31:
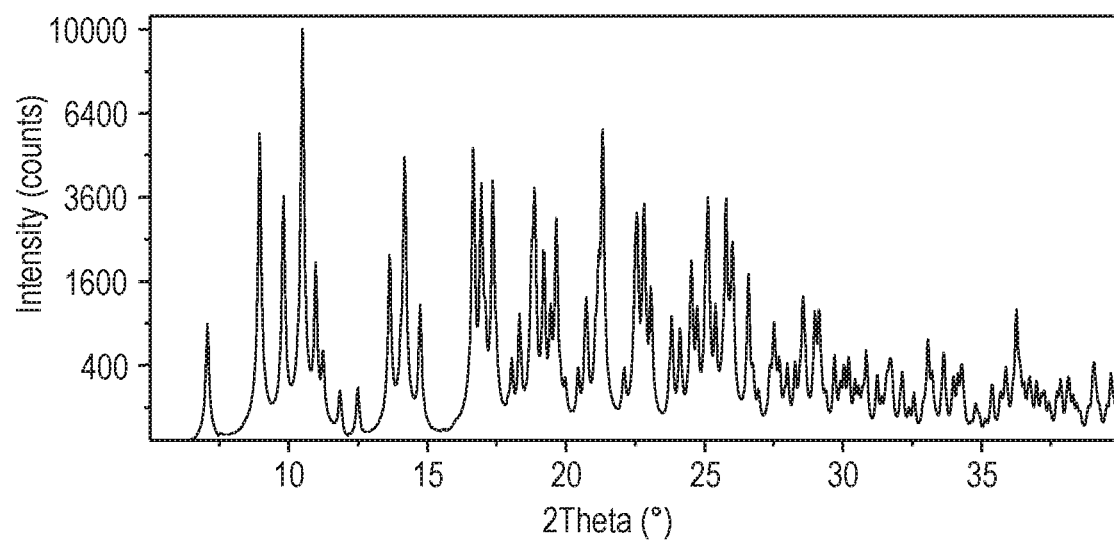
FIG. 31 shows XRPD data for the crystalline EtOAc Solvate Form I of Compound 1.

The crystalline MEK solvate Form I prepared above was characterized by proton NMR and X-ray powder diffraction (XRPD) data (FIG. 31).

TABLE 9

XRPD data of crystalline EtOAc Solvate Form I of Compound 1:
XRPD Peak Table:

| Pos. [°2Th.] | Rel. Int. [%] |
|---|---|
| 7.1 | 8.9 |
| 9.0 | 55.8 |
| 9.8 | 36.0 |
| 10.5 | 100.0 |
| 11.0 | 19.6 |
| 11.3 | 5.6 |
| 11.9 | 1.9 |
| 12.5 | 2.2 |
| 13.7 | 21.3 |
| 14.2 | 48.6 |
| 14.7 | 11.8 |
| 16.7 | 51.6 |
| 17.0 | 39.5 |
| 17.4 | 40.6 |
| 18.1 | 4.6 |
| 18.3 | 10.5 |
| 18.9 | 38.1 |
| 19.2 | 23.2 |
| 19.5 | 11.8 |
| 19.7 | 30.5 |
| 20.0 | 2.9 |
| 20.4 | 3.8 |
| 20.7 | 12.9 |
| 21.3 | 59.1 |
| 22.1 | 3.7 |
| 22.6 | 30.7 |
| 22.8 | 34.2 |
| 23.1 | 14.8 |
| 23.8 | 9.9 |
| 24.1 | 8.2 |
| 24.5 | 19.9 |
| 24.8 | 11.5 |
| 25.1 | 35.4 |
| 25.4 | 11.8 |
| 25.8 | 35.3 |
| 26.0 | 24.8 |
| 26.6 | 17.1 |
| 27.0 | 2.0 |
| 27.5 | 9.1 |
| 27.7 | 4.7 |
| 28.0 | 4.2 |
| 28.6 | 13.0 |
| 29.0 | 10.6 |
| 29.2 | 10.9 |
| 29.7 | 5.0 |
| 30.2 | 4.8 |
| 30.9 | 5.5 |
| 31.3 | 3.2 |
| 31.7 | 4.5 |
| 32.1 | 3.4 |
| 32.6 | 1.8 |
| 33.1 | 6.8 |
| 33.6 | 5.2 |
| 34.0 | 2.9 |
| 34.3 | 4.0 |
| 34.8 | 1.2 |
| 35.4 | 2.4 |
| 35.7 | 1.8 |
| 35.9 | 3.9 |
| 36.3 | 10.9 |
| 36.8 | 2.9 |
| 37.0 | 2.7 |
| 37.3 | 1.9 |
| 37.9 | 2.7 |
| 38.1 | 3.0 |
| 39.1 | 4.3 |
| 39.7 | 3.3 |
| 40.1 | 3.1 |
| 40.4 | 3.6 |
| 41.2 | 2.5 |
| 41.6 | 3.6 |
| 42.0 | 1.3 |
| 42.5 | 2.2 |
| 43.2 | 4.1 |
| 43.5 | 3.4 |
| 43.8 | 2.2 |
| 44.1 | 2.6 |
| 44.4 | 2.3 |

Example 10: Preparation of the DMf Solvate Form I of Compound 1

The crystalline DMF solvate Form I of Compound 1 was prepared by a slurry of Compound 1 in DMF/water at RT for 24 h.

Figure 32:
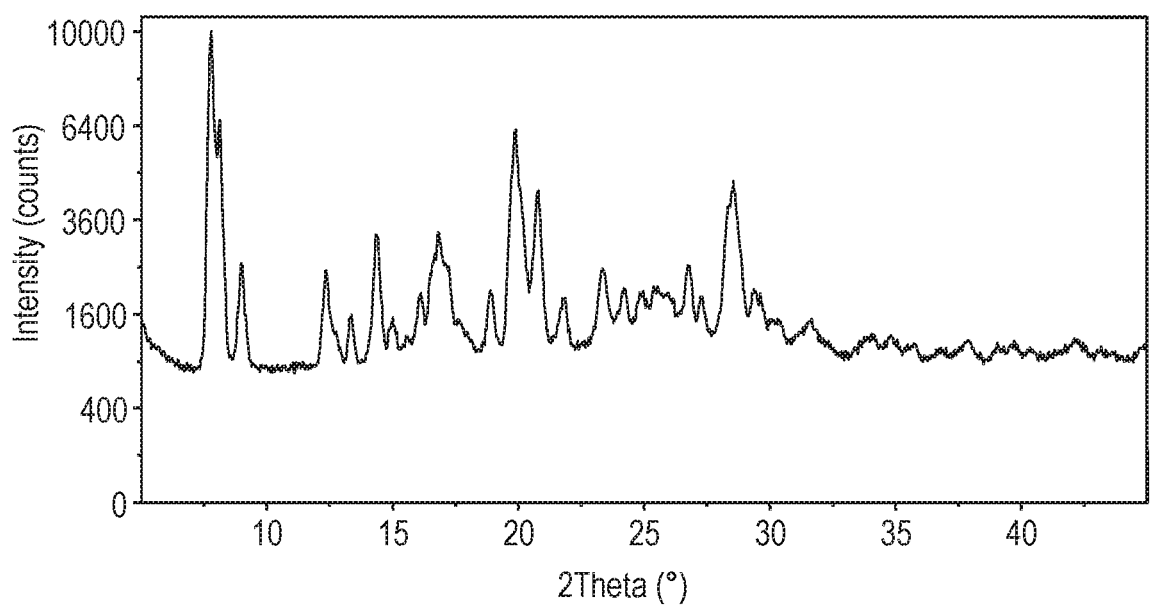
FIG. 32 shows XRPD data for the crystalline DMF Solvate Form I of Compound 1.
Figure 33:
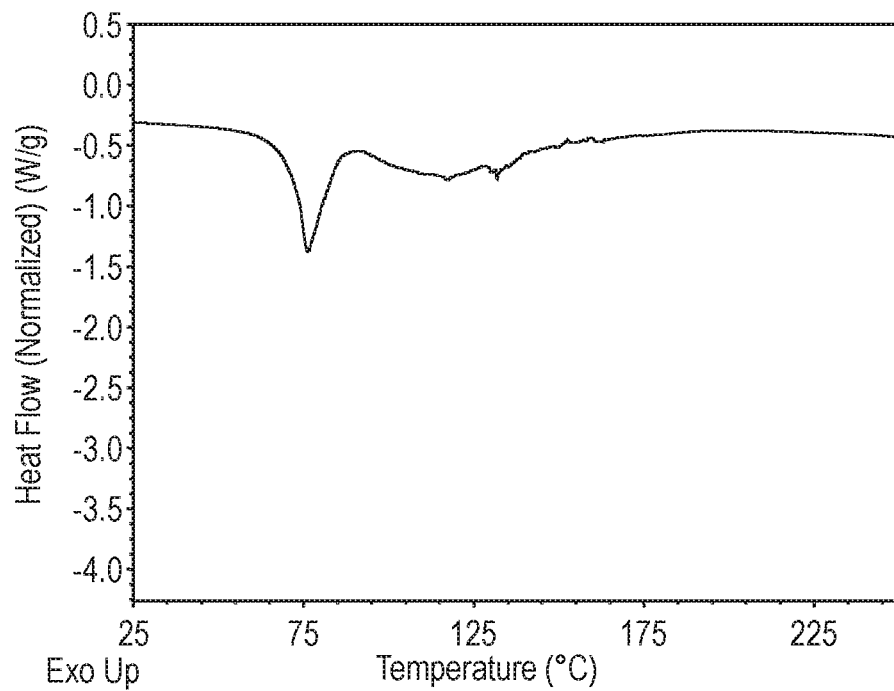
FIG. 33 shows DSC data for the crystalline DMF Solvate Form I of Compound 1.
Figure 34:
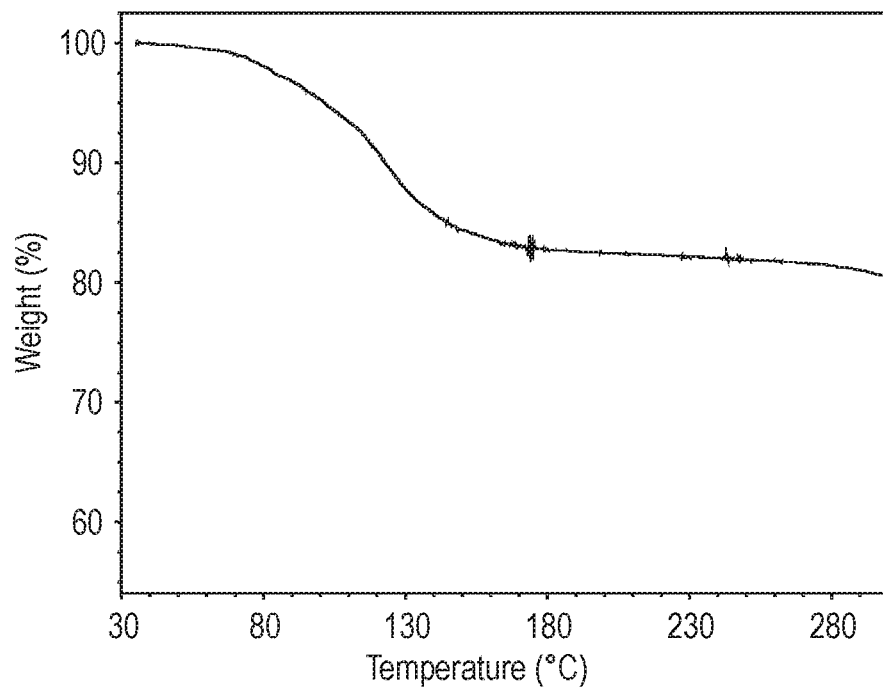
FIG. 34 shows TGA data for the crystalline DMF Solvate Form I of Compound 1.

The crystalline DMF solvate Form I of Compound 1 prepared above was characterized by proton NMR, X-ray powder diffraction (XRPD) data (FIG. 32), DSC (FIG. 33), and TGA (FIG. 34).

DSC endotherm onset of about 74° C., TGA comprising an approximate 17% weight loss when heated from about 36° C. to about 195° C.

NMR 1-2 mol DMF.

$^1$H NMR (500 MHz, DMSO-$d_6$) δ ppm 0.94 (d, J=6.49 Hz, 4 H) 1.08 (d, J=6.75 Hz, 4 H) 1.35 (d, J=6.75 Hz, 4 H) 1.91 (s, 4 H) 2.30 (s, 1 H) 2.55 (t, J=5.58 Hz, 1 H) 2.73 (s, 6 H) 2.89 (s, 5 H) 3.00-3.21 (m, 1 H) 3.27 (br d, J=13.49 Hz, 2 H) 3.34 (br s, 5 H) 3.60-3.74 (m, 2 H) 3.96-4.16 (m, 1H) 4.32 (br d, J=13.75 Hz, 2 H) 4.39 (br s, 1 H) 4.90 (br s, 1 H) 5.67-5.86 (m, 1 H) 6.20 (br dd, J=16.61, 7.27 Hz, 1 H)

6.64-6.77 (m, 2 H) 6.79-6.92 (m, 1 H) 7.17-7.32 (m, 2 H) 7.95 (s, 1 H) 8.28 (br dd, J=16.22, 9.21 Hz, 1 H) 8.40 (d, J=4.93 Hz, 1 H) 10.19 (d, J=1.30 Hz, 1 H).

TABLE 10

XRPD data of the Crystalline DMF Solvate Form I of Compound 1
XRPD Peak Table:

| Pos. [°2Th.] | Rel. Int. [%] |
| --- | --- |
| 7.8 | 100.0 |
| 8.1 | 60.0 |
| 9.0 | 19.1 |
| 12.4 | 17.5 |
| 13.3 | 7.5 |
| 14.4 | 25.9 |
| 15.0 | 7.4 |
| 16.1 | 11.4 |
| 16.8 | 26.5 |
| 17.3 | 17.5 |
| 18.9 | 12.3 |
| 19.9 | 58.6 |
| 20.8 | 38.6 |
| 21.8 | 11.0 |
| 23.3 | 17.0 |
| 24.3 | 12.6 |
| 24.9 | 11.5 |
| 25.4 | 12.7 |
| 26.8 | 17.8 |
| 27.3 | 11.1 |
| 28.3 | 30.4 |
| 28.6 | 38.6 |
| 29.4 | 12.3 |
| 30.4 | 6.0 |
| 31.6 | 6.2 |
| 34.0 | 3.3 |
| 35.7 | 1.9 |
| 37.9 | 2.6 |
| 42.2 | 2.2 |

Example 11: Preparation of the Crystalline DCM Solvate Form I of Compound 1

The crystalline DCM solvate Form I of Compound 1 was prepared by dissolving Compound 1 in DCM at RT, polish filtering, then charging the aliquots of heptane as an anti-solvent until precipitation occurred. Solids were isolated after stirring at RT for 1 h.

$^1$H NMR (400 MHz, DMSO-$d_6$) δ ppm 0.84-1.02 (m, 2 H) 1.07 (d, J=6.61 Hz, 2 H) 1.35 (d, J=6.82 Hz, 2 H) 1.90 (s, 2 H) 2.64-2.80 (m, 1 H) 3.14 (br t, J=11.19 Hz, 1 H) 3.45-3.57 (m, 1 H) 3.58-3.84 (m, 2 H) 3.86-4.09 (m, 1 H) 4.09-4.21 (m, 1 H) 4.21-4.46 (m, 2 H) 4.90 (br s, 1 H) 5.65-5.86 (m, 2 H) 6.08-6.28 (m, 1 H) 6.63-6.76 (m, 2 H) 6.86 (dt, J=16.46, 11.27 Hz, 1 H) 7.12-7.21 (m, 1 H) 7.21-7.31 (m, 1 H) 8.16-8.36 (m, 2 H) 8.39 (d, J=4.90 Hz, 1 H) 10.20 (br s, 1 H).

Figure 35:
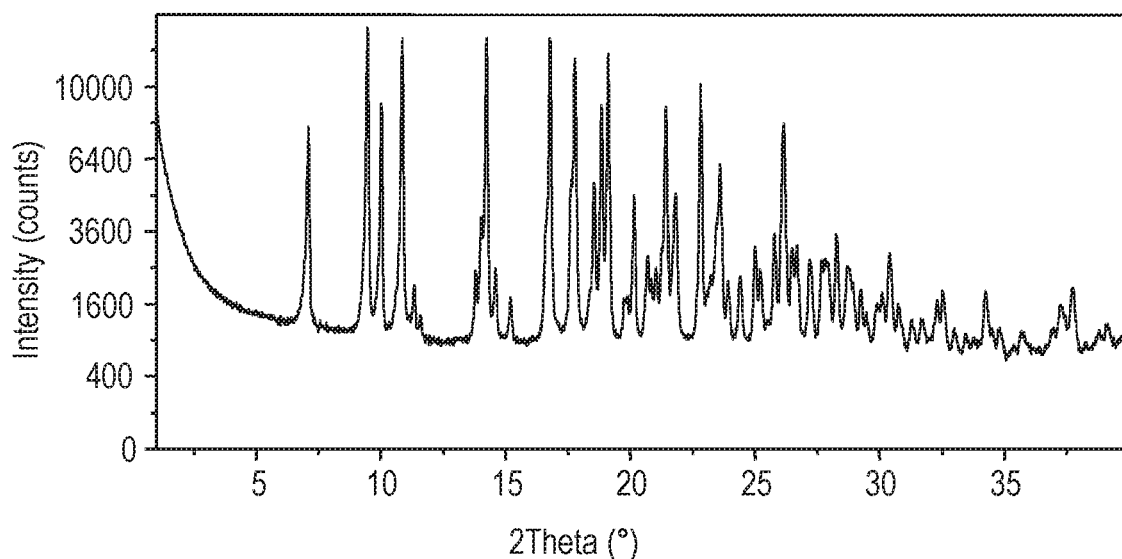
FIG. 35 shows XRPD data for the crystalline DCM Solvate Form I of Compound 1.
Figure 36:
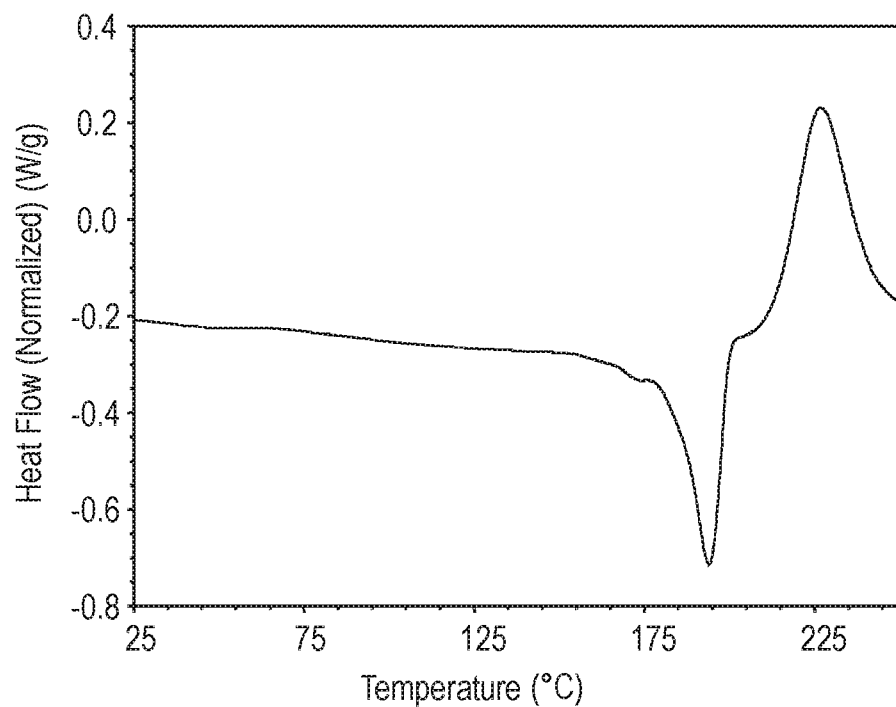
FIG. 36 shows DSC data for the crystalline DCM Solvate Form I of Compound 1
Figure 37:
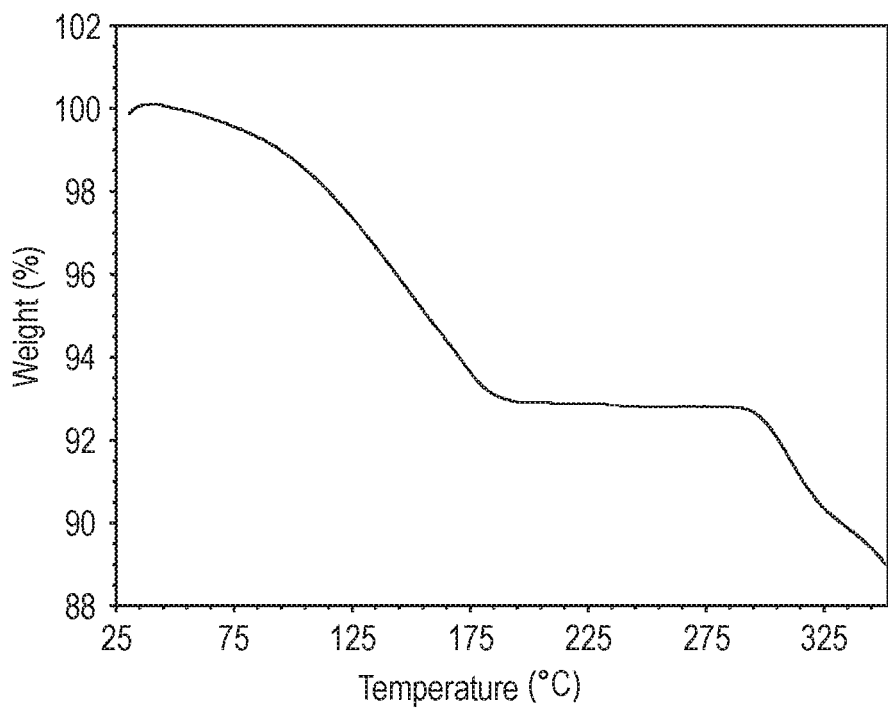
FIG. 37 shows TGA data for the crystalline DCM Solvate Form I of Compound 1.

The crystalline DCM solvate Form I of Compound 1 prepared above was characterized by proton NMR, X-ray powder diffraction (XRPD) data (FIG. 35), DSC (FIG. 36), and TGA (FIG. 37).

DSC endotherm onset of about 174° C., TGA comprising an approximate 7.2% weight loss when heated from about 40° C. to about 200° C. (0.5 mol DCM) from 40-200°.

NMR 0.5 mol DCM

TABLE 11

XRPD data of the Crystalline DCM Solvate Form I of Compound 1
XRPD Peak Table

| Pos. [°2Th.] | Rel. Int. [%] |
| --- | --- |
| 7.1 | 53.6 |
| 9.5 | 100.0 |
| 10.1 | 64.3 |
| 10.9 | 95.6 |
| 11.7 | 9.1 |
| 11.6 | 3.4 |
| 13.8 | 12.2 |
| 14.0 | 26.5 |
| 14.3 | 95.5 |
| 14.6 | 12.7 |
| 15.2 | 7.2 |
| 16.6 | 23.7 |
| 16.8 | 97.7 |
| 17.6 | 36.1 |
| 17.8 | 86.9 |
| 18.6 | 35.9 |
| 18.9 | 65.9 |
| 19.1 | 88.3 |
| 19.8 | 6.0 |
| 20.2 | 31.9 |
| 20.7 | 16.3 |
| 21.0 | 13.2 |
| 21.3 | 16.8 |
| 21.4 | 65.3 |
| 21.8 | 33.6 |
| 22.8 | 74.2 |
| 23.2 | 12.1 |
| 23.5 | 23.7 |
| 23.6 | 43.1 |
| 23.9 | 10.5 |
| 24.4 | 11.9 |
| 25.0 | 17.6 |
| 25.2 | 12.8 |
| 25.8 | 21.9 |
| 26.2 | 58.2 |
| 26.5 | 18.3 |
| 26.7 | 19.1 |
| 27.2 | 14.4 |
| 27.3 | 13.4 |
| 27.7 | 14.8 |
| 28.0 | 14.5 |
| 28.3 | 22.0 |
| 28.7 | 12.6 |
| 29.0 | 9.0 |
| 29.3 | 9.3 |
| 29.5 | 5.3 |
| 29.9 | 6.6 |
| 30.1 | 8.7 |
| 30.4 | 17.3 |
| 30.8 | 6.6 |
| 31.3 | 3.7 |
| 31.7 | 4.0 |
| 32.3 | 7.2 |
| 32.5 | 7.7 |
| 33.0 | 2.4 |
| 33.5 | 1.9 |
| 34.2 | 8.3 |
| 34.8 | 2.8 |
| 35.7 | 2.3 |
| 36.9 | 2.4 |
| 37.3 | 6.5 |
| 37.8 | 9.6 |
| 38.8 | 2.4 |
| 39.1 | 3.6 |

Example 12: Preparation of the Crystalline Acetone Solvate Form I of Compound 1

The crystalline acetone solvate Form I of Compound 1 was prepared by a slurry of amorphous Compound 1 in acetone/water (50:50) at RT or a slurry of Compound 1 in acetone/water (50:50) at 2-8° C. for 15 days.

Figure 38:
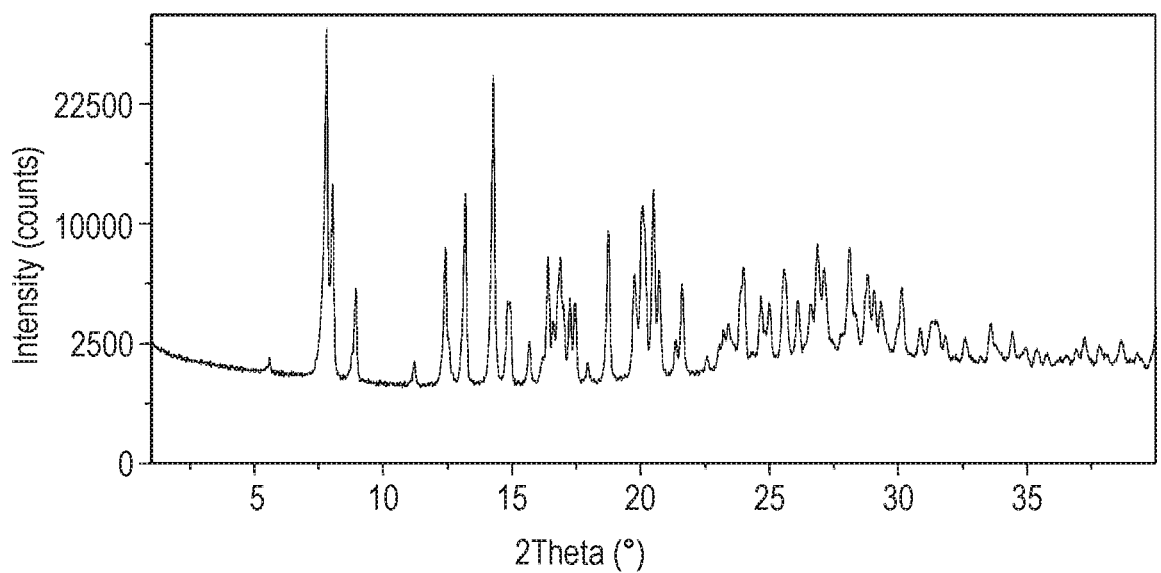
FIG. 38 shows XRPD data for the crystalline Acetone Solvate Form I of Compound 1.
Figure 39:
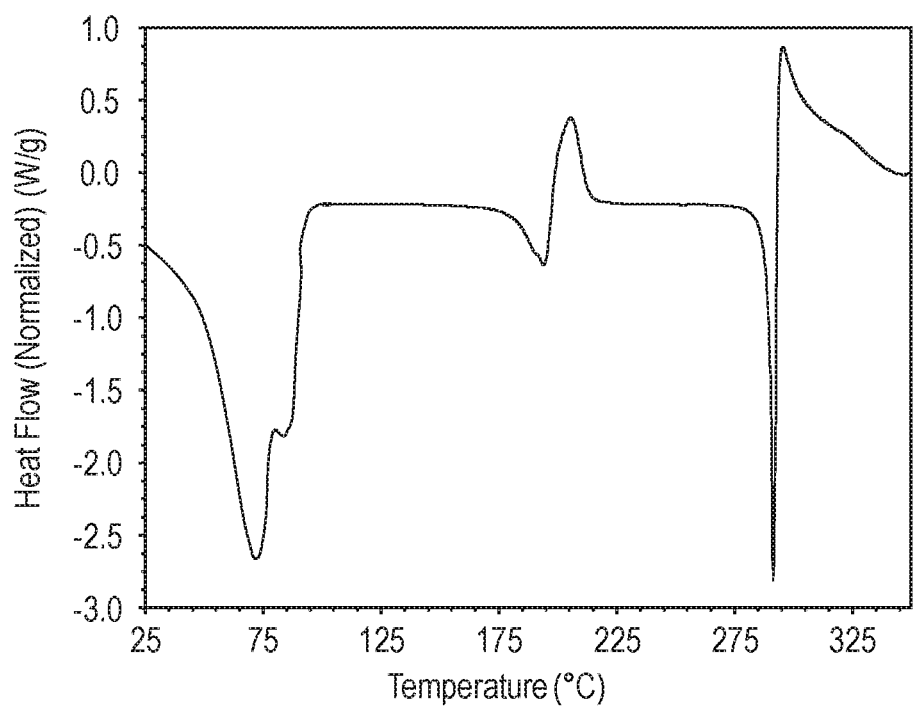
FIG. 39 shows DSC data for the crystalline Acetone Solvate Form I of Compound 1.
Figure 40:
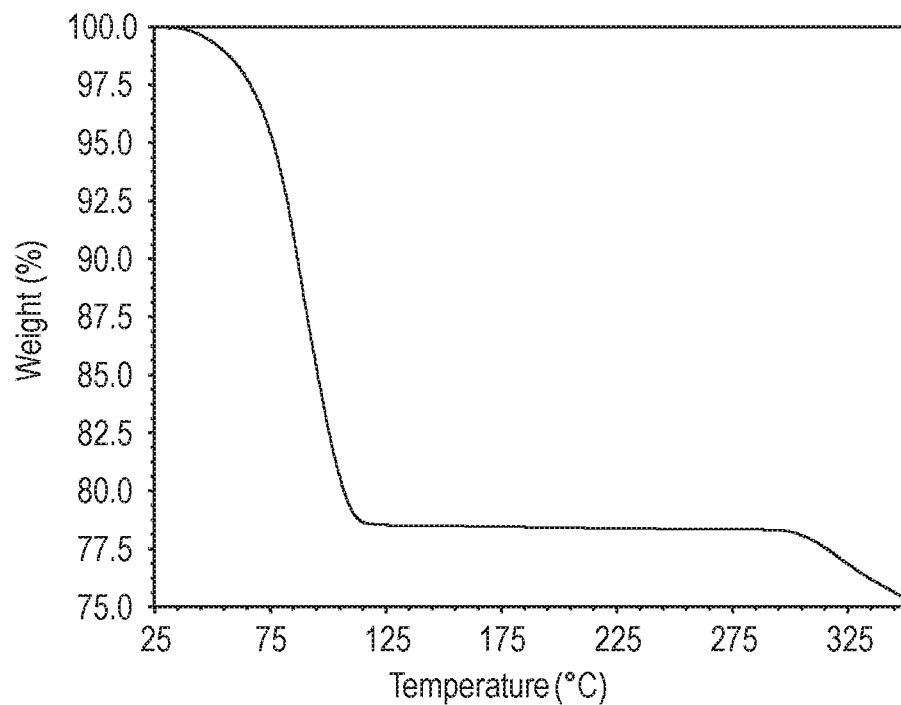
FIG. 40 shows TGA data for the crystalline Acetone Solvate Form I of Compound 1.

The crystalline acetone solvate Form I of Compound 1 prepared above was characterized by proton NMR, X-ray powder diffraction (XRPD) data (FIG. 38), DSC (FIG. 39), and TGA (FIG. 40).

DSC endotherm onset of about 72° C., TGA comprising an approximate 21.4% weight loss when heated from about 38° C. to about 130° C. (0.7 mol acetone and 5.3 mol water).

NMR 0.7 mol acetone.

$^1$NMR (400 MHz, DMSO-$d_6$) δ ppm 0.84-1.00 (m, 3 H) 1.07 (d, J=6.61 Hz, 3 H) 1.34 (d, J=6.61 Hz, 3 H) 1.90 (s, 3 H) 2.05-2.12 (m, 3 H) 2.52-2.78 (m, 2 H) 3.08-3.21 (m, 1 H) 3.45-3.57 (m, 1 H) 3.67 (br d, J=11.72 Hz, 2 H) 3.97-4.06 (m, 1 H) 4.08-4.21 (m, 1H) 4.32 (br d, J=13.85 Hz, 2 H) 4.90 (br s, 1 H) 5.54-5.80 (m, 2 H) 5.99-6.26 (m, 2 H) 6.52-6.75 (m, 2 H) 6.84 (br s, 1 H) 7.09-7.30 (m, 2 H) 8.12-8.36 (m, 3 H) 8.38 (d, J=4.90 Hz, 1 H) 10.21 (br s, 1 H).

TABLE 12

XRPD data of the Crystalline Acetone Solvate Form I of Compound 1 XRPD Peak Table

| Pos. [°2Th.] | Rel. Int. [%] |
| --- | --- |
| 5.6 | 1.4 |
| 7.8 | 100.0 |
| 8.1 | 38.3 |
| 9.0 | 13.1 |
| 11.2 | 2.3 |
| 12.4 | 22.1 |
| 12.6 | 4.9 |
| 13.2 | 36.5 |
| 14.3 | 78.7 |
| 14.9 | 10.7 |
| 15.0 | 10.1 |
| 15.7 | 4.7 |
| 16.4 | 20.2 |
| 16.6 | 7.7 |
| 16.8 | 12.4 |
| 16.9 | 19.6 |
| 17.0 | 9.4 |
| 17.3 | 11.5 |
| 17.5 | 10.8 |
| 18.0 | 2.1 |
| 18.8 | 26.4 |
| 19.8 | 16.6 |
| 20.1 | 32.6 |
| 20.2 | 24.2 |
| 20.5 | 37.7 |
| 20.7 | 17.3 |
| 21.4 | 5.0 |
| 21.6 | 14.4 |
| 22.6 | 2.7 |
| 23.1 | 4.1 |
| 23.2 | 6.4 |
| 23.4 | 7.3 |
| 23.9 | 12.0 |
| 24.0 | 17.6 |
| 24.7 | 11.9 |
| 25.0 | 10.8 |
| 25.6 | 15.7 |
| 26.1 | 11.1 |
| 26.6 | 10.6 |
| 26.9 | 22.9 |
| 27.1 | 17.5 |
| 27.8 | 5.7 |
| 28.1 | 22.0 |
| 28.4 | 8.6 |
| 28.8 | 16.2 |
| 29.1 | 13.0 |
| 29.4 | 10.9 |
| 30.2 | 13.5 |
| 30.9 | 6.5 |
| 31.3 | 7.7 |
| 31.6 | 7.3 |
| 31.9 | 5.6 |
| 32.6 | 4.9 |
| 33.2 | 2.9 |
| 33.6 | 7.3 |
| 34.5 | 6.2 |
| 35.0 | 3.8 |
| 35.4 | 3.7 |
| 35.8 | 3.3 |
| 36.6 | 2.9 |
| 36.9 | 3.8 |
| 37.3 | 5.3 |
| 37.8 | 4.0 |
| 38.7 | 4.5 |
| 39.3 | 3.2 |

Example 13: Preparation of the Crystalline Acetone Solvate Form II of Compound 1

The crystalline acetone solvate Form II of Compound 1 was prepared by a slurry Compound 1 in acetone at 2-8° C. for 15 days.

Figure 41:
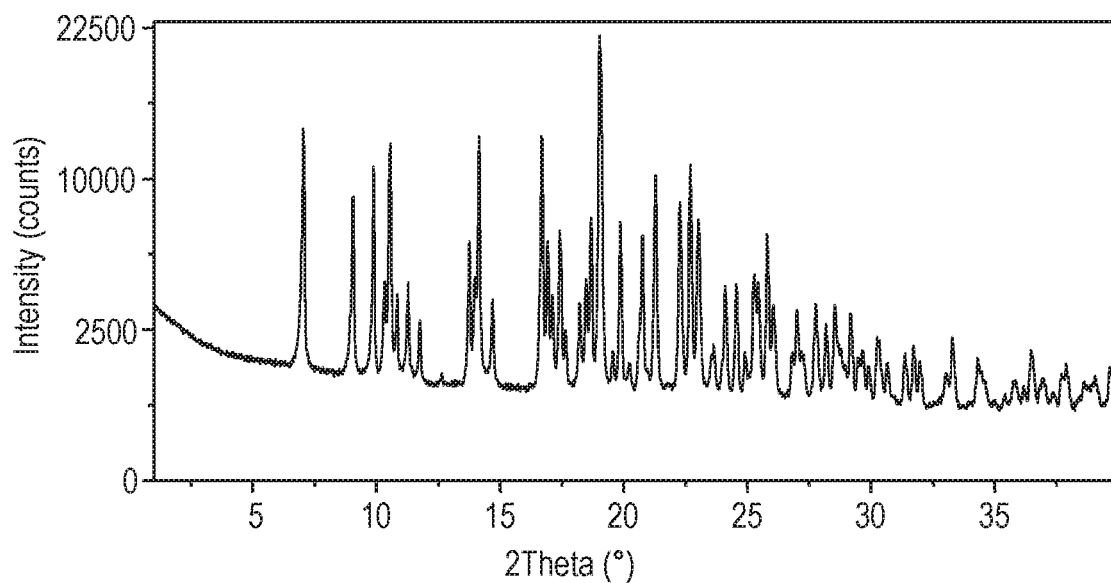
FIG. 41 shows XRPD data for the crystalline Acetone Solvate Form II of Compound 1.
Figure 42:
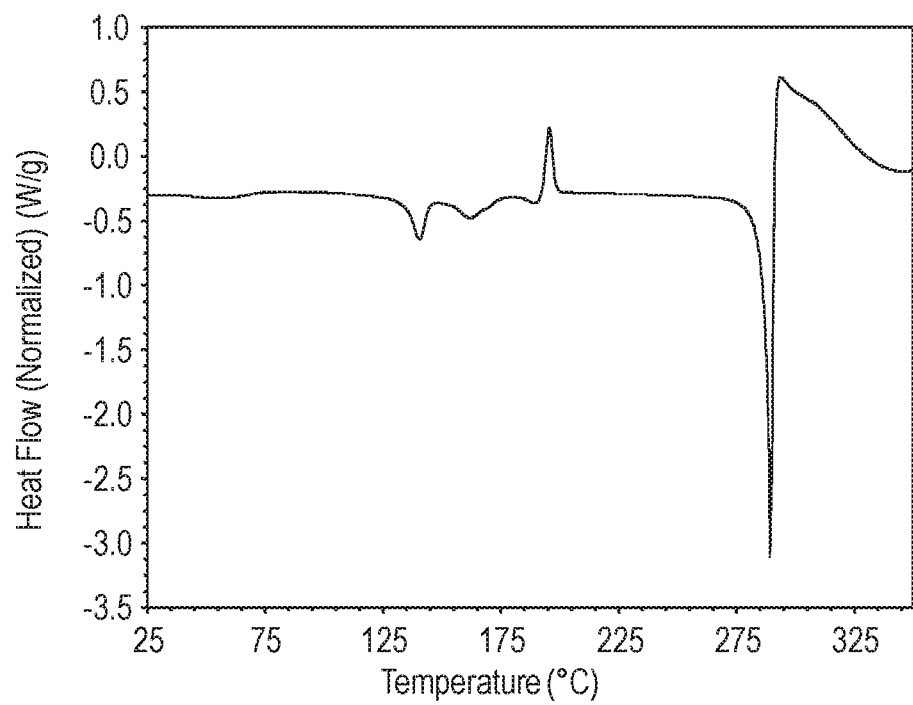
FIG. 42 shows DSC data for the crystalline Acetone Solvate Form II of Compound 1.
Figure 43:
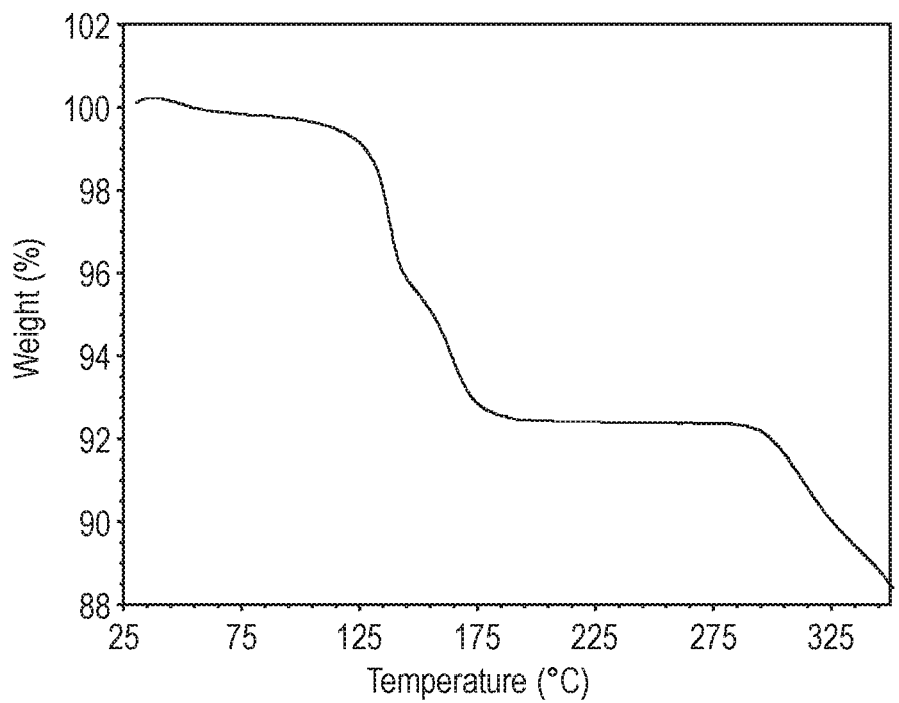
FIG. 43 shows TGA data for the crystalline Acetone Solvate Form II of Compound 1.

The crystalline acetone solvate Form II of Compound 1 prepared above was characterized by proton NMR, X-ray powder diffraction (XRPD) data (FIG. 41), DSC (FIG. 42), and TGA (FIG. 43).

DSC endotherm onset of about 137° C., TGA comprising an approximate 7.3% weight loss when heated from about 100° C. to about 200° C. (0.8 mol acetone).

NMR 0.7 mol acetone $^1$H NMR (400 MHz, DMSO-$d_6$) δ ppm 0.83-1.02 (m, 3 H) 1.07 (d, J=6.82 Hz, 2 H) 1.35 (d, J=6.61 Hz, 2 H) 1.90 (s, 2 H) 2.09 (s, 3 H) 2.52-2.77 (m, 1 H) 3.18 (br s, 1 H) 3.45-3.57 (m, 1 H) 3.66 (br s, 4 H) 3.96-4.08 (m, 1 H) 4.08-4.20 (m, 1 H) 4.32 (br d, J=13.64 Hz, 3 H) 4.90 (br s, 2 H) 5.69-5.80 (m, 1 H) 6.15-6.26 (m, 1 H) 6.60-6.75 (m, 2 H) 6.79-6.94 (m, 1 H) 7.07-7.21 (m, 1 H) 7.27 (td, J=8.31, 7.03 Hz, 1 H) 8.20-8.36 (m, 2 H) 8.39 (d, J=4.90 Hz, 1 H) 10.20 (br s, 1 H).

TABLE 13

XRPD data of the Crystalline Acetone Solvate Form II of Compound 1 XRPD Peak Table

| Pos. [°2Th.] | Rel. Int. [%] |
| --- | --- |
| 7.1 | 60.1 |
| 9.1 | 38.0 |
| 9.9 | 47.8 |
| 10.3 | 15.8 |
| 10.6 | 56.1 |
| 10.9 | 13.4 |
| 11.3 | 15.8 |
| 11.8 | 8.7 |
| 12.7 | 1.1 |
| 13.8 | 27.0 |
| 14.0 | 17.3 |
| 14.2 | 59.6 |
| 14.7 | 13.0 |
| 16.7 | 60.7 |
| 16.9 | 26.6 |
| 17.1 | 14.3 |
| 17.4 | 29.3 |
| 17.7 | 7.9 |
| 18.2 | 12.6 |
| 18.5 | 17.5 |
| 18.7 | 33.6 |
| 19.0 | 100.0 |
| 19.6 | 4.7 |
| 19.9 | 32.0 |

TABLE 13-continued

XRPD data of the Crystalline Acetone Solvate Form II of Compound 1
XRPD Peak Table

| Pos. [°2Th.] | Rel. Int. [%] |
|---|---|
| 20.3 | 3.3 |
| 20.8 | 29.1 |
| 21.3 | 46.3 |
| 22.3 | 37.3 |
| 22.7 | 50.5 |
| 23.0 | 32.6 |
| 23.7 | 5.9 |
| 24.1 | 16.5 |
| 24.6 | 17.2 |
| 24.9 | 5.0 |
| 25.3 | 18.9 |
| 25.5 | 17.5 |
| 25.8 | 29.5 |
| 26.1 | 13.0 |
| 26.8 | 4.9 |
| 27.0 | 12.0 |
| 27.3 | 4.9 |
| 27.8 | 13.6 |
| 28.2 | 9.8 |
| 28.6 | 12.5 |
| 28.8 | 5.9 |
| 29.2 | 11.7 |
| 29.5 | 4.8 |
| 29.7 | 5.9 |
| 29.9 | 3.7 |
| 30.3 | 7.0 |
| 30.7 | 7.2 |
| 30.7 | 4.2 |
| 31.4 | 5.2 |
| 31.7 | 6.6 |
| 32.0 | 4.5 |
| 33.1 | 2.9 |
| 33.3 | 7.6 |
| 34.3 | 4.9 |
| 35.4 | 0.8 |
| 35.7 | 2.3 |
| 36.2 | 1.7 |
| 36.5 | 6.2 |
| 37.0 | 2.4 |
| 37.4 | 1.0 |
| 37.7 | 2.8 |
| 37.9 | 4.2 |
| 38.6 | 2.1 |
| 39.1 | 2.8 |
| 39.7 | 3.8 |

Example 14: Preparation of the Crystalline P-Dioxane Solvate Form I of Compound 1

The crystalline p-dioxane solvate Form I of Compound 1 was prepared by a slurry of Compound 1 in p-dioxane at RT for 14 days.

Figure 44:
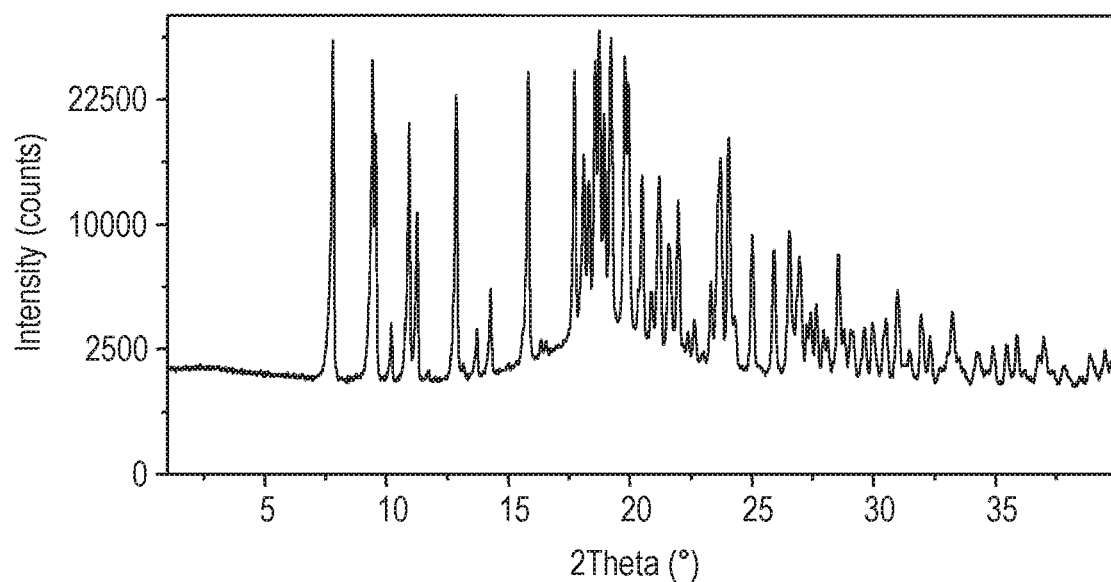
FIG. 44 shows XRPD data for the crystalline p-Dioxane Solvate Form I of Compound 1.
Figure 45:
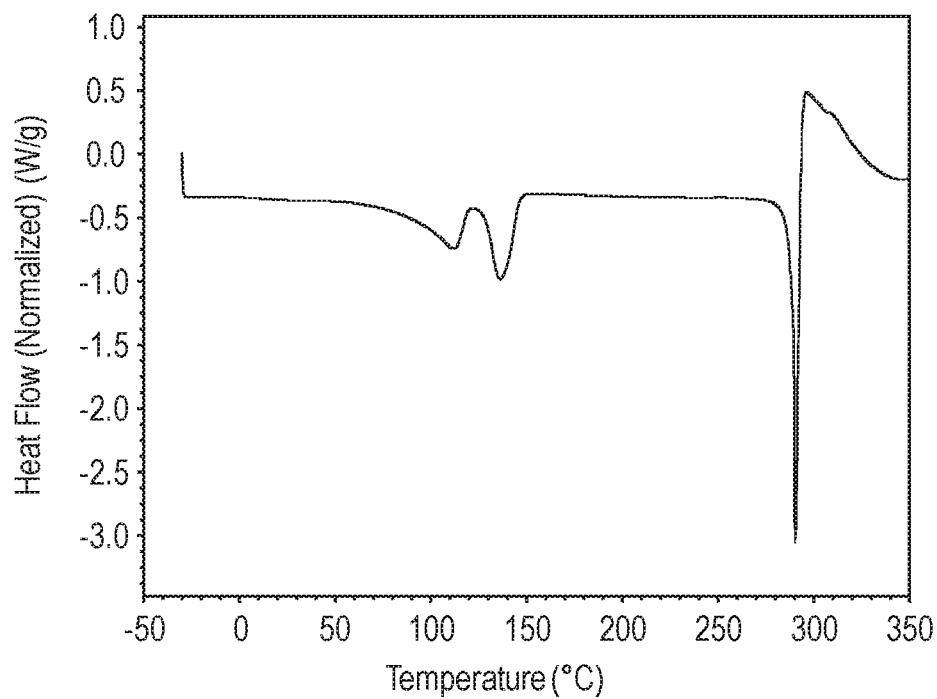
FIG. 45 shows DSC data for the crystalline p-Dioxane Solvate Form I of Compound 1.
Figure 46:
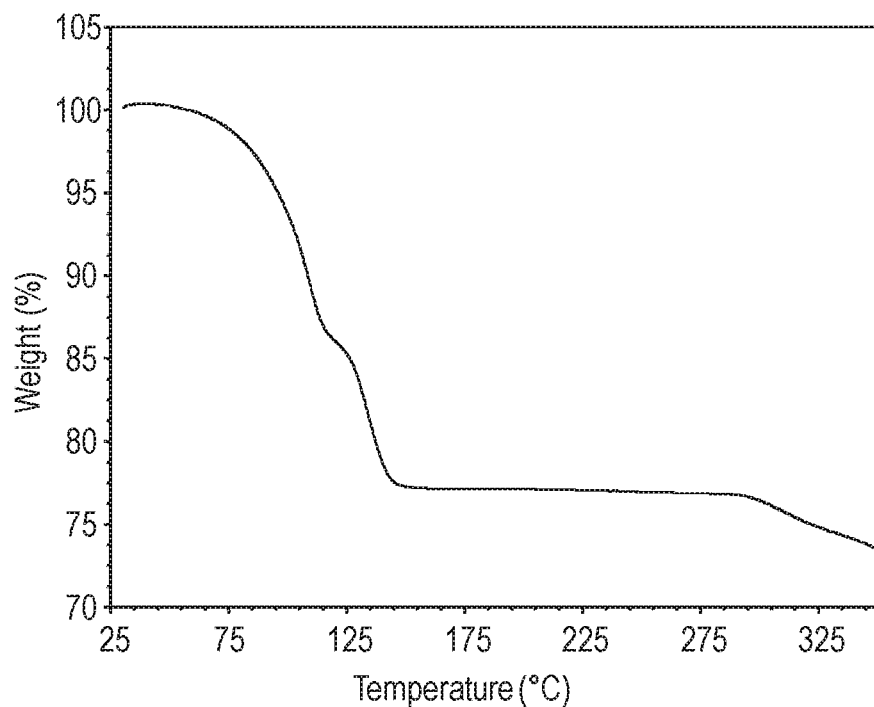
FIG. 46 shows TGA data for the crystalline p-Dioxane Solvate Form I of Compound 1.

The crystalline p-dioxane solvate Form I of Compound 1 prepared above was characterized by proton NMR, X-ray powder diffraction (XRPD) data (FIG. 44), DSC (FIG. 45), and TGA (FIG. 46).

DSC endotherm onset of about 112° C., TGA comprising an approximate 23.2% weight loss when heated from about 25° C. to about 150° C. (1.9 mol p-dioxane)

NMR 1.9 mol p-dioxane $^1$H NMR (400 MHz, DMSO-$d_6$) δ ppm 0.84-1.00 (m, 3 H) 1.07 (d, J=6.61 Hz, 3 H) 1.35 (d, J=6.82 Hz, 3 H) 1.90 (s, 2 H) 2.52-2.77 (m, 2 H) 3.05-3.28 (m, 1 H) 3.32 (s, 4 H) 3.58-3.78 (m, 3 H) 3.98-4.07 (m, 1 H) 4.09-4.20 (m, 1 H) 4.09-4.19 (m, 1 H) 4.15-4.43 (m, 1 H) 4.16-4.21 (m, 1 H) 4.22-4.45 (m, 1 H) 4.23-4.45 (m, 1 H) 4.90 (br s, 1 H) 5.61-5.80 (m, 1 H) 6.20 (br dd, J=16.62, 4.48 Hz, 1 H) 6.58-6.76 (m, 2 H) 6.79-6.93 (m, 1 H) 7.10-7.21 (m, 1 H) 7.21-7.31 (m, 1 H) 8.14-8.36 (m, 3 H) 8.39 (d, J=4.90 Hz, 1 H) 10.20 (br s, 1 H)

TABLE 14

XRPD data of the Crystalline p-Dioxane Solvate Form I of Compound 1
XRPD Peak Table

| Pos. [°2Th.] | Rel. Int. [%] |
|---|---|
| 7.8 | 94.7 |
| 9.5 | 83.9 |
| 9.6 | 55.6 |
| 10.2 | 7.1 |
| 11.0 | 59.4 |
| 11.3 | 30.2 |
| 11.8 | 1.0 |
| 12.9 | 71.9 |
| 13.2 | 1.6 |
| 13.7 | 6.4 |
| 14.3 | 13.0 |
| 15.8 | 81.2 |
| 16.4 | 4.8 |
| 16.6 | 4.5 |
| 17.7 | 81.5 |
| 18.1 | 49.0 |
| 18.3 | 40.0 |
| 18.6 | 85.4 |
| 18.8 | 100.0 |
| 19.0 | 63.4 |
| 19.2 | 94.1 |
| 19.8 | 88.2 |
| 20.0 | 73.8 |
| 20.4 | 13.1 |
| 20.5 | 42.2 |
| 20.9 | 13.0 |
| 21.2 | 41.5 |
| 21.6 | 22.5 |
| 21.7 | 20.6 |
| 22.0 | 34.7 |
| 22.4 | 6.1 |
| 22.7 | 8.0 |
| 23.0 | 3.2 |
| 23.3 | 14.6 |
| 23.6 | 32.9 |
| 23.7 | 47.2 |
| 24.1 | 55.3 |
| 24.3 | 8.5 |
| 25.0 | 25.5 |
| 25.9 | 21.9 |
| 26.6 | 26.6 |
| 27.0 | 20.1 |
| 27.3 | 7.1 |
| 27.4 | 9.2 |
| 27.7 | 10.6 |
| 28.0 | 6.4 |
| 28.1 | 5.0 |
| 28.6 | 20.8 |
| 28.8 | 6.5 |
| 29.1 | 6.3 |
| 29.2 | 5.9 |
| 29.6 | 6.6 |
| 30.0 | 7.1 |
| 30.4 | 4.6 |
| 30.5 | 8.0 |
| 31.0 | 12.2 |
| 31.5 | 3.3 |
| 32.0 | 8.6 |
| 32.3 | 5.4 |
| 32.7 | 1.2 |
| 33.3 | 9.4 |
| 34.3 | 3.1 |
| 34.9 | 4.0 |
| 35.5 | 4.3 |
| 35.9 | 5.3 |
| 36.3 | 1.1 |
| 36.8 | 2.8 |
| 37.0 | 5.2 |
| 37.4 | 1.0 |
| 37.8 | 1.7 |
| 38.9 | 3.1 |
| 39.5 | 3.6 |

Example 15: Preparation of the Crystalline Methanol Solvate Form I of Compound 1

The crystalline methanol (MeOH) solvate Form I of Compound 1 was prepared by placing Compound 1 in a small open vial then placing this vial inside a larger vial containing MeOH and capped to vapor stress the solids at RT for 4 days.

Figure 47:
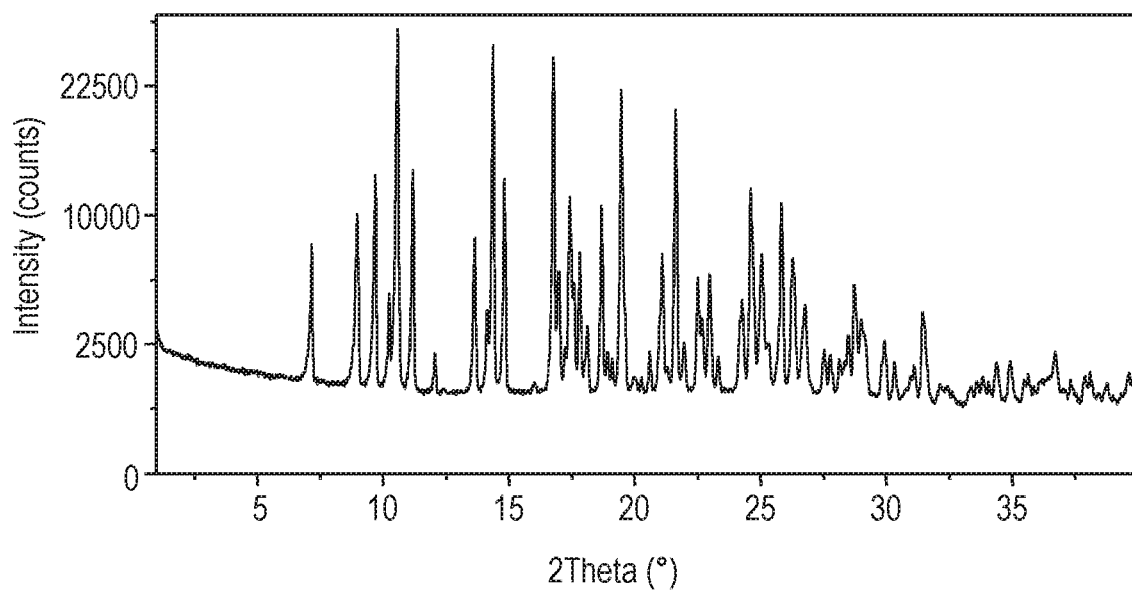
FIG. 47 shows XRPD data for the crystalline MeOH Solvate Form I of Compound 1.
Figure 48:
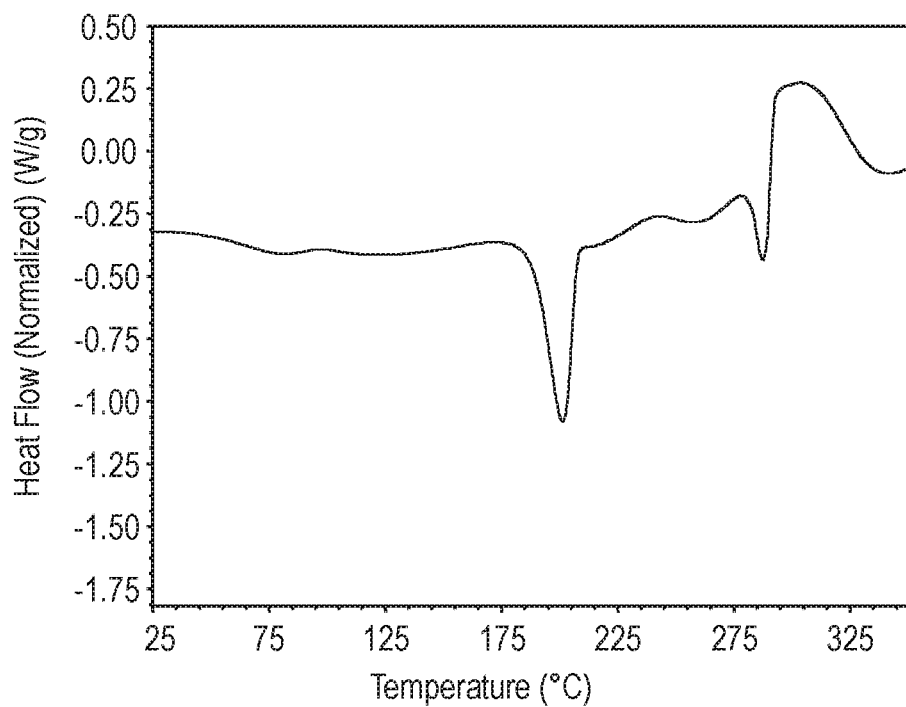
FIG. 48 shows DSC data for the crystalline MeOH Solvate Form I of Compound 1.
Figure 49:
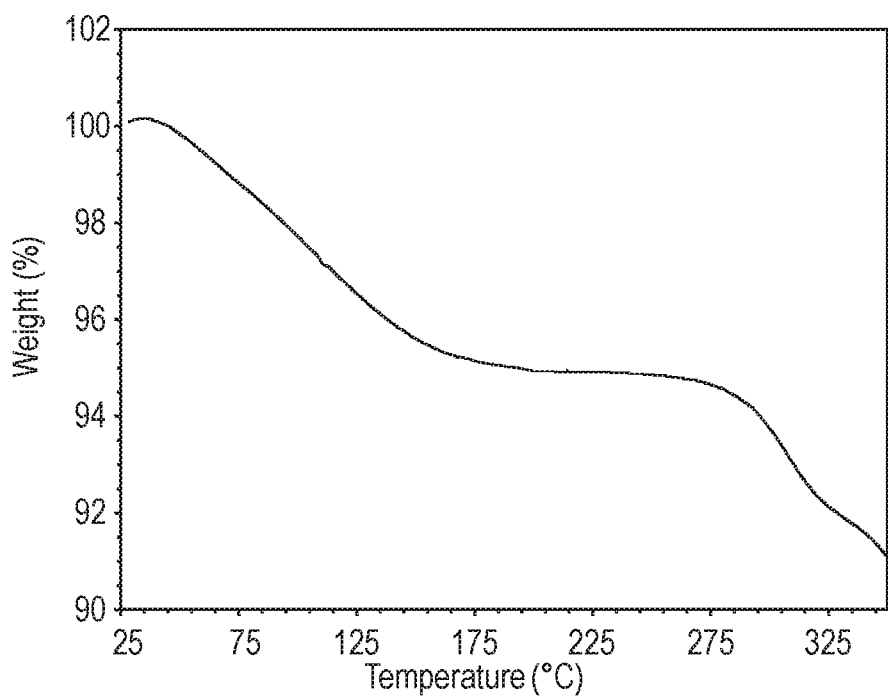
FIG. 49 shows TGA data for the crystalline MeOH Solvate Form I of Compound 1.

The crystalline MeOH Solvate Form I of Compound 1 prepared above was characterized by proton NMR, X-ray powder diffraction (XRPD) data (FIG. 47), DSC (FIG. 48), and TGA (FIG. 49).

DSC endotherm onset of about 57° C., TGA comprising an approximate 5.2% weight loss when heated from about 38° C. to about 220° C. (1.0 mol MeOH)

NMR 0.8 mol MeOH $^1$H NMR (400 MHz, DMSO-d$_6$) δ ppm 0.94 (d, J=6.62 Hz, 3 H) 1.08 (d, J=6.62 Hz, 3 H) 1.35 (d, J=6.84 Hz, 3 H) 1.90 (s, 3 H) 2.64-2.80 (m, 1 H) 3.18 (d, J=4.92 Hz, 3 H) 3.48-3.76 (m, 2 H) 3.97-4.21 (m, 2 H) 4.21-4.47 (m, 2 H) 4.91 (br s, 1 H) 5.69-5.86 (m, 1 H) 6.21 (br dd, J=16.67, 4.49 Hz, 1 H) 6.63-6.79 (m, 2 H) 6.80-6.98 (m, 1 H) 7.17-7.31 (m, 2H) 8.18-8.35 (m, 1 H) 8.39 (d, J=4.92 Hz, 1 H) 10.22 (br s, 1 H)

TABLE 15

XRPD data of the Crystalline MeOH Solvate Form I of Compound 1
XRPD Peak Table

| Pos. [°2Th.] | Rel. Int. [%] |
|---|---|
| 7.2 | 22.9 |
| 9.0 | 30.8 |
| 9.7 | 42.7 |
| 10.3 | 13.3 |
| 10.6 | 100.0 |
| 11.2 | 44.1 |
| 12.1 | 4.1 |
| 13.7 | 26.4 |
| 14.1 | 10.9 |
| 14.4 | 91.4 |
| 14.9 | 43.3 |
| 16.0 | 0.9 |
| 16.8 | 91.1 |
| 17.0 | 18.4 |
| 17.2 | 5.0 |
| 17.4 | 37.0 |
| 17.6 | 15.5 |
| 17.8 | 22.7 |
| 18.1 | 8.0 |
| 18.7 | 35.3 |
| 18.9 | 4.5 |
| 19.1 | 3.6 |
| 19.5 | 74.7 |
| 20.0 | 1.7 |
| 20.3 | 1.6 |
| 20.6 | 4.7 |
| 21.1 | 21.9 |
| 21.3 | 2.9 |
| 21.7 | 68.4 |
| 22.0 | 5.9 |
| 22.5 | 17.1 |
| 22.7 | 9.7 |
| 23.0 | 17.7 |
| 23.3 | 4.1 |
| 24.2 | 8.2 |
| 24.3 | 12.9 |
| 24.6 | 40.5 |
| 25.1 | 22.7 |
| 25.4 | 5.6 |
| 25.9 | 35.7 |
| 26.3 | 21.1 |
| 26.8 | 12.1 |
| 27.5 | 5.2 |
| 27.8 | 4.5 |
| 28.1 | 3.8 |
| 28.5 | 7.3 |
| 28.7 | 15.9 |
| 29.0 | 9.4 |
| 29.2 | 7.1 |
| 29.9 | 6.5 |
| 30.3 | 3.7 |
| 31.1 | 3.3 |
| 31.4 | 10.8 |
| 31.5 | 9.2 |
| 32.2 | 1.4 |
| 32.4 | 1.3 |
| 33.4 | 1.3 |
| 33.6 | 1.7 |
| 33.8 | 2.2 |
| 34.1 | 1.6 |
| 34.4 | 3.6 |
| 34.9 | 3.1 |
| 34.9 | 3.9 |
| 35.5 | 1.8 |
| 35.7 | 2.4 |
| 36.1 | 1.7 |
| 36.7 | 5.1 |
| 37.3 | 1.9 |
| 37.9 | 2.2 |
| 38.1 | 2.8 |
| 38.8 | 1.6 |
| 39.7 | 2.6 |
| 39.9 | 3.0 |

Example 16: Preparation of the Crystalline IPA Solvate Form I Of Compound 1

The crystalline isopropanol (IPA) solvate Form I of Compound 1 was prepared by slurry of amorphous Compound 1 in IPA at RT for 5 days.

Figure 50:
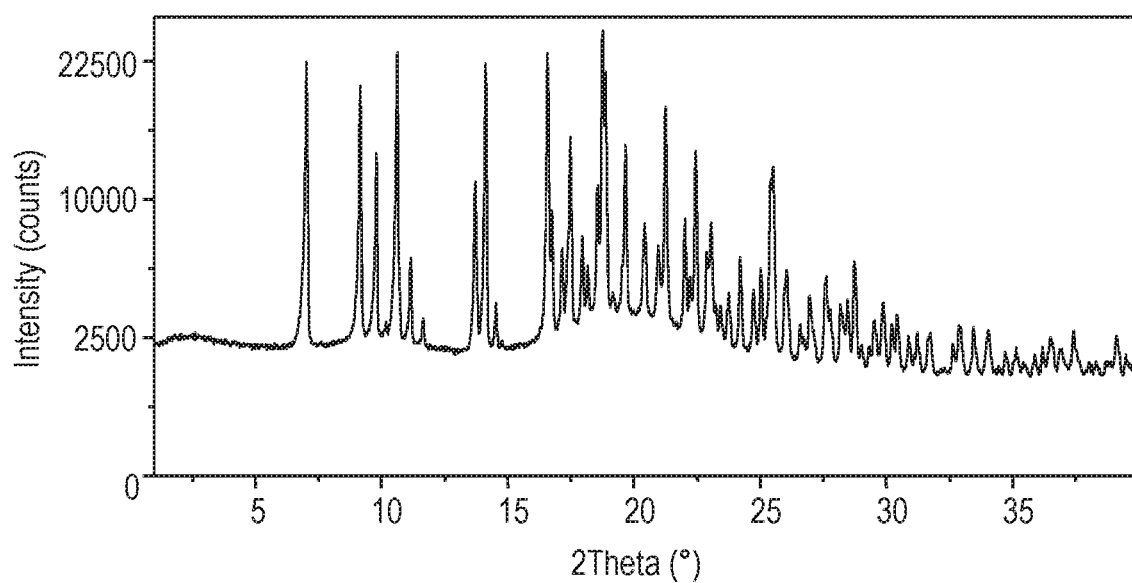
FIG. 50 shows XRPD data for the crystalline IPA Solvate Form I of Compound 1.
Figure 51:
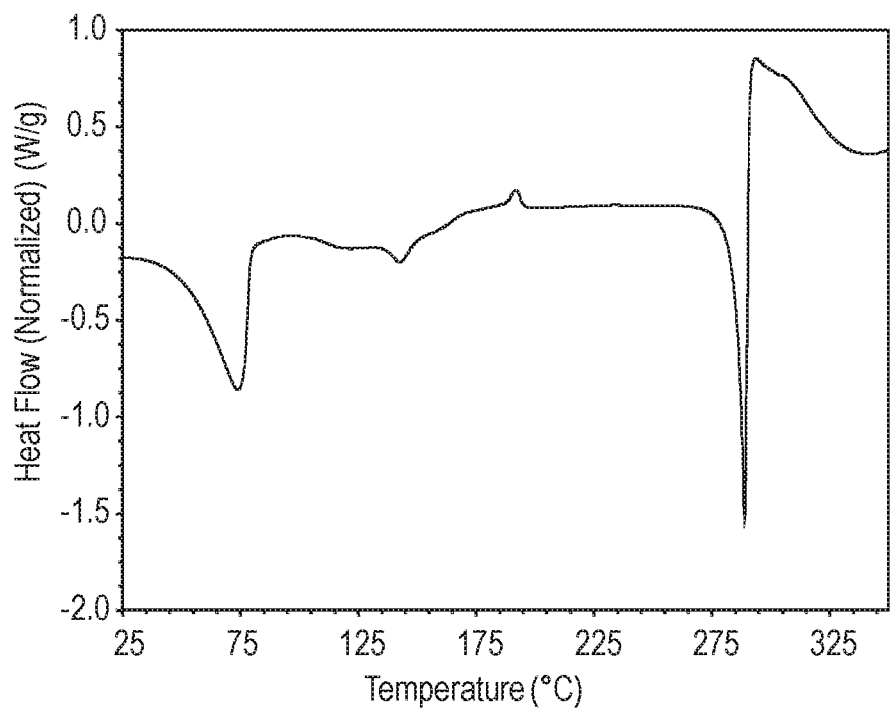
FIG. 51 shows DSC data for the crystalline IPA Solvate Form I of Compound 1.
Figure 52:
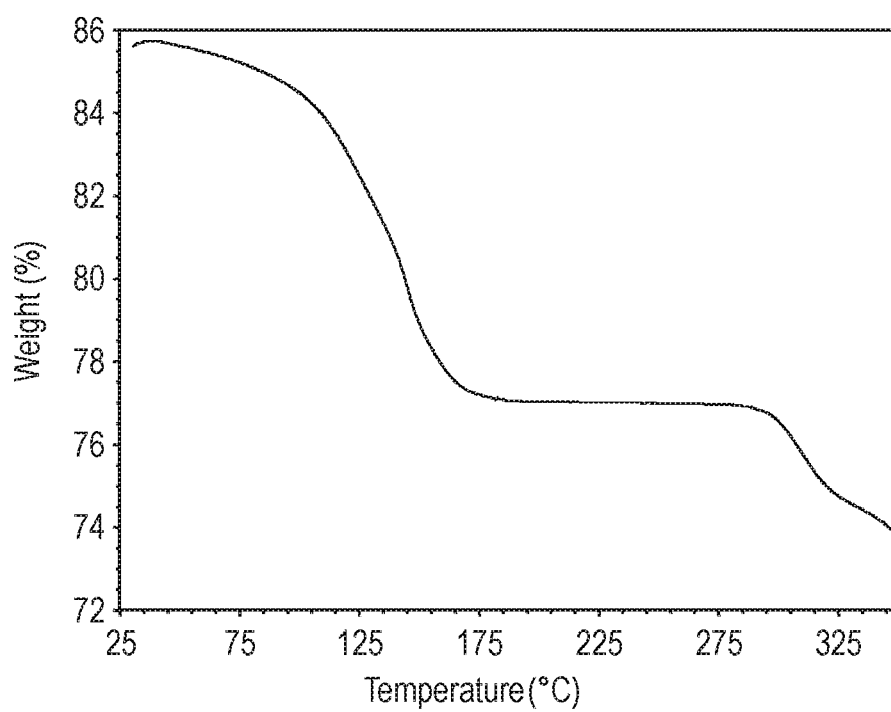
FIG. 52 shows TGA data for the crystalline IPA Solvate Form I of Compound 1.

The crystalline IPA solvate Form I of Compound 1 prepared above was characterized by proton NMR, X-ray powder diffraction (XRPD) data (FIG. 50), DSC (FIG. 51), and TGA (FIG. 52).

DSC endotherm onset of about 56° C., TGA comprising an approximate 8.7% weight loss when heated from about 39° C. to about 190° C. (0.9 mol IPA)

NMR 2.3 mol IPA $^1$H NMR (400 MHz, DMSO-d$_6$) δ ppm 0.94 (d, J=6.62 Hz, 3 H) 1.02-1.06 (m, 1 H) 1.05 (d, J=5.98 Hz, 14 H) 1.35 (d, J=6.62 Hz, 3 H) 1.90 (s, 3 H) 2.72 (br s, 1 H) 3.10-3.21 (m, 1 H) 3.45-3.58 (m, 1 H) 3.78 (td, J=6.09, 4.06 Hz, 9 H) 3.98-4.09 (m, 1 H) 4.16 (br s, 1 H) 4.35 (d, J=4.06 Hz, 8 H) 4.91 (br d, J=0.85 Hz, 1 H) 5.73-5.83 (m, 2 H) 6.16-6.28 (m, 1 H) 6.66-6.93 (m, 5 H) 7.19 (dd, J=4.81, 0.75 Hz, 2 H) 7.23-7.33 (m, 2 H) 8.39 (d, J=4.92 Hz, 3 H) 10.21 (br s, 1 H).

TABLE 16

XRPD data of the Crystalline MeOH Solvate Form I of Compound 1
XRPD Peak Table:

| Pos. [°2Th.] | Rel. Int. [%] |
|---|---|
| 7.1 | 84.1 |
| 9.2 | 73.8 |
| 9.8 | 47.9 |
| 10.2 | 4.2 |
| 10.6 | 89.1 |
| 11.2 | 17.2 |

TABLE 16-continued

XRPD data of the Crystalline MeOH Solvate Form I of Compound 1
XRPD Peak Table:

| Pos. [°2Th.] | Rel. Int. [%] |
|---|---|
| 11.7 | 5.1 |
| 13.7 | 38.9 |
| 14.1 | 82.0 |
| 14.6 | 7.5 |
| 14.8 | 1.8 |
| 16.6 | 90.0 |
| 16.8 | 30.3 |
| 17.2 | 20.0 |
| 17.5 | 52.1 |
| 18.0 | 23.3 |
| 18.2 | 15.9 |
| 18.6 | 38.1 |
| 18.8 | 100.0 |
| 18.9 | 75.5 |
| 19.2 | 10.6 |
| 19.7 | 52.3 |
| 20.4 | 27.0 |
| 21.0 | 21.5 |
| 21.3 | 65.6 |
| 22.0 | 28.6 |
| 22.2 | 14.3 |
| 22.5 | 50.5 |
| 22.9 | 19.9 |
| 23.1 | 27.1 |
| 23.3 | 8.6 |
| 23.5 | 8.8 |
| 23.8 | 11.3 |
| 24.2 | 19.0 |
| 24.8 | 12.0 |
| 25.0 | 16.1 |
| 25.4 | 37.9 |
| 25.5 | 45.3 |
| 26.1 | 16.0 |
| 26.6 | 5.6 |
| 27.0 | 11.0 |
| 27.7 | 15.1 |
| 27.8 | 8.3 |
| 28.2 | 8.7 |
| 28.5 | 10.5 |
| 28.7 | 18.2 |
| 29.0 | 2.9 |
| 29.3 | 2.6 |
| 29.5 | 6.7 |
| 29.9 | 9.8 |
| 30.2 | 6.2 |
| 30.4 | 7.9 |
| 30.9 | 4.5 |
| 31.2 | 5.0 |
| 31.7 | 4.2 |
| 31.8 | 4.8 |
| 32.7 | 3.4 |
| 32.9 | 6.2 |
| 33.0 | 5.8 |
| 33.5 | 6.0 |
| 34.1 | 5.5 |
| 34.7 | 2.3 |
| 35.2 | 3.0 |
| 35.5 | 0.8 |
| 35.9 | 2.1 |
| 36.2 | 2.5 |
| 36.5 | 4.4 |
| 36.6 | 3.5 |
| 36.9 | 2.7 |
| 37.0 | 2.6 |
| 37.4 | 5.7 |
| 38.1 | 1.2 |
| 38.3 | 1.0 |
| 38.7 | 1.2 |
| 39.1 | 4.9 |
| 39.5 | 2.1 |

Example 17: Preparation of the Crystalline EtOH Solvate Form I of Compound 1

The crystalline ethanol (EtOH) solvate Form I of Compound 1 was prepared by slurry of amorphous Compound 1 in EtOH at RT for 10 days.

Figure 53:
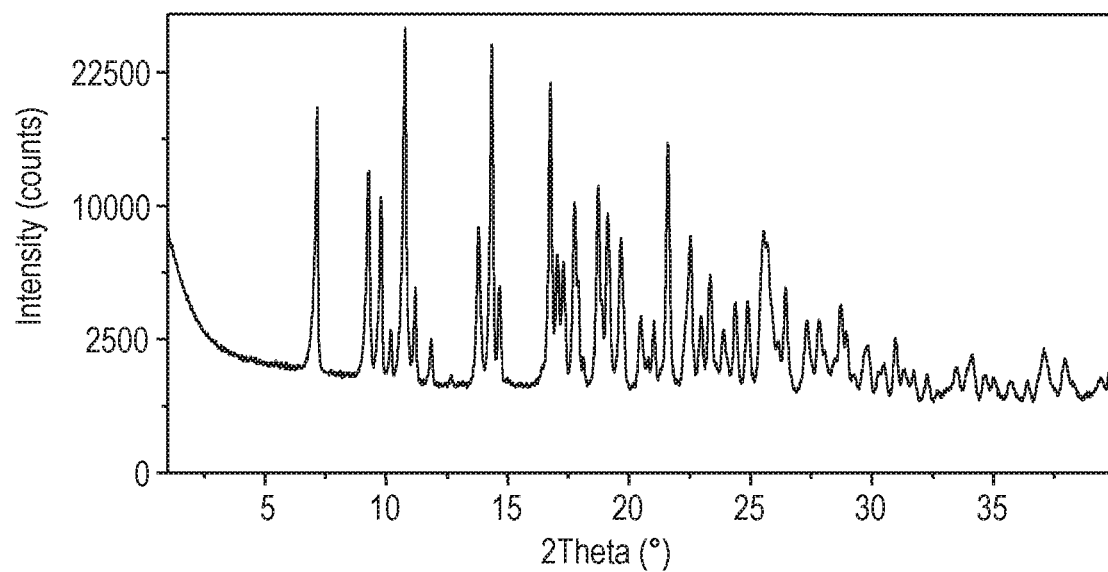
FIG. 53 shows XRPD data for the crystalline EtOH Solvate Form I of Compound 1.
Figure 54:
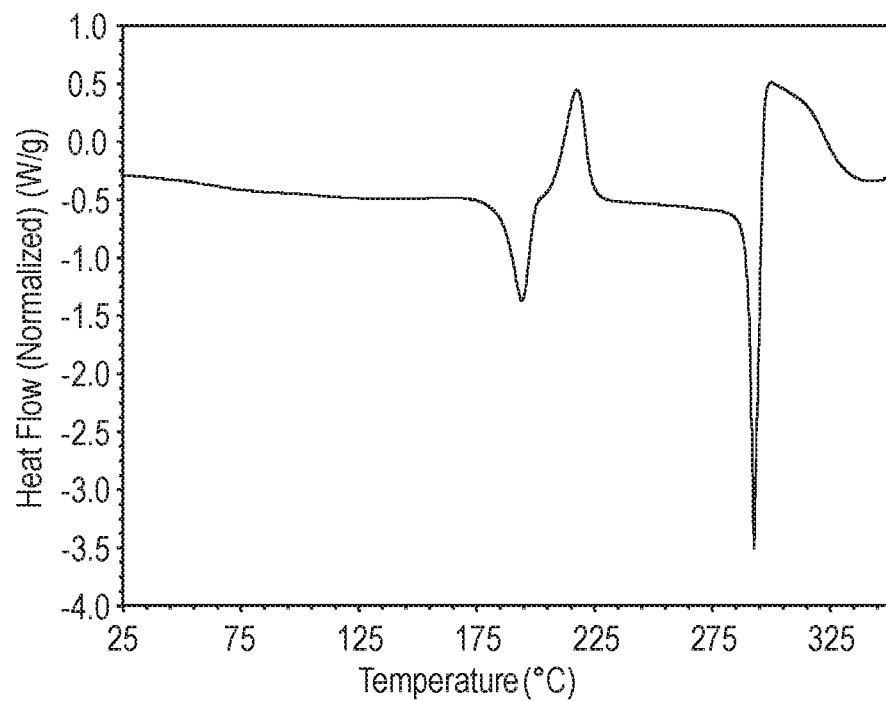
FIG. 54 shows DSC data for the crystalline EtOH Solvate Form I of Compound 1
Figure 55:
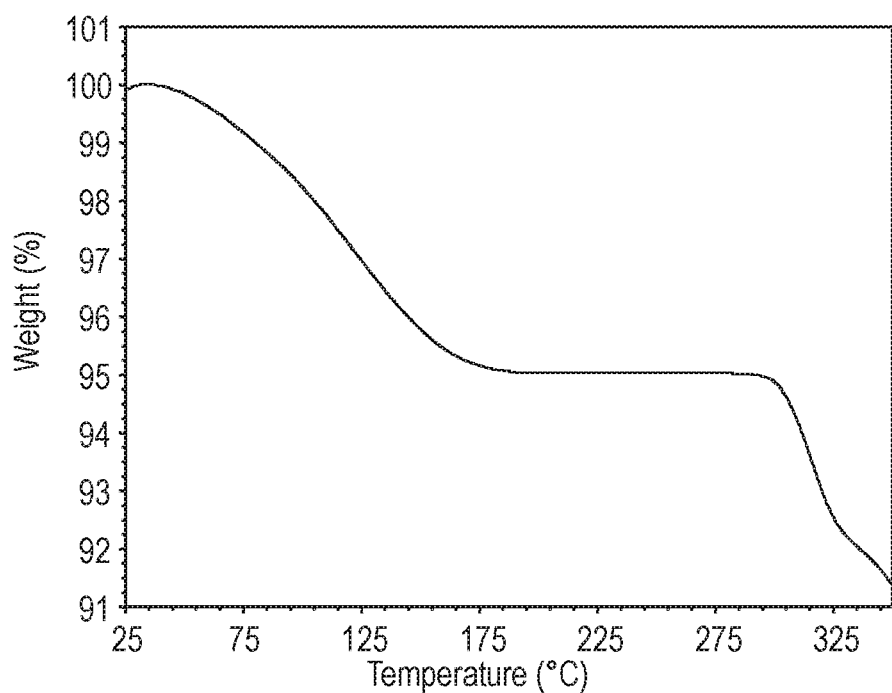
FIG. 55 shows TGA data for the crystalline EtOH Solvate Form I of Compound 1.
Figure 56:
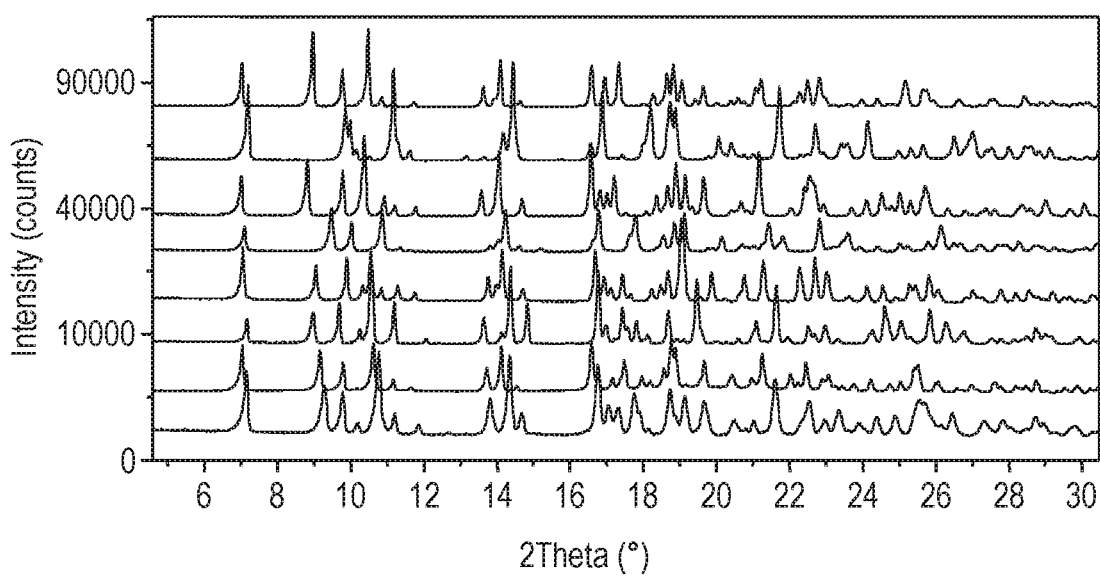
FIG. 56 is the overlay XRPD data for the isostructural solvate forms of Compound 1 (Top to bottom—THF, MeCN, MEK, DCM, acetone, MeOH, IPA, EtOH).

The crystalline EtOH solvate Form I of Compound 1 prepared above was characterized by proton NMR, X-ray powder diffraction (XRPD) data (FIG. 53), DSC (FIG. 54), and TGA (FIG. 55).

DSC endotherm onset of about 194° C., TGA comprising an approximate 5% weight loss when heated from about 36° C. to about 195° C. (0.6 mol EtOH)

NMR 0.7 mol EtOH.

$^1$H NMR (400 MHz, DMSO-$d_6$) δ ppm 0.84-1.02 (m, 5 H) 1.02-1.12 (m, 5 H) 1.35 (d, J=6.82 Hz, 3 H) 1.90 (s, 3 H) 2.52-2.77 (m, 1 H) 3.14 (br t, J=10.87 Hz, 1 H) 3.34-3.57 (m, 2 H) 3.58-3.84 (m, 2 H) 3.86-4.08 (m, 1 H) 4.09-4.21 (m, 1 H) 4.21-4.46 (m, 3 H) 4.90 (br s, 1 H) 5.51-5.80 (m, 1 H) 6.20 (br dd, J=16.52, 4.58 Hz, 1 H) 6.62-6.75 (m, 2 H) 6.86 (dt, J=16.30, 11.24 Hz, 1 H) 7.13-7.19 (m, 1 H) 7.27 (td, J=8.20, 7.03 Hz, 1 H) 8.16-8.36 (m, 2 H) 8.39 (d, J=4.90 Hz, 1 H) 10.20 (br s, 1 H).

TABLE 17

XRPD data of the Crystalline EtOH Solvate Form I of Compound 1
XRPD Peak Table:

| Pos. [°2Th.] | Rel. Int. [%] |
|---|---|
| 7.2 | 63.3 |
| 9.3 | 42.8 |
| 9.8 | 35.9 |
| 10.2 | 6.1 |
| 10.8 | 100.0 |
| 11.2 | 13.4 |
| 11.9 | 5.3 |
| 12.7 | 0.9 |
| 13.8 | 28.1 |
| 14.4 | 91.3 |
| 14.7 | 14.3 |
| 16.8 | 77.0 |
| 17.1 | 21.3 |
| 17.3 | 19.5 |
| 17.8 | 34.9 |
| 17.9 | 14.9 |
| 18.2 | 3.0 |
| 18.8 | 40.0 |
| 19.1 | 31.5 |
| 19.7 | 25.4 |
| 20.5 | 8.9 |
| 20.8 | 3.3 |
| 21.0 | 8.2 |
| 21.6 | 54.2 |
| 22.6 | 26.1 |
| 23.0 | 9.5 |
| 23.4 | 16.6 |
| 23.9 | 7.1 |
| 24.4 | 11.8 |
| 24.9 | 11.5 |
| 25.6 | 27.2 |
| 25.7 | 24.1 |
| 26.2 | 5.4 |
| 26.5 | 14.6 |
| 27.3 | 8.6 |
| 27.8 | 8.2 |
| 28.7 | 11.6 |
| 29.0 | 7.1 |
| 29.3 | 1.6 |
| 29.9 | 4.9 |
| 30.3 | 1.8 |
| 30.5 | 3.0 |
| 31.0 | 6.1 |
| 31.3 | 2.3 |
| 31.8 | 2.1 |

TABLE 17-continued

XRPD data of the Crystalline EtOH Solvate Form I of Compound 1
XRPD Peak Table:

| Pos. [°2Th.] | Rel. Int. [%] |
| --- | --- |
| 32.3 | 1.7 |
| 32.7 | 0.1 |
| 33.5 | 2.4 |
| 34.1 | 4.1 |
| 34.7 | 1.7 |
| 35.0 | 1.6 |
| 35.7 | 1.1 |
| 36.5 | 1.3 |
| 37.1 | 4.8 |
| 38.0 | 3.2 |
| 39.5 | 1.4 |
| 39.8 | 1.8 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the disclosure. It is intended, therefore, that the invention be defined by the scope of the claims that follow and that such claims be interpreted as broadly as is reasonable.

What is claimed is:

1. A compound, wherein the compound is a crystalline form of the M atropisomer of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1) and wherein the compound is characterized by $^{19}F$ solid state NMR comprising peaks at approximately −109 and −120 ppm.

2. The compound of claim 1, wherein the compound is characterized by $^{19}F$ solid state NMR comprising peaks at approximately −49, −60, −79, −90, −109, −120, −138, −150, −168, and −179 ppm.

3. The compound of claim 2, wherein the $^{19}F$ solid state NMR is measured at a spinning frequency of 14 kHz.

4. A pharmaceutical composition comprising the compound of claim 1 and a pharmaceutically acceptable excipient.

5. The pharmaceutical composition of claim 4, wherein the pharmaceutical composition is a tablet.

6. The pharmaceutical composition of claim 5, wherein the tablet comprises 120 mg of the compound.

7. A pharmaceutical composition comprising the compound of claim 2 and a pharmaceutically acceptable excipient.

8. The pharmaceutical composition of claim 7, wherein the pharmaceutical composition is a tablet.

9. The pharmaceutical composition of claim 8, wherein the tablet comprises 120 mg of the compound.

10. A pharmaceutical composition comprising the compound of claim 3 and a pharmaceutically acceptable excipient.

11. The pharmaceutical composition of claim 10, wherein the pharmaceutical composition is a tablet.

12. The pharmaceutical composition of claim 11, wherein the tablet comprises 120 mg of the compound.

13. A method of treating cancer having a KRAS G12C mutation in a patient in need thereof, the method comprising administering to the patient a therapeutically effective amount of the compound of claim 1, wherein the cancer having a KRAS G12C mutation is non-small cell lung cancer, small intestine cancer, appendix cancer, colorectal cancer, endometrial cancer, pancreatic cancer, liver cancer, small cell lung cancer, cervical cancer, germ cell tumor, ovarian cancer, pancreatic neuroendocrine tumor, bladder cancer, myelodysplastic/myeloproliferative neoplasms, head and neck cancer, esophageal cancer, soft tissue sarcoma, malignant mesothelioma, thyroid cancer, skin cancer, gastric cancer, or bile duct cancer.

14. The method of claim 13, wherein the cancer having a KRAS G12C mutation is non-small cell lung cancer, small intestine cancer, appendix cancer, colorectal cancer, endometrial cancer, pancreatic cancer, skin cancer, gastric cancer, or bile duct cancer.

15. The method of claim 14, wherein the cancer having a KRAS G12C mutation is non-small cell lung cancer.

16. The method of claim 14, wherein the cancer having a KRAS G12C mutation is colorectal cancer.

17. The method of claim 14, wherein the cancer having a KRAS G12C mutation is pancreatic cancer.

18. The method of claim 14, wherein the cancer having a KRAS G12C mutation is non-small cell lung cancer, colorectal cancer, or pancreatic cancer.

19. The method of claim 15, wherein the compound is administered to an adult.

20. The method of claim 16, wherein the compound is administered to an adult.

21. The method of claim 17, wherein the compound is administered to an adult.

22. The method of claim 18, wherein the compound is administered to an adult.

23. A method of treating cancer having a KRAS G12C mutation in a patient in need thereof, the method comprising administering to the patient a therapeutically effective amount of the compound of claim 2, wherein the cancer having a KRAS G12C mutation is non-small cell lung cancer, small intestine cancer, appendix cancer, colorectal cancer, endometrial cancer, pancreatic cancer, liver cancer, small cell lung cancer, cervical cancer, germ cell tumor, ovarian cancer, pancreatic neuroendocrine tumor, bladder cancer, myelodysplastic/myeloproliferative neoplasms, head and neck cancer, esophageal cancer, soft tissue sarcoma, malignant mesothelioma, thyroid cancer, skin cancer, gastric cancer, or bile duct cancer.

24. The method of claim 23, wherein the cancer having a KRAS G12C mutation is non-small cell lung cancer, small intestine cancer, appendix cancer, colorectal cancer, endometrial cancer, pancreatic cancer, skin cancer, gastric cancer, or bile duct cancer.

25. The method of claim 24, wherein the cancer having a KRAS G12C mutation is non-small cell lung cancer.

26. The method of claim 24, wherein the cancer having a KRAS G12C mutation is colorectal cancer.

27. The method of claim 24, wherein the cancer having a KRAS G12C mutation is pancreatic cancer.

28. The method of claim 24, wherein the cancer having a KRAS G12C mutation is non-small cell lung cancer, colorectal cancer, or pancreatic cancer.

29. The method of claim 25, wherein the compound is administered to an adult.

30. The method of claim 26, wherein the compound is administered to an adult.

31. The method of claim 27, wherein the compound is administered to an adult.

32. The method of claim 28, wherein the compound is administered to an adult.

33. A method of treating cancer having a KRAS G12C mutation in a patient in need thereof, the method comprising administering to the patient a therapeutically effective amount of the compound of claim 3, wherein the cancer having a KRAS G12C mutation is non-small cell lung cancer, small intestine cancer, appendix cancer, colorectal cancer, endometrial cancer, pancreatic cancer, liver cancer, small cell lung cancer, cervical cancer, germ cell tumor, ovarian cancer, pancreatic neuroendocrine tumor, bladder cancer, myelodysplastic/myeloproliferative neoplasms, head and neck cancer, esophageal cancer, soft tissue sarcoma, malignant mesothelioma, thyroid cancer, skin cancer, gastric cancer, or bile duct cancer.

34. The method of claim 33, wherein the cancer having a KRAS G12C mutation is non-small cell lung cancer, small intestine cancer, appendix cancer, colorectal cancer, endometrial cancer, pancreatic cancer, skin cancer, gastric cancer, or bile duct cancer.

35. The method of claim 34, wherein the cancer having a KRAS G12C mutation is non-small cell lung cancer.

36. The method of claim 34, wherein the cancer having a KRAS G12C mutation is colorectal cancer.

37. The method of claim 34, wherein the cancer having a KRAS G12C mutation is pancreatic cancer.

38. The method of claim 34, wherein the cancer having a KRAS G12C mutation is non-small cell lung cancer, colorectal cancer, or pancreatic cancer.

39. The method of claim 35, wherein the compound is administered to an adult.

40. The method of claim 36, wherein the compound is administered to an adult.

41. The method of claim 37, wherein the compound is administered to an adult.

42. The method of claim 38, wherein the compound is administered to an adult.

\* \* \* \* \*